US010287600B2

(12) United States Patent
Browse et al.

(10) Patent No.: US 10,287,600 B2
(45) Date of Patent: May 14, 2019

(54) COMPOSITIONS AND METHODS FOR DIFFERENTIAL REGULATION OF FATTY ACID UNSATURATION IN MEMBRANE LIPIDS AND SEED OIL

(71) Applicant: Washington State University, Pullman, WA (US)

(72) Inventors: John A. Browse, Palouse, WA (US); Chaofu Lu, Bozeman, MT (US); Zhanguo Xin, Lubbock, TX (US)

(73) Assignee: Washington State University, Pullman, WA (US)

( * ) Notice: Subject to any disclaimer, the term of this patent is extended or adjusted under 35 U.S.C. 154(b) by 373 days.

(21) Appl. No.: 14/948,166

(22) Filed: Nov. 20, 2015

(65) Prior Publication Data

US 2016/0272985 A1    Sep. 22, 2016

Related U.S. Application Data

(63) Continuation of application No. 12/921,119, filed as application No. PCT/US2009/036066 on Mar. 4, 2009, now Pat. No. 9,200,293.

(60) Provisional application No. 61/149,288, filed on Feb. 2, 2009, provisional application No. 61/033,742, filed on Mar. 4, 2008.

(51) Int. Cl.
| C12N 15/82 | (2006.01) |
| A01H 5/10 | (2018.01) |
| C12N 9/12 | (2006.01) |
| A23D 9/013 | (2006.01) |
| C10L 1/02 | (2006.01) |
| C11B 1/00 | (2006.01) |

(52) U.S. Cl.
CPC .......... *C12N 15/8247* (2013.01); *A01H 5/10* (2013.01); *A23D 9/013* (2013.01); *C10L 1/026* (2013.01); *C11B 1/00* (2013.01); *C12N 9/1288* (2013.01); *C10L 2200/0476* (2013.01); *C10L 2270/026* (2013.01); *C12Y 207/08002* (2013.01)

(58) Field of Classification Search
None
See application file for complete search history.

(56) References Cited

U.S. PATENT DOCUMENTS

| 4,771,002 A | 9/1988 | Gelvin |
| 4,959,314 A | 9/1990 | Mark et al. |
| 5,102,796 A | 4/1992 | Hall et al. |
| 5,106,739 A | 4/1992 | Comai et al. |
| 5,164,316 A | 11/1992 | McPherson et al. |
| 5,182,200 A | 1/1993 | Slightom et al. |
| 5,364,780 A | 11/1994 | Hershey et al. |
| 5,378,619 A | 1/1995 | Rogers |
| 5,428,147 A | 6/1995 | Barker et al. |
| 5,563,328 A | 10/1996 | Mitra et al. |
| 5,756,290 A | 5/1998 | Haselkorn et al. |
| 5,850,019 A | 12/1998 | Maiti et al. |
| 6,153,812 A | 11/2000 | Fry et al. |
| 2003/0221217 A1 | 11/2003 | Yao et al. |
| 2004/0123343 A1* | 6/2004 | La Rosa .............. C07K 14/415 800/278 |
| 2006/0150283 A1 | 7/2006 | Alexandrov et al. |
| 2006/0206963 A1 | 9/2006 | Voelker et al. |

FOREIGN PATENT DOCUMENTS

| EP | 0332104 A2 | 9/1989 |
| EP | 1033405 A2 | 9/2000 |
| EP | 2018431 B1 | 8/2011 |
| JP | 2002514428 A | 5/2002 |
| WO | 9321334 A1 | 10/1993 |
| WO | 9514098 A1 | 5/1995 |
| WO | 9623898 A1 | 8/1996 |
| WO | 9706269 A1 | 2/1997 |
| WO | 9741228 A2 | 11/1997 |
| WO | 9953050 A1 | 10/1999 |
| WO | 9958689 A1 | 11/1999 |
| WO | 0112824 A1 | 2/2001 |
| WO | 02059294 A1 | 8/2002 |
| WO | 03076619 A1 | 9/2003 |

(Continued)

OTHER PUBLICATIONS

Lemieux et al 1990 (Theoretical and Applied Genetics 80: p. 234-240). Of record in parent case.*
Lu et al 2009 (PNAS 106:44 p. 188337-18842). Of record in parent case.*
Odell et al. "Identification of DNA sequences required for activity of the cauliflower mosaic virus 35S promoter." Nature, 313. pp. 810-812. Feb. 28, 1985.
Okuley et al., "*Arabidopsis* FAD2 Gene Encodes the Enzyme That is Essential for Polyunsaturdated Lipid Synthesis." The Plant Cell, 6(1). pp. 147-158. Jan. 1994.
Ostade et al., "Human TNF mutants with selective activity on the p55 receptor." Nature, 361(6409). pp. 266-269. Jan. 21, 1993.

(Continued)

*Primary Examiner* — Matthew R Keogh
(74) *Attorney, Agent, or Firm* — Klarquist Sparkman, LLP

(57) ABSTRACT

Aspects of the invention provide methods for differential regulation of fatty acid unsaturation in seed oil and membrane lipids of plants based on modulation of a previously unknown biosynthetic pathway involving a novel phosphatidylcholine:diacylglycerol    cholinephosphotransferase (PDCT) that regulates phosphatidylcholine biosynthesis in developing oil seed plants. Specific aspects relate to inventive PDCT polypeptides including, for example, variants, deletions, muteins, fusion proteins, and orthologs thereof (collectively PDCT proteins), to nucleic acids encoding same, to plants comprising such PDCT sequences or proteins or devoid or depleted of such PDCT proteins or sequences, and to methods for generating plants having altered or no PDCT expression and/or activity, including but not limited to methods comprising mutagenesis, recombinant DNA, transgenics, etc.

7 Claims, 11 Drawing Sheets
Specification includes a Sequence Listing.

(56) References Cited

FOREIGN PATENT DOCUMENTS

| WO | 2005047505 A2 | 5/2005 |
| --- | --- | --- |
| WO | 2006044322 A2 | 4/2006 |
| WO | 2007038738 A2 | 4/2007 |
| WO | 2007095243 A2 | 8/2007 |
| WO | 2007131699 A2 | 11/2007 |

OTHER PUBLICATIONS

Pierrugues et al., "Lipid Phosphate Phosphatases in *Arabidopsis*—Regulation of the AtLPP1 Gene in Response to Street." The Journal of Biological Chemistry, 276(23). pp. 20300-20308. Feb. 26, 2001.

Roberts et al., "A general method for maximizing the expression of a cloned gene," Proceedings of the National Academy of Sciences of the United States of America, 76(2). pp. 760-764. Feb. 1, 1979.

Rogers et al., "Improved Vectors for Plant Transformation: Expression Cassette Vectors and New Selectable Markers." Methods in Enzymology, 153(D). pp. 253-277. 1987.

Ronquist et al., "MrBayes 3: Bayesian phylogenetic inference under mixed models." Bioinformatics, 19(12). pp. 1572-1574. Aug. 12, 2003.

Röder et al., "Efficiency of the tetracycline-dependent gene expression system: complete suppression and efficient induction of the roIB phenotype in transgenic plants." Molecular Genetics and Genomics, 243(1). pp. 32-38. Apr. 1994.

Schena et al., "A steroid-inducible gene expression system for plant cells." Proceedings of the National Academy of Sciences of the United States of America, 88(23). pp. 10421-10425. Dec. 1, 1991.

Schmid et al., "A gene expression map of *Arabidopsis thaliana* development." Nature Genetics, 37(5). pp. 501-506 (and 2 additional pages of online corrections). May 2005.

Schwab et al., "Highly Specific Gene Silencing by Artificial MicroRNAs in *Arabidopsis*." The Plant Cell, 18(5). pp. 1121-1133. May 2006. Published ahead of print Mar. 10, 2006.

Sessions et al., "A High-Throughput *Arabidopsis* Reverse Genetics System." The Plant Cell, 14(12). pp. 2985-2994. Dec. 2002. Published ahead of print Nov. 20, 2002.

Sigal et al., "Integral membrane lipid phosphatases/phosphotransferases: common structure and diverse functions." Biochemical Journal, 387(2). pp. 281-293. Apr. 15, 2005.

Slack et al., "Labelling of Glycerolipids in the Cotyledons of Developing Oilseeds by [1-14C]acetate and [2-3H] glyercol." Biochemical Journal, 1790(2). pp. 421-433. Feb. 15, 1978.

Slack et al., "Some evidence for the reversibility of the cholinephosphotransferasecatalysed reaction in developing inseed cotyledons in vivo." Biochimica et Biophysica Acta (BBA)—Lipids and Lipid Metabolism, 754(1). pp. 10-20. Nov. 1, 1983.

Smith et al., "Comparison of Biosequences." Advances in Applied Mathematics, 2. pp. 482-489. 1981.

Smith et al., "Human Interleukin 4: The Solution Structure of a Four-helix Bundle Protein." Journal of Molecular Biology, 224(4). pp. 899-904. Apr. 20, 1992.

Steinhart et al., "Trans Fatty Acids (TFA): Analysis, Occurrence, Intake and Clinical Relevance." European Journal of Medical Research, 8(8). pp. 358-362. Aug. 20, 2003.

Stoutjesdijk et al., "High-oleic acid Australian *Brassica napus* and *B. juncea* varieties produced by co-suppression of endogenous D12-desaturases," Biochemical Society Transactions, 28(6). pp. 938-940. Dec. 1, 2000.

Stuitje et al., "Seed-expressed fluorescent proteins as versatile tools for easy (co)transformation and high-throughput functional genomics in *Arabidopsis*." Plant Biotechnology Journal, 1(4). pp. 301-309. Jul. 18, 2003.

Stymne et al., "Evidence for the reversibility of the acyl-CoA:lysophosphatidylcholine acyltransferase in microsomal preparations from developing safflower (*Carthamus tinctorius* L.) cotyledons and rat liver." Biochemical Journal, 223(2). pp. 305-314. Oct. 15, 1984.

Ståhl et al., "A family of eukaryotic lysophospholipid acyltransferases with broad specificity." FEBS Letters, 582(2). pp. 305-309. Jan. 23, 2008. Published ahead of print Dec. 26, 2007.

Swofford, Paup*. Phylogenetic Analysis Using Parsimony (*and Other Methods). Version 4.0 beta version. Sinauer Associates. Sunderland, MA. 144 pages. Feb. 2002.

The *Arabidopsis* Information Resource webpage page for SAIL line 1215 E03. www.tair.org (2004).

The *Arabidopsis* Information Resource webpage page for SAIL line 1215 E04. www.tair.org (2004).

Tsunády et al., "Principles Governing Amino Acid Composition of Integral Membrane Proteins: Application to Topology Prediction." Journal of Molecular Biology, 283(2). pp. 489-506. Oct. 23, 1998.

Velten et al., "Isolation of a dual plant promoter fragment from the Ti plasmid of Agrobacterium tumefaciens." The EMBO Journal, 3(12). pp. 2723-2730. Dec. 1, 1984.

Voelker et al., "Variations in the Biosynthesis of Seed-Storage Lipids." Annual Review of Plant Physiology and Plant Molecular Biology, 52. pp. 335-361. Jun. 2001.

Vogel et al., "Cholinephosphotransferase and Diacylglycerol Acyltransferase." Plant Physiology, 110(3). pp. 923-931. 1996.

Wallis et al., "Polyunsaturated fatty acid synthesis: what will they think of next?" Trends in Biochemical Sciences, 27(9). pp. 467-473. Sep. 1, 2002.

Yang et al., "Fatty Acid Composition of Lipids in Sea Buckthorn (*Hippophae rhamnoides* L.) Berries of Different Origins," Journal of Agricultural and Food Chemsitry, 49(4). pp. 1939-1947. Mar. 10, 2001.

Zimmerman et al., "Fat mobilization in adipose tissue is promoted by adipose triglyceride lipase." Science, 306. pp. 1383-1386. Nov. 19, 2004.

Zimmerman et al., "Genevestigator. *Arabidopsis* Microarray Database and Analysis Toolbox." Plant Physiology, 136(1). pp. 2621-2632. Sep. 2004.

Zuo et al., "An estrogen receptor-based transactivator XVE mediates highly inducible gene expression in transgenic plants." The Plant Journal, 24(2). pp. 265-273. Oct. 2000.

Zuo et al., "Chemical-inducible systems for regulated expression of plant genes." Current Opinion in Biotechnology, 11(2). pp. 146-151. Apr. 1, 2000.

Alexandrov N., Publication Site for Issued and Published Sequences (PSIPS) [online], Jul. 2006; United States Patent and Trademark Office, Alexandria VA, USA, [retrieved on Oct. 22, 2013] Retrieved from the Internet:<URL:http://seqdata.uspto.gov/.psipsv?pageRequest=viewSequen- ce&DociD=20060150283&seqiD=104185%2C104186%2CI15424%2C115425>, SEQ ID No. 104185, 104186, 115424, 115425.

*Arabidopsis thaliana* phosphatidic acid phosphatase-related protein (ROD1) mRNA, complete cds, Salanoubat et al., GenBank, pp. 1-2, Apr. 20, 2007. Accession No. NM.sub.--112452.1; Version No. GI:18400909.

AT3G15820 page on the TAIR website (2003).

Atanassova et al., "A 126 bp fragment of a plant histone gene promoter confers preferential expression in meristems of transgenic *Arabidopsis*." The Plant Journal, 2(3). pp. 291-300. May 1992.

Broun et al. "Catalytic Plasticity of Fatty Acid Modification Enzymes Underlying Chemical Diversity of Plant Lipids." Science, 282(5392). pp. 1315-1317. Nov. 13, 1998.

Broun et al. "Genetic Engineering of Plant Lipids." Annual Review of Nutrition, 19. pp. 197-216. Jul. 1999.

Browse et al., "Glycerolipid Synthesis: Biochemistry and Regulation." Annual Review of Plant Physiology and Molecular Biology, 42. pp. 467-506. Jun. 1991.

Cahoon et al., "Biosynthetic origin of conjugated double bonds: Production of fatty acid components of high-value drying oils in transgenic soybean embryos." Proceedings of the National Academy of Sciences, 96(22). pp. 12935-12940. Oct. 26, 1999.

Cases et al., "Cloning of DGAT2, a Second Mammalian Diacylglycerol Acyltransferase, and Related Family Members." The Journal of Biological Chemistry, 276(42). pp. 38870-38876. Oct. 19, 2001 Published ahead of print Jul. 31, 2001.

(56) References Cited

OTHER PUBLICATIONS

Choi et al., "A new approach for the identification and cloning of genes: the pBACwich system using Cre/lox site-specific recombination," Nucleic Acids Research, 28(7). pp. e19i-e19vii. Apr. 1, 2000.
Christensen et al., "Maize polyubiquitin genes: structure, thermal perturbation of expression and transcript splicing, and promoter activity following transfer to protoplasts by electroporation," Plant Molecular Biology, 18(4). pp. 675-689. Feb. 1992.
Christensen et al., "Sequence analysis and transcriptional regulation by heat shock of polyubiquitin transcripts from maize," Plant Molecular Biology, 12(6). pp. 619-632. Jun. 1989.
Cunningham et al., "High-Resolution Epitope Mapping of hGH-Receptor Interactions by Alanine-Scanning Mutagenesis," Science, 244(4908). pp. 1081-1085. Jun. 2, 1989.
Dahlqvist et al, "Phospholipid:diacylglycerol acyltransferase: An enzyme that catalyzes the acyl-CoA-independent formation of triacylglycerol in yeast and plants." Proceedings of the National Academy of Sciences of the United States of America, 97(12). pp. 6487-6492. Jun. 6, 2000.
De Vos et al, "Human Growth Hormone and Extracellular Domain of Its Receptor: Crystal Structure of the Complex." Science, 255(5042). pp. 306-312. Jan. 17, 1992.
Fan et al., "Antisense Suppression of Phospholipase D.alpha. Retards Abscisic Acid-and Ethylene-Promoted Senscence of Postharvest *Arabidopsis* Leaves." The Plant Cell, 9(12). pp. 2183-2196. Dec. 1997.
Funk, "Prostaglandins and Leukotrienes: Advances in Eicosanoid Biology" Science, 294(5548). pp. 1871-1875. Nov. 30, 2001.
Gatz et al., "Promoters that respond to chemical inducers." Trends in Plant Science, 3(9). pp. 352-358. Sep. 1, 1998.
Gatz et al., "Regulation of a modified CaMV 35S promoter by the Tn10-encoded Tet repressor in transgenic tobacco." Molecular & General Genetics, 227(2). pp. 229-237. Jun. 1991.
Goode et al., "Characterization of aminoalcoholphosphotransferases from *Arabidopsis thaliana* and soybean." Plant Physiology and Biochemistry, 37(6). pp. 445-457. Jun. 1999.
Gruber et al. "Vectors for Plant Transformation." Methods in Plant Molecular Biology and Biotechnology, Chapter 7. Glick and Thompson (eds.), CRC Press, Inc., Boca Raton, FL, USA. pp. 89-119. Jun. 1993.
Gunstone, "Movements Towards Tailor-Made Fats." Progress in Lipid Research, 37(5). pp. 277-305. Nov. 1998.
Guo et al., "Functional genomic screen reveals genes involved in lipid-droplet formation and utilization." Nature, 453(7195). pp. 657-661. May 29, 2008. Published ahead of print Apr. 13, 2008.
Harley et al., "Analysis of *E. coli* promoter sequences." Nucleic Acids Research, 15(5). pp. 2343-2361. Mar. 15, 1987.
Heilmann et al., "Identification of the *Arabidopsis* Palmitoyl-Monogalactosyldiacylglycerol .DELTA.7-Desaturase Gene FAD5, and Effects of Plastidial Retargeting of *Arabidopsis* Desaturases on the fad5 Mutant Phenotype." Plant Physiology, 136(4). pp. 4237-4245. Dec. 2004.
Heney et al., "The Purification of Avidin and Its Derivatives on 2-Iminobiotin-6-aminohexyl-Sepharose 4B," Analytical Biochemistry, 114(1). pp. 92-96. Jun. 1981.
Hjelmstad et al., "sn-1,2-diacylglycerol choline- and ethanolaminephosphotransferases in *Saccharomyces cerevisiae*. Mixed micellar analysis of the CPT1 and EPT1 gene products." The Journal of Biological Chemistry, 266. pp. 4357-4365. Mar. 5, 1991.
Huitema et al., "Identification of a family of animal sphingomyelin synthesis." The EMBO Journal, 23(1). pp. 33-44. Jan. 14, 2004. Published ahead of print Dec. 18, 2003.
Jaworski et al., "Industrial oils from transgenic plants." Current Opinion in Plant Biology, 6(2). pp. 178-184. Apr. 2003.

Katagiri et al., "An important role of phosphatidic acid in ABA signaling during germination in *Arabidopsis thaliana*." The Plant Journal, 43(1). pp. 107-117. Jul. 2005. Published ahead of print Jun. 2, 2005.
Kinney et al., "Modifying soybean oil for enhanced performance in biodiesel blends." Fuel Processing Technology, 86(10). pp. 1137-1147. Jun. 25, 2005.
Kumar et al., "A mutation in *Arabidopsis* cytochrome b5 reductase identified by high-throughput screening differentially affects hydroxylation and desaturation," The Plant Journal, 48(6). pp. 920-932. Dec. 2006. Published ahead of print Nov. 17, 2006.
Landry, "DNA Mapping in Plants," Methods in Plant Molecular Biology and Biotechnology, Chapter 17. Glick and Thompson (eds.), CRC Press, Inc., Boca Raton, FL, USA. pp. 269-285. Jun. 1993.
Last et al., "pEmu: an improved promoter for gene expression in cereal cells." Theoretical and Applied Genetics., 81(5). pp. 581-588. May 1991.
Lee et al., "Identification of Non-Heme Diiron Proteins That Catalyze Triple Bond and Expoxy Group Formation." Science, 280(5365). pp. 915-918. May 8, 1998.
Lemieux et al., "Mutants of *Arabidopsis* with alterations in seed lipid fatty acid composition," Theoretical and Applied Genetics, 80(2). pp. 234-240. Aug. 1990.
Lepetit et al., "A plant histone gene promoter can direct both replication-dependent and -independent gene expression in transgenic plants." Molecular Genetics and Genomics, 231(2). pp. 276-285. Jan. 1992.
Lu et al., "A high-throughput screen for genes from castor that boost hydroxyl fatty acid accumulation in seed oils of transgenic *Arabidopsis*." The Plant Journal, 45(5). pp. 847-856. Mar. 2006. Published ahead of print Jan. 27, 2006.
Lu et al., "An enzyme regulating triacylglycerol composition is encoded by the ROD1 gene of *Arabidopsis*," Proceedings of the National Academy of Sciences of the United States of America, 106(44). pp. 18837-18842, 1-8 (supporting information). Nov. 3, 2009. Published ahead of print Oct. 15, 2009.
Lukowitz et al., "Positional Cloning in *Arabidopsis*. Why It Feels Good to Have a Genome Initiative Working for You." Plant Physiology, 123(3). pp. 795-806. Jul. 1, 2000.
Maiti et al., "Promoter/leader deletion analysis and plant expression vectors with the figwort mosaic virus (FMV) full length transcript (FLt) promoter containing single or double enhancer domains," Transgenic Research, 6(2). pp. 143-156. Mar. 1997.
McElroy et al., "Isolation of an Efficient Actin Promoter for Use in Rice Transformation." The Plant Cell, 2(2). pp. 163-171. Feb. 1990.
Mett et al. "Copper-controllable gene expression system for whole plants." Proceedings of the National Academy of the United States of America, 90(10). pp. 4567-4571. May 15, 1993.
Miki et al., "Procedures for 5 Introducing Foreign DNA into Plants." Methods in Plant Molecular Biology and Biotechnology, Chapter 6. Glick and Thompson (eds.), CRC Press Inc., Boca Raton, FL, USA. pp. 67-88. Jun. 1993.
Miquel et al., "*Arabidospsis* Mutants Deficient in Polyunsaturated Fatty Acid Synthesis." The Journal of Biological Chemistry, 267(3). pp. 1502-1509. Jan. 25, 1992.
Morash et al., "Studies Employing *Saccharomyces cerevisiae* cpt1 and ept1 Null Mutants Implicate the CPT1 Gene in Coordinate Regulation of Phospholipid Biosynthesis." The Journal of Biological Chemistry, 269(46). pp. 28769-28776. Nov. 18, 1994.
Mumberg et al., "Yeast vectors for the controlled expression of heteregologous proteins in different genetic backgrounds." Gene, 156. pp. 119-122. 1995.
Muoio et al., "Obesity-Related Derangements in Metabolic Regulation." The Annual Review of Biochemistry, 75. pp. 367-401. Jul. 2006. Published ahead of print Mar. 16, 2006.
Ni et al., "Strength and tissue specificity of chimeric promoters derived from the octopine and mannopine synthase genes." The Plant Journal, 7(4). pp. 661-676. 1995.
NM_112452 (GI:18400909), Genbank, Aug. 20, 2002.

\* cited by examiner

SEQUENCE LISTING

```
<160> NUMBER OF SEQ ID NOS: 30

<210> SEQ ID NO 1
<211> LENGTH: 3961
<212> TYPE: DNA
<213> ORGANISM: Arabidopsis thaliana

<400> SEQUENCE: 1
tattggttta taactttcta cacgtttttt acaaaataaa attataaaag tctcattaaa      60
atagagagat tgtttgagaa attttacaaa attgctaaaa actaattaat aaaattatag     120
aaaacacttt agttataatt tagaatcttt tattttttta ccacctataa ttttatcaaa     180
atcttcaaat ttattgataa attagaaacc aatatatatc acttctttaa tgtattttta     240
tgtcgacaaa tgttttatgt tttatttatc cacacggcca ctttatactt attgtaaatt     300
tataactttg taaaagatgt ctaactacta ccctatacgt gattacgtgt tacaagtttt     360
tttttttttt tttaaattat aataataagt atgaagaaaa gaggaaatag gaaattttgt     420
acgtcgattt ttttttttgt aaaagttgag taaaagtgaa ctaaacatca acgatgtccc     480
aaatcatagc cttgactagt agacaaacac gtctaattgg gtgacgatta gacagaccag     540
tccaattatg tgaaaactaa caaaatcact acctcttgat ttacatttac atttaaatga     600
ttacattcat accaccttt gagtgtgatt gtatgaaatt tacattcttt ggtacaacta      660
aattcagatt tcttttctata atctcttaaa tgtctactat aaatttacaa ataaaaaata    720
aaatggttct aaatatattt aaaatctcaa aatatatgtt ggcatgcaag gaaattcaaa    780
ccaagataat caagaaaaca ggtatagcgt ttcttctacg tcagatatca aatccgtgat    840
```

```
cgagtgaaca atgtcaatat gacaatattc tacaaagaag aaattttgtt tcattcatat    900
ttcttggtaa tgtatcgatt gatcattttg tttcttcctg tttttgtttc tatattgttt    960
aacactacac caatgcttct gctgctttgg atgacgagat agttttttt ttactcgaca    1020
catcatacaa gaccttcgta agtatctgta atacacgaat cattaataca taacacgaat   1080
aatgcattac tatagttttg agaatctcat tctcatactt ctgtctctct tgttgtcgaa   1140
gaatatcaca cttaacatat aaaaagaaca acatgtcagt acacaaaggt aaagcccacc   1200
aaagagagaa aagaaaacaa gacttaacta taacaataaa tttaatgtcg ctctcaaaac   1260
tcatttttt catatgaatt ttctaacaca aacaattttc cttggaaatc tccgccttgt    1320
atctcttata taactcatct ctctatactc cgaacatgtc cctctccgtt aaccttaacg   1380
gccatgtcag ccgccgcagc tgaaaccgac gtctctctcc gtcgcagatc taactctctt   1440
aacggaaacc acactaacgg cgtcgccatt gacggaaccc tagacaacaa caaccgtcgc   1500
gtcggagata caaacactca catgatata tctgctaaga aaactgacaa cggctacgcc    1560
aatggtgtcg gaggaggagg atggagaagc aaagcgtcgt tcacgacgtg gacggcgcgt   1620
gatatcgtct acgtggtgag ataccattgg ataccgtgca tgttcgctgc cggacttctg   1680
ttcttcatgg gcgtggagta cacgcttcag atgattcccg cgagatctga gccgttcgat   1740
cttgggtttg tggtcacgcg ctctttgaat cgcgtattag catcttcacc ggatcttaac   1800
actgttttag ccgcactaaa cacggtatgt cgtgtgagtt aatttaggta aaatatatat   1860
ttaatgatta tcttcaaatt cttattgcct cctttcacct aataatttgt tttttcttc    1920
gtcattcata aatcctaata ttttagtcaa ataaaagtgg ggtagagatg gaaacaaacc   1980
tcagattatt ttcccgtgtt atttaattct ccagctggaa ttttgctgtc aatggtaaca   2040
agcaatgaaa tatcctaagt atagtgagag aaaattagca aagattaat cctaaaatgg    2100
tcataaaaga ttaagaccag ttagtggata aaatggtctt aatcggatta gttagtggac   2160
gaaaacatag ttaatactac aaactctttg ttttagttat gtgatcttct ttttaacaac   2220
tgctttttg tttgtttgta caacacttaa ttaatataga tcgcttttaa ctttagaaaa    2280
gccaataaaa aatgacacat ggtgaagaat gagttggaga cacgatcaca tgcaacacag   2340
agagattggt tacttaaatc taagttttgt acttttaaac taatataatt gggtggggac   2400
aggtgttcgt agggatgcaa acaacgtata ttgtatggac atggttagtg gaaggacgag   2460
cacgagccac catcgcggct ttattcatgt tcacttgtcg cggcattctc ggctactcta   2520
ctcagcttcc tctccctcag gttccaatcc acatatctct ccctctttaa ggataaacca   2580
aatattatta cattagtaac ttcatttct ttttataata ttagtaatga tctaccagta    2640
tatatagatg taacgtcctg tttactggtt ggtccatatc agcagaagtc gaacattttg   2700
gacgtgtgat ttcccttagc cactaccgta tagaaaacag tttataaagg ctccaaataa   2760
tttgttaatc tacaactctc attcaaagta tatttgatta taatagtctt caaatgattt   2820
tatgttttct acctctaaaa aatttcatt taattttcta taaaacgtac ctctaagaaa    2880
actaattggc tacgtatttc tgttaaaatt gactatagtt ttaacataga caattagata   2940
ttttctagtt acagtttaca ttaaaactct aaagatattt taaaaaacaa aatcctctaa   3000
atgaccatat attagtgtga agtgaaagga gtgatagatt gtatatattt tggtcgggag   3060
tgatagattg tgtctaacgc ttttaagttt taacttgccg ggtttaggtt aattttcatc   3120
atcttagtga ttttcttca attatcaggc atcactgttt tccatctttc aaaatagttc    3180
```

-continued

```
cacgatttga ttgaatggac ataaatatca gattgtcact catatacatt ctacggtttc    3240
tagtgactca tctatttact ttctttctcg tgatgtagca tcggtacatg gatttatgtg    3300
tcgttttctt atactattga catgttcaag aaaaaaagta atatcttagg ttaattatct    3360
ctagttcgtg atcaagataa tttaatcccg ggtattacat aactcttttg caggactttc    3420
taggatcagg ggttgatttt ccggtgggaa atgtctcttt cttcctcttc ttctctggcc    3480
atgtcgccgg ctcgatgatc gcatcattgg acatgagaag aatgcagagg ttgagacttg    3540
caatggtctt tgacatcctc aatgtattac agtcgatcag actgctcggt acaagaggac    3600
attacacaat cgaccttgcg gttggagttg gcgctgggat tctcttcgac tcattggccg    3660
gaaagtacga agagatgatg agcaagagac atttaggcac tggttttagt ttgatttcga    3720
aagactctct agtcaattaa atttgttttc tatcagaatg tttagttgag ttgaatctag    3780
cgtaatgaat ttttttgttt ttctttgaaa tggttctact tgactaccgt tatttgaacc    3840
taactaagtg tgatcaatct tatgttaagg ggtattacat agtctatttg aaattcatag    3900
gatctacact atatattcat atatgttccc attagtatag tgaaaaaaat ggttagataa    3960
t                                                                   3961

<210> SEQ ID NO 2
<211> LENGTH: 1207
<212> TYPE: DNA
<213> ORGANISM: Arabidopsis thaliana
<220> FEATURE:
<221> NAME/KEY: CDS
<222> LOCATION: (147)..(1052)

<400> SEQUENCE: 2
aaatttaatg tcgctctcaa aactcatttt tttcatatga attttctaac acaaacaatt     60
ttccttggaa atctccgcct tgtatctctt atataactca tctctctata ctccgaacat    120
gtccctctca gttaaccttc acggcc atg tca gcc gcc gca gct gaa acc gac    173
                              Met Ser Ala Ala Ala Ala Glu Thr Asp
                              1               5 gtc tct ctc cgt cgc aga tct aac tct ctt aac gga aac cac act aac    221
Val Ser Leu Arg Arg Arg Ser Asn Ser Leu Asn Gly Asn His Thr Asn
10              15                  20                  25 ggc gtc gcc att gac gga acc cta gac aac aac aac cgt cgc gtc gga    269
Gly Val Ala Ile Asp Gly Thr Leu Asp Asn Asn Asn Arg Arg Val Gly
            30                  35                  40 gat aca aac act cac atg gat ata tct gct aag aaa act gac aac ggc    317
Asp Thr Asn Thr His Met Asp Ile Ser Ala Lys Lys Thr Asp Asn Gly
        45                  50                  55 tac gcc aat ggt gtc gga gga gga gga tgg aga agc aaa gcg tcg ttc    365
Tyr Ala Asn Gly Val Gly Gly Gly Gly Trp Arg Ser Lys Ala Ser Phe
    60                  65                  70 acg acg tgg acg gcg cgt gat atc gtc tac gtg gtg aga tac cat tgg    413
Thr Thr Trp Thr Ala Arg Asp Ile Val Tyr Val Val Arg Tyr His Trp
75                  80                  85 ata ccg tgc atg ttc gct gcc gga ctt ctg ttc ttc atg ggc gtg gag    461
Ile Pro Cys Met Phe Ala Ala Gly Leu Leu Phe Phe Met Gly Val Glu
90                  95                  100                 105 tac acg ctt cag atg att ccc gcg aga tct gag ccg ttc gat ctt ggg    509
Tyr Thr Leu Gln Met Ile Pro Ala Arg Ser Glu Pro Phe Asp Leu Gly
                110                 115                 120 ttt gtg gtc acg cgc tct ttg aat cgc gta tta gca tct tca ccg gat    557
Phe Val Val Thr Arg Ser Leu Asn Arg Val Leu Ala Ser Ser Pro Asp
            125                 130                 135
```

```
ctt aac act gtt tta gcc gca cta aac acg gtg ttc gta ggg atg caa       605
Leu Asn Thr Val Leu Ala Ala Leu Asn Thr Val Phe Val Gly Met Gln
        140                 145                 150 aca acg tat att gta tgg aca tgg tta gtg gaa gga cga gca cga gcc       653
Thr Thr Tyr Ile Val Trp Thr Trp Leu Val Glu Gly Arg Ala Arg Ala
        155                 160                 165 acc atc gcg gct tta ttc atg ttc act tgt cgc ggc att ctc ggc tac       701
Thr Ile Ala Ala Leu Phe Met Phe Thr Cys Arg Gly Ile Leu Gly Tyr
170                 175                 180                 185 tct act cag ctt cct ctc cct cag gac ttt cta gga tca ggg gtt gat       749
Ser Thr Gln Leu Pro Leu Pro Gln Asp Phe Leu Gly Ser Gly Val Asp
                190                 195                 200 ttt ccg gtg gga aat gtc tct ttc ttc ctc ttc ttc tct ggc cat gtt       797
Phe Pro Val Gly Asn Val Ser Phe Phe Leu Phe Phe Ser Gly His Val
                    205                 210                 215 gcc ggc tcg atg atc gca tca ttg gac atg agg aga atg cag agg ttg       845
Ala Gly Ser Met Ile Ala Ser Leu Asp Met Arg Arg Met Gln Arg Leu
                220                 225                 230 aga ctt gca atg gtc ttt gac atc ctc aat gta tta cag tcg atc aga       893
Arg Leu Ala Met Val Phe Asp Ile Leu Asn Val Leu Gln Ser Ile Arg
235                 240                 245 ctg ctc ggt aca aga gga cat tac aca atc gac ctt gcg gtt gga gtt       941
Leu Leu Gly Thr Arg Gly His Tyr Thr Ile Asp Leu Ala Val Gly Val
250                 255                 260                 265 ggc gct ggg att ctc ttc gac tca ttg gcc gga aag tac gaa gag atg       989
Gly Ala Gly Ile Leu Phe Asp Ser Leu Ala Gly Lys Tyr Glu Glu Met
                    270                 275                 280 atg agc aag aga cac tta ggc act ggt ttt agt ttg att tcg aaa gac      1037
Met Ser Lys Arg His Leu Gly Thr Gly Phe Ser Leu Ile Ser Lys Asp
                285                 290                 295 tct cta gtc aat taa atttgttttc tatcagaatg tttagttgag ttgaatctag      1092
Ser Leu Val Asn
            300 cgtaatgaat ttttttgttt ttctttgaaa tggttctact tgactaccgt tatttgaacc    1152 taactaagtg tgatcaatct tatgttaagg ggtattacat agtctatttg aaatt         1207

<210> SEQ ID NO 3
<211> LENGTH: 301
<212> TYPE: PRT
<213> ORGANISM: Arabidopsis thaliana

<400> SEQUENCE: 3

Met Ser Ala Ala Ala Glu Thr Asp Val Ser Leu Arg Arg Arg Ser
1               5                   10                  15

Asn Ser Leu Asn Gly Asn His Thr Asn Gly Val Ala Ile Asp Gly Thr
                20                  25                  30

Leu Asp Asn Asn Asn Arg Arg Val Gly Asp Thr Asn Thr His Met Asp
            35                  40                  45

Ile Ser Ala Lys Lys Thr Asp Asn Gly Tyr Ala Asn Gly Val Gly Gly
        50                  55                  60

Gly Gly Trp Arg Ser Lys Ala Ser Phe Thr Thr Trp Thr Ala Arg Asp
65                  70                  75                  80

Ile Val Tyr Val Val Arg Tyr His Trp Ile Pro Cys Met Phe Ala Ala
                85                  90                  95

Gly Leu Leu Phe Phe Met Gly Val Glu Tyr Thr Leu Gln Met Ile Pro
                100                 105                 110

Ala Arg Ser Glu Pro Phe Asp Leu Gly Phe Val Val Thr Arg Ser Leu
            115                 120                 125
```

```
Asn Arg Val Leu Ala Ser Ser Pro Asp Leu Asn Thr Val Leu Ala Ala
    130                 135                 140

Leu Asn Thr Val Phe Val Gly Met Gln Thr Thr Tyr Ile Val Trp Thr
145                 150                 155                 160

Trp Leu Val Glu Gly Arg Ala Arg Ala Thr Ile Ala Ala Leu Phe Met
                165                 170                 175

Phe Thr Cys Arg Gly Ile Leu Gly Tyr Ser Thr Gln Leu Pro Leu Pro
            180                 185                 190

Gln Asp Phe Leu Gly Ser Gly Val Asp Phe Pro Val Gly Asn Val Ser
        195                 200                 205

Phe Phe Leu Phe Phe Ser Gly His Val Ala Gly Ser Met Ile Ala Ser
210                 215                 220

Leu Asp Met Arg Arg Met Gln Arg Leu Arg Leu Ala Met Val Phe Asp
225                 230                 235                 240

Ile Leu Asn Val Leu Gln Ser Ile Arg Leu Leu Gly Thr Arg Gly His
                245                 250                 255

Tyr Thr Ile Asp Leu Ala Val Gly Val Gly Ala Gly Ile Leu Phe Asp
            260                 265                 270

Ser Leu Ala Gly Lys Tyr Glu Glu Met Met Ser Lys Arg His Leu Gly
        275                 280                 285

Thr Gly Phe Ser Leu Ile Ser Lys Asp Ser Leu Val Asn
290                 295                 300

<210> SEQ ID NO 4
<211> LENGTH: 1207
<212> TYPE: DNA
<213> ORGANISM: Arabidopsis thaliana
<220> FEATURE:
<221> NAME/KEY: CDS
<222> LOCATION: (147)..(371)

<400> SEQUENCE: 4
aaatttaatg tcgctctcaa aactcatttt tttcatatga attttctaac acaaacaatt      60
ttccttggaa atctccgcct tgtatctctt atataactca tctctctata ctccgaacat     120
gtccctctca gttaacctta acggcc atg tca gcc gcc gca gct gaa acc gac     173
                             Met Ser Ala Ala Ala Ala Glu Thr Asp
                               1               5 gtc tct ctc cgt cgc aga tct aac tct ctt aac gga aac cac act aac     221
Val Ser Leu Arg Arg Arg Ser Asn Ser Leu Asn Gly Asn His Thr Asn
 10                  15                  20                  25 ggc gtc gcc att gac gga acc cta gac aac aac aac cgt cgc gtc gga     269
Gly Val Ala Ile Asp Gly Thr Leu Asp Asn Asn Asn Arg Arg Val Gly
                 30                  35                  40 gat aca aac act cac atg gat ata tct gct aag aaa act gac aac ggc     317
Asp Thr Asn Thr His Met Asp Ile Ser Ala Lys Lys Thr Asp Asn Gly
             45                  50                  55 tac gcc aat ggt gtc gga gga gga gga tgg aga agc aaa gcg tcg ttc     365
Tyr Ala Asn Gly Val Gly Gly Gly Gly Trp Arg Ser Lys Ala Ser Phe
         60                  65                  70 acg acg tgaacggcgc gtgatatcgt ctacgtggtg agataccatt ggataccgtg     421
Thr Thr
 75 catgttcgct gccggacttc tgttcttcat gggcgtggag tacacgcttc agatgattcc     481 cgcgagatct gagccgttcg atcttgggtt tgtggtcacg cgctctttga atcgcgtatt     541 agcatcttca ccggatctta acactgtttt agccgcacta acacggtgt tcgtagggat     601
```

```
gcaaacaacg tatattgtat ggacatggtt agtggaagga cgagcacgag ccaccatcgc    661
ggctttattc atgttcactt gtcgcggcat tctcggctac tctactcagc ttcctctccc    721
tcaggacttt ctaggatcag gggttgattt tccggtggga aatgtctctt tcttcctctt    781
cttctctggc catgttgccg gctcgatgat cgcatcattg acatgagga gaatgcagag    841 gttgagactt gcaatggtct tgacatcct caatgtatta cagtcgatca gactgctcgg    901
tacaagagga cattacacaa tcgaccttgc ggttggagtt ggcgctggga ttctcttcga    961
ctcattggcc ggaaagtacg aagagatgat gagcaagaga cacttaggca ctggttttag    1021
tttgatttcg aaagactctc tagtcaatta aatttgtttt ctatcagaat gtttagttga    1081
gttgaatcta gcgtaatgaa ttttttttgtt tttctttgaa atggttctac ttgactaccg    1141
ttatttgaac ctaactaagt gtgatcaatc ttatgttaag gggtattaca tagtctattt    1201
gaaatt                                                                1207
```

<210> SEQ ID NO 5
<211> LENGTH: 75
<212> TYPE: PRT
<213> ORGANISM: Arabidopsis thaliana

<400> SEQUENCE: 5

```
Met Ser Ala Ala Ala Glu Thr Asp Val Ser Leu Arg Arg Arg Ser
1               5                   10                  15

Asn Ser Leu Asn Gly Asn His Thr Asn Gly Val Ala Ile Asp Gly Thr
            20                  25                  30

Leu Asp Asn Asn Arg Arg Val Gly Asp Thr Asn Thr His Met Asp
        35                  40                  45

Ile Ser Ala Lys Lys Thr Asp Asn Gly Tyr Ala Asn Gly Val Gly Gly
    50                  55                  60

Gly Gly Trp Arg Ser Lys Ala Ser Phe Thr Thr
65                  70                  75
```

<210> SEQ ID NO 6
<211> LENGTH: 843
<212> TYPE: DNA
<213> ORGANISM: Brassica rapa

<400> SEQUENCE: 6

```
atgtcaacta taccgtcgt ccctctccgt cgcagatcta acggatatca cactaacggc      60
gtggccttta acggaatgga gaacattgtc aagaaaaccg acgactgcta caccaacggc    120
aacggaggag tagagagaag caaagcctcg tttctgacat ggaccatgcg tgacgctgtc    180
tacgtagcga gataccattg gataccgtgt tctttgcgg tcggagttct gttctttatg    240
ggggttgagt acacgctcca gatggttccg gcgaagtctg agccgttcga tattgggttt    300
gtggccacgc gctctctgaa ccgcgtcttg gcgagttcac cggatcttaa caccctttta    360
gcggctctaa acacggtatt cgtagcgatg cagacgacgt atattgtatg acatggttg    420 atggaaggaa gaccacgagc cactatctcg gcttgcttca tgtttacttg tcgcggcatt    480
cttggttact ctactcagct ccctctacca caggattttt taggatcagg agttgatttt    540
ccggtgggaa acgtctcatt cttcctcttc tattctggcc acgtagccgg ttcaatgatc    600
gcatccttgg acatgaggag aatgcagagg ttgagactag cgatgctttt tgacatcctc    660
aacatattac aatcgatcag actgctcggg acgagaggac actacacgat cgatcttgcg    720
gtcggagttg gcgctgggat tctcttgac tcattggccg ggaagtacga agagatgatg    780
```

```
agcaagagac acaatttagc caatggtttt agtttgattt ctaaagactc gctagtcaat    840
taa                                                                  843
```

<210> SEQ ID NO 7
<211> LENGTH: 280
<212> TYPE: PRT
<213> ORGANISM: Brassica rapa

<400> SEQUENCE: 7

```
Met Ser Thr Asn Thr Val Val Pro Leu Arg Arg Arg Ser Asn Gly Tyr
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Gly Val Glu Arg Ser Lys
        35                  40                  45

Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Gln Arg Leu Arg Leu Ala Met Leu Phe Asp Ile Leu Asn Ile Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280
```

<210> SEQ ID NO 8
<211> LENGTH: 858
<212> TYPE: DNA
<213> ORGANISM: Ricinus communis

<400> SEQUENCE: 8

```
atgaaatcca ccgtccctcc caccaccaca accacaacca caactactct ttacaagcgc    60
aagaaagaca tcaacttgac ctccgtcaac gacagtgttg acatggttag caacaagaac   120
tttgctaacg gtaatgttaa tggtggtggg ggctacactg cttttaatag gtttgaccca   180
```

```
tcgttcatga aatggacgac tcatgatgtg gtcaatgtag tcaagtttca ttggttaccg    240 tgtgttttttg gacttgggtt gctattcttt atggccgttg aatacactct tcgcatggtt    300
ccggcttctt ctccgccttt tgatttgggg tttctggtta cgcgccacct tcatctcttg    360 cttttcttctt ggccggcgct caacactttg ttggcttttc ttaatacggt gtttgttttg    420
atgcaaaccg catatatatt gtggacgtgg ctaatagagg gcagaccaag agctacaatt    480
tcggctttat tcatgttcac ttgccgtggg attcttggct actccactca gcttccactt    540
cctgagggat ttctgggatc aggagttgat tttccagtag gaaatgtgtc attcttcctg    600 ttttttctccg gccatgtcgc ggggtctgtg atagcatcgc tcgatatgag aagaatgcag    660
agatgggaat tggcatggac atatgatgtg cttaatgttc tacaagctgt gaggctacta    720
ggcactagag gccactatac aatcgactta gcaactggtg taggtgctgg cattctgttt    780
gattcacttg cggggaaata tgaagagagc aagagaaaac aggctgttgt tgctaaagag    840
tcttctttgt ttagttaa                                                  858
```

<210> SEQ ID NO 9
<211> LENGTH: 285
<212> TYPE: PRT
<213> ORGANISM: Ricinus communis

<400> SEQUENCE: 9

```
Met Lys Ser Thr Val Pro Pro Thr Thr Thr Thr Thr Thr Thr Thr Thr
1               5                   10                  15

Leu Tyr Lys Arg Lys Lys Asp Ile Asn Leu Thr Ser Val Asn Asp Ser
            20                  25                  30

Val Asp Met Val Ser Asn Lys Asn Phe Ala Asn Gly Asn Val Asn Gly
        35                  40                  45

Gly Gly Gly Tyr Thr Ala Phe Asn Arg Phe Asp Pro Ser Phe Met Lys
    50                  55                  60

Trp Thr Thr His Asp Val Val Asn Val Val Lys Phe His Trp Leu Pro
65                  70                  75                  80

Cys Val Phe Gly Leu Gly Leu Leu Phe Met Ala Val Glu Tyr Thr
                85                  90                  95

Leu Arg Met Val Pro Ala Ser Ser Pro Pro Phe Asp Leu Gly Phe Leu
            100                 105                 110

Val Thr Arg His Leu His Leu Leu Ser Ser Trp Pro Ala Leu Asn
        115                 120                 125

Thr Leu Leu Ala Phe Leu Asn Thr Val Phe Val Leu Met Gln Thr Ala
    130                 135                 140

Tyr Ile Leu Trp Thr Trp Leu Ile Glu Gly Arg Pro Arg Ala Thr Ile
145                 150                 155                 160

Ser Ala Leu Phe Met Phe Thr Cys Arg Gly Ile Leu Gly Tyr Ser Thr
                165                 170                 175

Gln Leu Pro Leu Pro Glu Gly Phe Leu Gly Ser Gly Val Asp Phe Pro
            180                 185                 190

Val Gly Asn Val Ser Phe Phe Leu Phe Phe Ser Gly His Val Ala Gly
        195                 200                 205

Ser Val Ile Ala Ser Leu Asp Met Arg Arg Met Gln Arg Trp Glu Leu
    210                 215                 220

Ala Trp Thr Tyr Asp Val Leu Asn Val Leu Gln Ala Val Arg Leu Leu
225                 230                 235                 240

Gly Thr Arg Gly His Tyr Thr Ile Asp Leu Ala Thr Gly Val Gly Ala
```

```
                        245                 250                 255
Gly Ile Leu Phe Asp Ser Leu Ala Gly Lys Tyr Glu Glu Ser Lys Arg
                260                 265                 270

Lys Gln Ala Val Val Ala Lys Glu Ser Ser Leu Phe Ser
        275                 280                 285

<210> SEQ ID NO 10
<211> LENGTH: 924
<212> TYPE: DNA
<213> ORGANISM: Oryza sativa

<400> SEQUENCE: 10
atgccgccgc cgccgccgcc cagcctcacg gccaacaccg catcctccat gggcaacgcc    60
gaggccgtcg tggtgctgcc cgcgaacggc ggcgcgcggc ggcgcgccga caaggtcgtc   120
cacccggcgc cgatgccgga cagagcagct ggtggcgcga tggagaggga aggcggcggc   180
gtcggcggcg gcggcgaggt gggtgggtgg aggaggccgg agtggtgctc ggcggcgggg   240
gtggcggggg tcctgcggcg caccccggcg gcggcggcgt tcgggtgcgg gctgctgctg   300
ttcatggccg tggagtacac catccccatg gtgccgcccg ccgcgccgcc ggtcgacctc   360
ggcttcgccg ccaccgccgc gctccacgcc gggatcgccg cccgcccatg gctcaactcg   420
ctcctcgccg cgctcaacac ggtgttcgtg gcgatgcagg cggcgtacat cctgtgggcg   480
atcctcggcg agggccggcc gcgcgccgcc gtggcggcga tgatgatgtt cacctgccgc   540
ggcgcgctcg gctgcgccac gcagctgccg ctgccggccg agttcctggg ctccggcatg   600
gacttccccg tcggcaacgt ctccttcttc ctcttcttct ccggccacgt cgccggcgcg   660
gtgatcgccg ccgaggacat cgccgcgcg  gggcgccgcg gcatggcgcg cctctacgac   720
gcgctcaacc tgctccaggg cgtcaggctg ctcgcctgca ggggccacta ccaccatcgac   780 ctcgccgtcg gcgtcggcgc cggcctcctc ttcgacatgc tcgccggcag gtacctggac   840
ggcaagaaca ccgtcgacgg cggcgccgcc gtggcgccgg ggagccggtg ctgcagctgc   900
cacaaggctc tcttgtcaca gtag                                          924

<210> SEQ ID NO 11
<211> LENGTH: 307
<212> TYPE: PRT
<213> ORGANISM: Oryza sativa

<400> SEQUENCE: 11

Met Pro Pro Pro Pro Pro Ser Leu Thr Ala Asn Thr Ala Ser Ser
1               5                   10                  15

Met Gly Asn Ala Glu Ala Val Val Leu Pro Ala Asn Gly Gly Ala
                20                  25                  30

Arg Arg Arg Ala Asp Lys Val Val His Pro Ala Pro Met Pro Asp Arg
            35                  40                  45

Ala Ala Gly Gly Ala Met Glu Arg Glu Gly Gly Val Gly Gly Gly
        50                  55                  60

Gly Glu Val Gly Gly Trp Arg Arg Pro Glu Trp Cys Ser Ala Ala Gly
65                  70                  75                  80

Val Ala Gly Val Leu Arg Arg His Pro Ala Ala Ala Phe Gly Cys
                85                  90                  95

Gly Leu Leu Leu Phe Met Ala Val Glu Tyr Thr Ile Pro Met Val Pro
            100                 105                 110

Pro Ala Ala Pro Pro Val Asp Leu Gly Phe Ala Ala Thr Ala Ala Leu
            115                 120                 125
```

His Ala Gly Ile Ala Ala Arg Pro Trp Leu Asn Ser Leu Leu Ala Ala
    130                 135                 140

Leu Asn Thr Val Phe Val Ala Met Gln Ala Ala Tyr Ile Leu Trp Ala
145                 150                 155                 160

Ile Leu Gly Glu Gly Arg Pro Arg Ala Ala Val Ala Ala Met Met Met
                165                 170                 175

Phe Thr Cys Arg Gly Ala Leu Gly Cys Ala Thr Gln Leu Pro Leu Pro
            180                 185                 190

Ala Glu Phe Leu Gly Ser Gly Met Asp Phe Pro Val Gly Asn Val Ser
        195                 200                 205

Phe Phe Leu Phe Phe Ser Gly His Val Ala Gly Ala Val Ile Ala Ala
    210                 215                 220

Glu Asp Met Arg Arg Ala Gly Arg Arg Gly Met Ala Arg Leu Tyr Asp
225                 230                 235                 240

Ala Leu Asn Leu Leu Gln Gly Val Arg Leu Leu Ala Cys Arg Gly His
                245                 250                 255

Tyr Thr Ile Asp Leu Ala Val Gly Val Gly Ala Gly Leu Leu Phe Asp
            260                 265                 270

Met Leu Ala Gly Arg Tyr Leu Asp Gly Lys Asn Thr Val Asp Gly Gly
        275                 280                 285

Ala Ala Val Ala Pro Gly Ser Arg Cys Cys Ser Cys His Lys Ala Leu
    290                 295                 300

Leu Ser Gln
305

<210> SEQ ID NO 12
<211> LENGTH: 729
<212> TYPE: DNA
<213> ORGANISM: Vitis vinifera

<400> SEQUENCE: 12
atgaagcaga agaagaagac tgccaatggg ttttggagca agcttcgtt catgaactgg      60 tcgatggacg acgcggttgg cctcttccgg tttcatccga tgccgtgcgt tttcgctgtg    120
tcgttgttgt ttttcatggg cgtggagtac actctccgga tggtgccatc gtcgtcgccg    180
ccgttcgatc tggggttcgt cgccaccgag tggctccacc gaattctcgc ttcgagcccc    240
gatctcaata ctcttctggc cggactcaac acggtgtttg tggggatgca aaccacatat    300 ataaatttgga cgtggatggt ggagggaagg cctcgggcca ccatttctgc gcttttcatg    360
tttacctgca gagggattct tggctactcc acacagcttc ctgttcctca gggattttg     420 ggctcaggcg tggacttccc agtcggtaat gtgtccttct tcctcttctt ctcgggccat    480
gttgcagggt ctgtaattgc atccttagac atgaggagaa tgaagaggtg gggaatggca    540
tggacatttg acgtgctcaa tattctacaa ggtgtaaggc tcctggggac tagggggccac   600 tataccatcg acttggccgt gggcataggc gccggagttt tatttgattc tctggccgga    660
aagtatgagg agggcaagag aagagcagct gcctctactg caaatggtaa cgctgatgtg    720
tttacataa                                                             729

<210> SEQ ID NO 13
<211> LENGTH: 242
<212> TYPE: PRT
<213> ORGANISM: Vitis vinifera

<400> SEQUENCE: 13

Met Lys Gln Lys Lys Lys Thr Ala Asn Gly Phe Trp Ser Lys Ala Ser
1               5                   10                  15

Phe Met Asn Trp Ser Met Asp Asp Ala Val Gly Leu Phe Arg Phe His
            20                  25                  30

Pro Met Pro Cys Val Phe Ala Val Ser Leu Leu Phe Phe Met Gly Val
            35                  40                  45

Glu Tyr Thr Leu Arg Met Val Pro Ser Ser Ser Pro Pro Phe Asp Leu
50                  55                  60

Gly Phe Val Ala Thr Glu Trp Leu His Arg Ile Leu Ala Ser Ser Pro
65                  70                  75                  80

Asp Leu Asn Thr Leu Leu Ala Gly Leu Asn Thr Val Phe Val Gly Met
                85                  90                  95

Gln Thr Thr Tyr Ile Ile Trp Thr Trp Met Val Glu Gly Arg Pro Arg
            100                 105                 110

Ala Thr Ile Ser Ala Leu Phe Met Phe Thr Cys Arg Gly Ile Leu Gly
            115                 120                 125

Tyr Ser Thr Gln Leu Pro Val Pro Gln Gly Phe Leu Gly Ser Gly Val
130                 135                 140

Asp Phe Pro Val Gly Asn Val Ser Phe Leu Phe Phe Ser Gly His
145                 150                 155                 160

Val Ala Gly Ser Val Ile Ala Ser Leu Asp Met Arg Arg Met Lys Arg
                165                 170                 175

Trp Gly Met Ala Trp Thr Phe Asp Val Leu Asn Ile Leu Gln Gly Val
            180                 185                 190

Arg Leu Leu Gly Thr Arg Gly His Tyr Thr Ile Asp Leu Ala Val Gly
            195                 200                 205

Ile Gly Ala Gly Val Leu Phe Asp Ser Leu Ala Gly Lys Tyr Glu Glu
210                 215                 220

Gly Lys Arg Arg Ala Ala Ser Thr Ala Asn Gly Asn Ala Asp Val
225                 230                 235                 240

Phe Thr

<210> SEQ ID NO 14
<211> LENGTH: 894
<212> TYPE: DNA
<213> ORGANISM: Picea sitchensis

<400> SEQUENCE: 14
atgtcgtgca ggagaagaag ttcagaggat aatgggggtg agacagacat gatttatgtt      60
gacaggagaa cgaaacagtg cctgggaaac ttgttttgta tatgttcaca agagatccag     120
agaaagctga gggatttaat gggagcaaat gggaatgtgg tccatcagga tgagaaatct     180
ccgttcccat taggtgatac tgctgtgtat ccatccttta tggggtggtc tatgacatat     240
ctgattggaa ctgcgaggtt ccatccgctg cctgttttgt tggttggttg tctgctattt     300
ttcatggcag tggagtatac tctggtcatg gtacctgctg gctctcaacc atatgatgtg     360
ggtttcgtct ggacacagag tctccatgat ttattgctgg agagacctgc attgaatacg     420
gttttagcag caatgaatac ggttttttgtg ggtatgcaaa ccttttacat cttatggact     480
tgtgttgtgg agggaagggg gcggcctaca attgctgcac ttttcatgtt cacatgcaga     540
ggcatattgg gctacacaac tcaactccct taccggagg aatttctggg atcaggagtg     600
gattttccag ttgggaacgt gtcctttttc ctgtttttt caggacatgt ggcaggcgca     660
gtgattgctt ctcttgacat gagacgtgtg aagaggaacc agctggcatt tactttgac      720 actttgaatg cccttcaatc agtgcgtttg cttggcacaa gaggtcatta tacaattgat    780
ctggtagcgg gggtaggtgc aggctggctg tttgattcct tagctggcaa gtacgaggaa    840
agtaaaagaa gtactgttca aaaagatttg gtatttgaac cattgatagg ttag          894

<210> SEQ ID NO 15
<211> LENGTH: 297
<212> TYPE: PRT
<213> ORGANISM: Picea sitchensis

<400> SEQUENCE: 15

Met Ser Cys Arg Arg Ser Ser Glu Asp Asn Gly Gly Glu Thr Asp
1               5                   10                  15

Met Ile Tyr Val Asp Arg Arg Thr Lys Gln Cys Leu Gly Asn Leu Phe
            20                  25                  30

Cys Ile Cys Ser Gln Glu Ile Gln Arg Lys Leu Arg Asp Leu Met Gly
        35                  40                  45

Ala Asn Gly Asn Val Val His Gln Asp Glu Lys Ser Pro Phe Pro Leu
    50                  55                  60

Gly Asp Thr Ala Val Tyr Pro Ser Phe Met Gly Trp Ser Met Thr Tyr
65                  70                  75                  80

Leu Ile Gly Thr Ala Arg Phe His Pro Leu Pro Val Leu Leu Val Gly
                85                  90                  95

Cys Leu Leu Phe Phe Met Ala Val Glu Tyr Thr Leu Val Met Val Pro
            100                 105                 110

Ala Gly Ser Gln Pro Tyr Asp Val Gly Phe Val Trp Thr Gln Ser Leu
        115                 120                 125

His Asp Leu Leu Leu Glu Arg Pro Ala Leu Asn Thr Val Leu Ala Ala
    130                 135                 140

Met Asn Thr Val Phe Val Gly Met Gln Thr Phe Tyr Ile Leu Trp Thr
145                 150                 155                 160

Cys Val Val Glu Gly Arg Gly Arg Pro Thr Ile Ala Ala Leu Phe Met
                165                 170                 175

Phe Thr Cys Arg Gly Ile Leu Gly Tyr Thr Thr Gln Leu Pro Leu Pro
            180                 185                 190

Glu Glu Phe Leu Gly Ser Gly Val Asp Phe Pro Val Gly Asn Val Ser
        195                 200                 205

Phe Phe Leu Phe Phe Ser Gly His Val Ala Gly Ala Val Ile Ala Ser
    210                 215                 220

Leu Asp Met Arg Arg Val Lys Arg Asn Gln Leu Ala Phe Thr Phe Asp
225                 230                 235                 240

Thr Leu Asn Ala Leu Gln Ser Val Arg Leu Leu Gly Thr Arg Gly His
                245                 250                 255

Tyr Thr Ile Asp Leu Val Ala Gly Val Gly Ala Gly Trp Leu Phe Asp
            260                 265                 270

Ser Leu Ala Gly Lys Tyr Glu Glu Ser Lys Arg Ser Thr Val Gln Lys
        275                 280                 285

Asp Leu Val Phe Glu Pro Leu Ile Gly
    290                 295

<210> SEQ ID NO 16
<211> LENGTH: 738
<212> TYPE: DNA
<213> ORGANISM: Physcomitrella patens

<400> SEQUENCE: 16

```
atggacacat ccaagaaatg gtccaaaggc aataagagaa tctcacctgt atttctaagg      60
tggagaccag cggaggcatg gcacatcgtt cgagcgcatc catggctcat gttttttgttt   120
atcaattttg cattggtgat accgcttgag tacaacatta gtatgataga gcctaggggt    180
gaaccctatg atgctggttt tgtgattact aagaggattc acaacatctt agaactgaga    240
cccaccttga atcatgtcct tgctgccgcg aatacggctc tggtggtatt ccaaatagtg    300
tacatcgcgt gggcgtgggt agtcgagggc cgattccgtc ccgttcttgc gtcggcgttc    360
atgttcagta gccgcggcat ccttggctac tccacccaac tccctgttcc ccaggagttt    420
ctgggatctg gggtagactt tccagttgga catgtttctt ttttttctatt cttctcgggg   480
catgtgggag cctccattat tgctaccttg gatttacgat gtgtgaatcg ggtacgggga    540
gctctagtga tggatatgtt gaatgtactg cagacgatgc gactgctagc cacacggggt    600
cattcactta ttgaccttgt tagtggagct tttgcagggt gggcttgtta ccacttggct    660
ggcttgtgcg aagagaggat caagacccag tcttccagtg tcgcaggggt ttctgattat    720
attgatttga atctctag                                                   738

<210> SEQ ID NO 17
<211> LENGTH: 245
<212> TYPE: PRT
<213> ORGANISM: Physcomitrella patens

<400> SEQUENCE: 17

Met Asp Thr Ser Lys Lys Trp Ser Lys Gly Asn Lys Arg Ile Ser Pro
1               5                   10                  15

Val Phe Leu Arg Trp Arg Pro Ala Glu Ala Trp His Ile Val Arg Ala
            20                  25                  30

His Pro Trp Leu Met Phe Leu Phe Ile Asn Phe Ala Leu Val Ile Pro
        35                  40                  45

Leu Glu Tyr Asn Ile Ser Met Ile Glu Pro Arg Gly Glu Pro Tyr Asp
    50                  55                  60

Ala Gly Phe Val Ile Thr Lys Arg Ile His Asn Ile Leu Glu Leu Arg
65                  70                  75                  80

Pro Thr Leu Asn His Val Leu Ala Ala Ala Asn Thr Ala Leu Val Val
                85                  90                  95

Phe Gln Ile Val Tyr Ile Ala Trp Ala Trp Val Val Glu Gly Arg Phe
            100                 105                 110

Arg Pro Val Leu Ala Ser Ala Phe Met Phe Ser Ser Arg Gly Ile Leu
        115                 120                 125

Gly Tyr Ser Thr Gln Leu Pro Val Pro Gln Glu Phe Leu Gly Ser Gly
    130                 135                 140

Val Asp Phe Pro Val Gly His Val Ser Phe Phe Leu Phe Phe Ser Gly
145                 150                 155                 160

His Val Gly Ala Ser Ile Ile Ala Thr Leu Asp Leu Arg Cys Val Asn
                165                 170                 175

Arg Val Arg Gly Ala Leu Val Met Asp Met Leu Asn Val Leu Gln Thr
            180                 185                 190

Met Arg Leu Leu Ala Thr Arg Gly His Tyr Thr Ile Asp Leu Val Ser
        195                 200                 205

Gly Ala Phe Ala Gly Trp Ala Cys Tyr His Leu Ala Gly Leu Cys Glu
    210                 215                 220

Glu Arg Ile Lys Thr Gln Ser Ser Ser Val Ala Gly Val Ser Asp Tyr
225                 230                 235                 240
```

Ile Asp Leu Asn Leu
              245

<210> SEQ ID NO 18
<211> LENGTH: 906
<212> TYPE: DNA
<213> ORGANISM: Arabidopsis thaliana

<400> SEQUENCE: 18

| | |
|---|---:|
| atgtcagccg ccgcagctga aaccgacgtc tctctccgtc gcagatctaa ctctcttaac | 60 |
| ggaaaccaca ctaacggcgt cgccattgac ggaaccctag acaacaacaa ccgtcgcgtc | 120 |
| ggagatacaa acactcacat ggatatatct gctaagaaaa ctgacaacgg ctacgccaat | 180 |
| ggtgtcggag gaggaggatg gagaagcaaa gcgtcgttca cgacgtggac ggcgcgtgat | 240 |
| atcgtctacg tggtgagata ccattggata ccgtgcatgt tcgctgccgg acttctgttc | 300 |
| ttcatgggcg tggagtacac gcttcagatg attcccgcga gatctgagcc gttcgatctt | 360 |
| gggtttgtgg tcacgcgctc tttgaatcgc gtattagcat cttcaccgga tcttaacact | 420 |
| gttttagccg cactaaacac ggtgttcgta gggatgcaaa caacgtatat tgtatggaca | 480 |
| tggttagtga aggacgagc acgagccacc atcgcggctt tattcatgtt cacttgtcgc | 540 |
| ggcattctcg gctactctac tcagcttcct ctccctcagg actttctagg atcaggggtt | 600 |
| gattttccgg tggaaatgt ctctttcttc ctcttcttct ctggccatgt cgccggctcg | 660 |
| atgatcgcat cattggacat gagaagaatg cagaggttga gacttgcaat ggtctttgac | 720 |
| atcctcaatg tattacagtc gatcagactg ctcggtacaa gaggacatta cacaatcgac | 780 |
| cttgcggttg gagttggcgc tgggattctc ttcgactcat tggccggaaa gtacgaagag | 840 |
| atgatgagca agagacattt aggcactggt tttagtttga tttcgaaaga ctctctagtc | 900 |
| aattaa | 906 |

<210> SEQ ID NO 19
<211> LENGTH: 849
<212> TYPE: DNA
<213> ORGANISM: Brassica napus

<400> SEQUENCE: 19

| | |
|---|---:|
| atgtcaacta ataccgtcgt ccctctccgt cgcagatcta acggatatca cactaacggc | 60 |
| gtggcccttta acggaatgga taatattgtc aagaaaaccg acgactgcta caccaacggc | 120 |
| aacggcaacg gaggagtaga gagaagcaaa gcctcgtttc tgacatggac catgcgtgac | 180 |
| gctgtctacg tagcgagata ccattggata ccgtgttct ttgcggtcgg agttctgttc | 240 |
| tttatggggg ttgagtacac gctccagatg gttccggcga agtctgagcc gttcgatatt | 300 |
| gggtttgtgg ccacgcgctc tctaaaccgc gtcttggcga gttcaccgga tcttaacacc | 360 |
| cttttagcgg ctctaaacac ggtattcgta gcgatgcaaa cgacgtatat tgtatggaca | 420 |
| tggttgatga aggaagacc acgagccact atctcggctt gcttcatgtt tacttgtcgc | 480 |
| ggcattcttg gttactctac tcagctccct ctaccacagg atttttagg atcaggagtt | 540 |
| gattttccgg tggaaacgt ctcattcttc ctcttctatt ctggccacgt agccggttca | 600 |
| atgatcgcat ccttggacat gaggagaatg cagaggttga gactagcgat gcttttgac | 660 |
| atcctcaaca tattacaatc gatcagactg ctcgggacga gaggacacta cacgatcgat | 720 |
| cttgcggtcg gagttggcgc tgggattctc tttgactcat tggccgggaa gtacgaagag | 780 |
| atgatgagca agagacacaa tttagccaat ggttttagtt tgatttctaa agactcgcta | 840 | gtcaattaa                                                                 849

<210> SEQ ID NO 20
<211> LENGTH: 282
<212> TYPE: PRT
<213> ORGANISM: Brassica napus

<400> SEQUENCE: 20

Met Ser Thr Asn Thr Val Val Pro Leu Arg Arg Ser Asn Gly Tyr
1               5                   10                  15

His Thr Asn Gly Val Ala Phe Asn Gly Met Asp Asn Ile Val Lys Lys
            20                  25                  30

Thr Asp Asp Cys Tyr Thr Asn Gly Asn Gly Val Glu Arg
        35                  40                  45

Ser Lys Ala Ser Phe Leu Thr Trp Thr Met Arg Asp Ala Val Tyr Val
50                  55                  60

Ala Arg Tyr His Trp Ile Pro Cys Phe Phe Ala Val Gly Val Leu Phe
65              70                  75                  80

Phe Met Gly Val Glu Tyr Thr Leu Gln Met Val Pro Ala Lys Ser Glu
                85                  90                  95

Pro Phe Asp Ile Gly Phe Val Ala Thr Arg Ser Leu Asn Arg Val Leu
            100                 105                 110

Ala Ser Ser Pro Asp Leu Asn Thr Leu Leu Ala Ala Leu Asn Thr Val
        115                 120                 125

Phe Val Ala Met Gln Thr Thr Tyr Ile Val Trp Thr Trp Leu Met Glu
130                 135                 140

Gly Arg Pro Arg Ala Thr Ile Ser Ala Cys Phe Met Phe Thr Cys Arg
145                 150                 155                 160

Gly Ile Leu Gly Tyr Ser Thr Gln Leu Pro Leu Pro Gln Asp Phe Leu
                165                 170                 175

Gly Ser Gly Val Asp Phe Pro Val Gly Asn Val Ser Phe Phe Leu Phe
            180                 185                 190

Tyr Ser Gly His Val Ala Gly Ser Met Ile Ala Ser Leu Asp Met Arg
        195                 200                 205

Arg Met Gln Arg Leu Arg Leu Ala Met Leu Phe Asp Ile Leu Asn Ile
210                 215                 220

Leu Gln Ser Ile Arg Leu Leu Gly Thr Arg Gly His Tyr Thr Ile Asp
225                 230                 235                 240

Leu Ala Val Gly Val Gly Ala Gly Ile Leu Phe Asp Ser Leu Ala Gly
                245                 250                 255

Lys Tyr Glu Glu Met Met Ser Lys Arg His Asn Leu Ala Asn Gly Phe
            260                 265                 270

Ser Leu Ile Ser Lys Asp Ser Leu Val Asn
        275                 280

<210> SEQ ID NO 21
<211> LENGTH: 849
<212> TYPE: DNA
<213> ORGANISM: Brassica rapa

<400> SEQUENCE: 21
atgtcaacta ataccgtcgt ccctctccgt cgcagatcta acggatatca cactaacggc    60
gtggccttta acggaatgga gaacattgtc aagaaaaccg acgactgcta caccaacggc   120
aacggcaacg gaggagtaga gagaagcaaa gcctcgtttc tgacatggac catgcgtgac   180
gctgtctacg tagcgagata ccattggata ccgtgtttct ttgcggtcgg agttctgttc   240

```
tttatggggg ttgagtacac gctccagatg gttccggcga agtctgagcc gttcgatatt      300
gggtttgtgg ccacgcgctc tctgaaccgc gtcttggcga gttcaccgga tcttaacacc      360
cttttagcgg ctctaaacac ggtattcgta gcgatgcaga cgacgtatat tgtatggaca      420
tggttgatgg aaggaagacc acgagccact atctcggctt gcttcatgtt tacttgtcgc      480
ggcattcttg gttactctac tcagctccct ctaccacagg attttttagg atcaggagtt      540
gattttccgg tgggaaacgt tcattcttc ctcttctatt ctggccacgt agccggttca       600
atgatcgcat ccttggacat gaggagaatg cagaggttga actagcgat gcttttgac        660 atcctcaaca tattacaatc gatcagactg ctcgggacga gaggacacta cacgatcgat      720
cttgcggtcg gagttggcgc tgggattctc tttgactcat tggccgggaa gtacgaagag      780
atgatgagca agagacacaa tttagccaat ggttttagtt tgatttctaa agactcgcta      840
gtcaattaa                                                              849
```

<210> SEQ ID NO 22
<211> LENGTH: 282
<212> TYPE: PRT
<213> ORGANISM: Brassica rapa

<400> SEQUENCE: 22

```
Met Ser Thr Asn Thr Val Val Pro Leu Arg Arg Ser Asn Gly Tyr
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Asn Gly Val Glu Arg
            35                  40                  45

Ser Lys Ala Ser Phe Leu Thr Trp Thr Met Arg Asp Ala Val Tyr Val
50                  55                  60

Ala Arg Tyr His Trp Ile Pro Cys Phe Phe Ala Val Gly Val Leu Phe
65                  70                  75                  80

Phe Met Gly Val Glu Tyr Thr Leu Gln Met Val Pro Ala Lys Ser Glu
                85                  90                  95

Pro Phe Asp Ile Gly Phe Val Ala Thr Arg Ser Leu Asn Arg Val Leu
            100                 105                 110

Ala Ser Ser Pro Asp Leu Asn Thr Leu Leu Ala Ala Leu Asn Thr Val
            115                 120                 125

Phe Val Ala Met Gln Thr Thr Tyr Ile Val Trp Thr Trp Leu Met Glu
130                 135                 140

Gly Arg Pro Arg Ala Thr Ile Ser Ala Cys Phe Met Phe Thr Cys Arg
145                 150                 155                 160

Gly Ile Leu Gly Tyr Ser Thr Gln Leu Pro Leu Pro Gln Asp Phe Leu
                165                 170                 175

Gly Ser Gly Val Asp Phe Pro Val Gly Asn Val Ser Phe Phe Leu Phe
            180                 185                 190

Tyr Ser Gly His Val Ala Gly Ser Met Ile Ala Ser Leu Asp Met Arg
            195                 200                 205

Arg Met Gln Arg Leu Arg Leu Ala Met Leu Phe Asp Ile Leu Asn Ile
210                 215                 220

Leu Gln Ser Ile Arg Leu Leu Gly Thr Arg Gly His Tyr Thr Ile Asp
225                 230                 235                 240

Leu Ala Val Gly Val Gly Ala Gly Ile Leu Phe Asp Ser Leu Ala Gly
                245                 250                 255
```

Lys Tyr Glu Glu Met Met Ser Lys Arg His Asn Leu Ala Asn Gly Phe
            260                 265                 270

Ser Leu Ile Ser Lys Asp Ser Leu Val Asn
        275                 280

<210> SEQ ID NO 23
<211> LENGTH: 406
<212> TYPE: DNA
<213> ORGANISM: Brassica oleracea

<400> SEQUENCE: 23
atgtcaacta ataccgtcgt ccctctccgt cgcagatcta acggatatca cactaacggc      60
gtggccttca acggaatgga gaacattgtc aagaaaaccg acgactgcta caccaatggc     120
aacggagtag agggaagag caaggcgtca tttctgacat ggaccatgcg tgacgctgtc      180
ttcgtagcga gataccattg gataccatgt ttctttgctg tcggagttct gttctttatg     240
ggggttgagt acacgctcca gatggttccg gcgaagtctg agccgttcga tattgggttt     300
gtggccacgc gctctctgaa ccgcgtcttg gcagttcac cggatcttaa caccctttta      360
gcggctctaa acacggtatt cgtagcgatg caaacgacgt atattg                    406

<210> SEQ ID NO 24
<211> LENGTH: 135
<212> TYPE: PRT
<213> ORGANISM: Brassica oleracea

<400> SEQUENCE: 24

Met Ser Thr Asn Thr Val Val Pro Leu Arg Arg Arg Ser Asn Gly Tyr
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Val Gly Gly Lys Ser Lys
        35                  40                  45

Ala Ser Phe Leu Thr Trp Thr Met Arg Asp Ala Val Phe Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Leu Asn Thr Val Phe Val
        115                 120                 125

Ala Met Gln Thr Thr Tyr Ile
    130                 135

<210> SEQ ID NO 25
<211> LENGTH: 602
<212> TYPE: DNA
<213> ORGANISM: Brassica rapa

<400> SEQUENCE: 25
atgtcaacta caacaatcgt ccctctccgt cgcacttcta actctctcaa tgaataccac      60
actaacgcag tcgcctttga cggaatcgtc gggtcagcaa gtactagcca aatggaggag     120
attgttacgc aaaccgacga ctgctacgcc aaccccaacg gagatggagg agaaagcaag     180
acgtcgttaa tgacgtggag gatgtgcaat cctgtccacg tggtgagagt ccattggata     240

-continued

```
ccgtgtttgt tgcggtagg agttctgttc ttcacgtgcg tagaggagta catgctccag    300
atgattccgg cgagttctga gccgttcgat attggttttg tggcgacggg ctctctgtat    360
cgcctcttgg cttcttcacc ggatcttaat accgttttag ctgctctcaa cacggtgttt    420
gtagggatgc aaacgacgta tatttatgg acatggttgg tggaaggacg accacgagcg    480
accatctcgg cttgcttcat gtttacttgc cgtggcattc tgggttactc tactcagctc    540
cctcttcctc aggatttct aggatcaggg gtagattttc cggtaggaaa cgtctcgttc    600
tt                                                                    602
```

<210> SEQ ID NO 26
<211> LENGTH: 200
<212> TYPE: PRT
<213> ORGANISM: Brassica rapa

<400> SEQUENCE: 26

```
Met Ser Thr Thr Thr Ile Val Pro Leu Arg Arg Thr Ser Asn Ser Leu
 1               5                  10                  15

Asn Glu Tyr His Thr Asn Ala Val Ala Phe Asp Gly Ile Val Gly Ser
            20                  25                  30

Ala Ser Thr Ser Gln Met Glu Glu Ile Val Thr Gln Thr Asp Asp Cys
        35                  40                  45

Tyr Ala Asn Pro Asn Gly Asp Gly Gly Arg Ser Lys Thr Ser Leu Met
    50                  55                  60

Thr Trp Arg Met Cys Asn Pro Val His Val Arg Val His Trp Ile
65                  70                  75                  80

Pro Cys Leu Phe Ala Val Gly Val Leu Phe Phe Thr Cys Val Glu Glu
                85                  90                  95

Tyr Met Leu Gln Met Ile Pro Ala Ser Ser Glu Pro Phe Asp Ile Gly
            100                 105                 110

Phe Val Ala Thr Gly Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Leu Trp Thr Trp Leu Val Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe
        195                 200
```

<210> SEQ ID NO 27
<211> LENGTH: 1137
<212> TYPE: DNA
<213> ORGANISM: Brassica napus

<400> SEQUENCE: 27

```
gagatgagaa aatagcaaag acttgcgtaa acgtcgctct caaacctcat ctcatactca    60
tcgttttcgt atgagttttt gtagcccaaa caatcttcct ttctacagtt tataatataa   120
gaaacaatac ttccttcgta atctccgcct cgtatctctt atataactca tctctctaaa   180
cctaaaaaat gttcctctcc gttaaatcta acggtcatgt caactaatac cgtcgtccct   240
ctccgtcgca gatctaacgg atatcacact aacggcgtgg cctttaacgg aatggataat   300
```

| | |
|---|---:|
| attgtcaaga aaaccgacga ctgctacacc aacggcaacg gcaacggagg agtagagaga | 360 |
| agcaaagcct cgtttctgac atggaccatg cgtgacgctg tctacgtagc gagataccat | 420 |
| tggataccgt gtttctttgc ggtcggagtt ctgttcttta tggggggttga gtacacgctc | 480 |
| cagatggttc cggcgaagtc tgagccgttc gatattgggt ttgtggccac gcgctctcta | 540 |
| aaccgcgtct tggcgagttc accggatctt aacacccttt tagcggctct aaacacggta | 600 |
| ttcgtagcga tgcaaacgac gtatattgta tggacatggt tgatggaagg aagaccacga | 660 |
| gccactatct cggcttgctt catgtttact tgtcgcggca ttcttggtta ctctactcag | 720 |
| ctccctctac cacaggattt tttaggatca ggagttgatt ttccggtggg aaacgtctca | 780 |
| ttcttcctct tctattctgg ccacgtagcc ggttcaatga tcgcatcctt ggacatgagg | 840 |
| agaatgcaga ggttgagact agcgatgctt tttgacatcc tcaacatatt acaatcgatc | 900 |
| agactgctcg ggacgagagg acactacacg atcgatcttg cggtcggagt tggcgctggg | 960 |
| attctctttg actcattggc cgggaagtac gaagagatga tgagcaagag acacaattta | 1020 |
| gccaatggtt ttagtttgat ttctaaagac tcgctagtca attaatcttt tgttttcatt | 1080 |
| ttaaatgatt agttgaactt gaacatattt gatttagtta aagtccaatg aattaca | 1137 |

<210> SEQ ID NO 28
<211> LENGTH: 1379
<212> TYPE: DNA
<213> ORGANISM: Brassica rapa

<400> SEQUENCE: 28

| | |
|---|---:|
| gatggtaagg aaactctcgt actcttctct atcttttgt gtgtgtttct cgtgtaaaat | 60 |
| attatacact taagacgtat aaaaagaaca acaagtaaag cccaacaaag acagatgaga | 120 |
| aaatagcaaa gacttgcgta aacgtcgctc tcaaacctca tctcatactc atcgttttcg | 180 |
| tatgagtttt tgtagcccaa acaatcttcc tttctacagt ttataatata agaaacaata | 240 |
| cttccttcgt aatctccgcc tcgtatctct tatataactc atctctctaa acctaaaaaa | 300 |
| tgttcctctc cgttaaatct aacggtcatg tcaactaata ccgtcgtccc tctccgtcgc | 360 |
| agatctaacg gatatcacac taacggcgtg gcctttaacg gaatggagaa cattgtcaag | 420 |
| aaaaccgacg actgctacac caacggcaac ggcaacggag gagtagagag aagcaaagcc | 480 |
| tcgtttctga catggaccat gcgtgacgct gtctacgtag cgagatacca ttggataccg | 540 |
| tgtttctttg cggtcggagt tctgttcttt atggggggttg agtacacgct ccagatggtt | 600 |
| ccggcgaagt ctgagccgtt cgatattggg tttgtggcca cgcgctctct gaaccgcgtc | 660 |
| ttggcgagtt caccggatct taacaccctt ttagcggctc taaacacggt attcgtagcg | 720 |
| atgcagacga cgtatattgt atggacatgg ttgatggaag gaagaccacg agccactatc | 780 |
| tcggcttgct tcatgtttac ttgtcgcggc attcttggtt actctactca gctccctcta | 840 |
| ccacaggatt ttttaggatc aggagttgat tttccggtgg gaaacgtctc attcttcctc | 900 |
| ttctattctg gccacgtagc cggttcaatg atcgcatcct tggacatgag gagaatgcag | 960 |
| aggttgagac tagcgatgct ttttgacatc ctcaacatat acaatcgat cagactgctc | 1020 |
| gggacgagag gacactacac gatcgatctt gcggtcggag ttggcgctgg gattctcttt | 1080 |
| gactcattgg ccgggaagta cgaagagatg atgagcaaga gacacaattt agccaatggt | 1140 |
| tttagtttga tttctaaaga ctcgctagtc aattaatctt ttgttttat tttaaatgat | 1200 |
| tagttgaact tgaacatatt tgatttagtt aaagtccaat gaattacatt tttttctttc | 1260 |
| aactttaatt gaatagggtt tcattagttt acttgaacct aattaaatgt gtacgttatt | 1320 |

```
gtgaaataaa gaagtttgtt gtggccttcc tacaactatt tcatcaaaaa aaaaaaaaa      1379

<210> SEQ ID NO 29
<211> LENGTH: 622
<212> TYPE: DNA
<213> ORGANISM: Brassica oleracea

<400> SEQUENCE: 29
gagatgagaa aatagcaaag acttgcgtaa acgtcgctct caaatctcat ctcatactca       60
tcgttttcgt atgagttttt gtagcccaaa caatcttcct ttctacggtt tataatataa      120
gaaacaatac ttccttcgta atctccgcct tgtatctctt atataactca tctctctaaa      180
cctaaaaaat gttcctctcc gttaaatcta acggtcatgt caactaatac cgtcgtccct      240
ctccgtcgca gatctaacgg atatcacact aacggcgtgg ccttcaacgg aatggagaac      300
attgtcaaga aaccgacga ctgctacacc aatggcaacg gagtaggagg gaagagcaag      360
gcgtcatttc tgacatggac catgcgtgac gctgtcttcg tagcgagata ccattggata      420
ccatgtttct ttgctgtcgg agttctgttc tttatggggg ttgagtacac gctccagatg      480
gttccggcga agtctgagcc gttcgatatt gggtttgtgg ccacgcgctc tctgaaccgc      540
gtcttggcga gttcaccgga tcttaacacc cttttagcgg ctctaaacac ggtattcgta      600
gcgatgcaaa cgacgtatat tg                                              622

<210> SEQ ID NO 30
<211> LENGTH: 750
<212> TYPE: DNA
<213> ORGANISM: Brassica rapa

<400> SEQUENCE: 30
gctctcaaat ctcatattca tcgttttcgt atgaactttt gtagcccaaa caaccttcct       60
ttccttccac aagtttcata taatatctct tatataaccc atctctctaa gcctctcaaa      120
acgttcttct ccgttaaatc taacggccat gtcaactaca acaatcgtcc ctctccgtcg      180
cacttctaac tctctcaatg aataccacac taacgcagtc gcctttgacg gaatcgtcgg      240
gtcagcaagt actagccaaa tggaggagat tgttacgcaa accgacgact gctacgccaa      300
ccccaacgga gatggaggga gaagcaagac gtcgttaatg acgtggagga tgtgcaatcc      360
tgtccacgtg gtgagagtcc attggatacc gtgtttgttt gcggtaggag ttctgttctt      420
cacgtgcgta gaggagtaca tgctccagat gattccggcg agttctgagc cgttcgatat      480
tggttttgtg gcgacgggct ctctgtatcg cctcttggct tcttcaccgg atcttaatac      540
cgttttagct gctctcaaca cggtgtttgt agggatgcaa acgacgtata ttttatggac      600
atggttggtg gaaggacgac cacgagcgac catctccggct tgcttcatgt ttacttgccg      660
tggcattctg ggttactcta ctcagctccc tcttcctcag gattttctag gatcagggt      720 agattttccg gtaggaaacg tctcgttctt                                      750
```

COMPOSITIONS AND METHODS FOR DIFFERENTIAL REGULATION OF FATTY ACID UNSATURATION IN MEMBRANE LIPIDS AND SEED OIL

CROSS REFERENCE TO RELATED APPLICATIONS

This application is a continuation of U.S. patent application Ser. No. 12/921,119, filed Feb. 1, 2011, which is the United States national stage, pursuant to 35 U.S.C. § 371, of International Patent Application No. PCT/US2009/036066, filed Mar. 4, 2009, which claims the benefit of priority to U.S. Provisional Patent Application No. 61/149,288, filed Feb. 2, 2009, and U.S. Provisional Patent Application No. 61/033,742, filed Mar. 4, 2008, all of which are incorporated herein by reference in their entirety.

STATEMENT REGARDING FEDERALLY FUNDED RESEARCH

This invention was made, at least in part, with Government support under grants 2006-35318-17797 and 97-35301-4426 awarded by the United States Department of Agriculture (USDA), and the United States Government, therefore, has certain rights in the invention.

SEQUENCE LISTING

A Sequence Listing comprising SEQ ID NOS:1-30, has been provided in computer readable form (.txt) as part of this application, and is incorporated by reference herein in its entirety as part of this application.

FIELD OF THE INVENTION

Aspects of the invention relate generally to fatty acid biosynthesis, membrane lipids and plant seed oils, and more particularly to biosynthesis of unsaturated fatty acids and related acylglycerols and to compositions and methods for differential regulation of fatty acid unsaturation in seed oil and membrane lipids of plants based on modulation of a previously unknown biosynthetic pathway involving a novel phosphatidylcholine:diacylglycerol cholinephosphotransferase (PDCT) that regulates phosphatidylcholine biosynthesis in developing oilseed plants (e.g., of *Arabidopsis*, soybean (*Glycine max*), canola (*Brassica napus* or *B. rapa*), sunflower (*Helianthus annuus*), etc.). Specific aspects relate to inventive PDCT polypeptides including, for example, variants, deletions, muteins, fusion proteins, and orthologs thereof (collectively PDCT proteins), to isolated nucleic acids encoding same, to plants comprising such PDCT proteins or devoid of such PDCT proteins, and to methods for generating plants having altered or no PDCT expression and/or activity, including but not limited to methods comprising mutagenesis, gene-silencing, antisense, siRNA, recombinant DNA, transgenics, etc.).

BACKGROUND

Many plant species including, for example, *Arabidopsis thaliana* store triacylglycerols (TAGs) in their seeds as a carbon reserve. These TAGs are the major source of energy and carbon material that supports seedling development during the early stages of plant life. Vegetable oils from soybean (*Glycine max*), canola (*Brassica napus* or *B. rapa*), sunflower (*Helianthus annuus*) and many other oilseed crops are also an important source of oil for the human diet or industrial applications including, but not limited to biofuels, biolubricants, nylon precursors, and detergent feedstocks. The degree and/or amount of polyunsaturated fatty acids of vegetable oils are characteristic and determinative properties with respect to oil uses in food or non-food industries. More specifically, the characteristic properties and utilities of vegetable oils are largely determined by their fatty acyl compositions in TAG.

Major vegetable oils are comprised primarily of palmitic (16:0), stearic (18:0), oleic (18:1cis $\Delta^9$), linoleic (18:2cis $\Delta^{9, 12}$), and α-linolenic (18:3cis $\Delta$9, 12, 15) acids. Modifications of the fatty acid compositions have been sought after for at least a century in order to provide optimal oil products for human nutrition and chemical (e.g., oleochemical) uses (1-3). In particular, the polyunsaturated fatty acids (18:2 and 18:3) have received considerable attention because they are major factors that affect nutritional value and oil stability. However, while these two fatty acids provide essential nutrients for humans and animals, they increase oil instability because they comprise multiple double bonds that may be easily oxidized during processing and storage.

Limitations of the Art.

The desaturation of 18:1 into 18:2 is a critical step for synthesizing polyunsaturated fatty acids. During storage lipid biosynthesis, this reaction is known to be catalyzed by the fatty acid desaturase, FAD2, a membrane-bound enzyme located on the endoplasmic reticulum (ER) (4). The FAD2 substrate 18:1 must be esterified on the sn-2 position of phosphatidylcholine (PC) (5, 6), which is the major membrane phospholipid of plant cells. Not surprisingly, therefore, down-regulation of FAD2 (and FAD3) genes has become a preferred strategy for avoiding the need to hydrogenate vegetable oils and the concomitant production of undesirable trans fatty acids. For example, soybean has both seed-specific and constitutive FAD2 desaturases, so that gene silencing of the seed-specific isoform has allowed the production of high-oleate cultivars (>88% 18:1 in the oil) in which membrane unsaturation and plant performance are largely unaffected. Significantly, however, such FAD2 gene-silencing strategies are substantially limited because, for example, canola and other oilseed plants have only constitutive FAD2 enzymes. Therefore, in canola and other such constitutive FAD2 crops, silencing or down-regulation of FAD2 not only alters the fatty acid composition of the storage triacylglycerol (TAG) in seeds, but also of the cellular membranes, which severely compromises growth and yield of the plant. For example, the defective FAD2 in the *Arabidopsis* mutant fad2 alters fatty acid compositions of seeds as well as vegetable tissues, and severely compromises plant growth (4). FAD2 mutations and silencing that produce the highest 18:1 levels in the oil also reduce membrane unsaturation in vegetative and seed tissues, resulting in plants that germinate and grow poorly. As a result, only partial downregulation of FAD2 expression is possible, producing approximately 70-75% 18:1 in the oil of commercial cultivars such as Nexera/Natreon (Dow Agro-Sciences) and Clear Valley 75 (Cargill).

There is, therefore, a pronounced need in the art for novel compositions and methods for differential regulation of fatty acid unsaturation in seed oil and membrane lipids of plants, and for viable plants (e.g., canola, etc.) having reduced fatty acid unsaturation in seed oils, without deleterious alterations in the unsaturation of membrane lipid components.

SUMMARY OF EXEMPLARY EMBODIMENTS

Particular aspects provide novel compositions and methods for differential regulation of fatty acid unsaturation in seed oil and membrane lipids, without deleterious alterations in the unsaturation of membrane lipid components.

Additional aspects provide compositions and methods for differential regulation of fatty acid unsaturation in seed oil and membrane lipids of plants, based on modulation of a previously unknown biosynthetic pathway involving a novel phosphatidylcholine:diacylglycerol cholinephosphotransferase (PDCT) that regulates phosphatidylcholine biosynthesis in developing oilseed plants (e.g., of *Arabidopsis*, soybean (*Glycine max*), canola (*Brassica napus* or *B. rapa*), sunflower (*Helianthus annuus*), etc.).

Further aspects provide inventive PDCT polypeptides including, for example, variants, deletions, muteins, fusion proteins, and orthologs thereof (collectively PDCT proteins).

Yet additional aspects provide plants comprising such PDCT sequences or proteins or devoid or depleted of such PDCT proteins or sequences, and methods for generating plants having altered or no PDCT expression and/or activity, including but not limited to methods comprising mutagenesis, gene-silencing, antisense, siRNA, recombinant DNA, transgenics, etc.).

Specific aspects provide a method for regulation of fatty acid unsaturation in seed oil, comprising: obtaining an oilseed-bearing plant; and modulating the expression or activity of at least one phosphatidylcholine:diacylglycerol cholinephosphotransferase (PDCT) in one or more seeds or developing seeds of the plant, wherein the level, amount, or distribution of fatty acid unsaturation in the seed oil is modified relative to the seed oil of plants with normal seed expression of the PDCT. In certain embodiments, modulating the expression or activity of the at least one PDCT comprises down-regulating the expression or activity, wherein the level, amount, or distribution of fatty acid unsaturation in the seed oil is modified is reduced. Preferably, the method comprises differential regulation of fatty acid unsaturation in seed oil relative to fatty acid unsaturation in one or more membrane lipids. Preferably, the fatty acid unsaturation in seed oil relative to fatty acid unsaturation in one or more membrane lipids is differentially reduced in seed oil.

Additional aspects provide a method of producing an oil seed-bearing plant or a part thereof, comprising imparting into the germplasm of an oil seed-bearing plant variety a mutation or genetic alteration that modifies the expression or activity of at least one PDCT in one or more seeds or developing seeds of the plant, wherein the level, amount, or distribution of fatty acid unsaturation in the seed oil is modified relative to the seed oil of plants with normal seed expression of the PDCT.

Further embodiments comprise an oil seed-bearing plant or a part thereof, comprising a mutation or genetic alteration that modifies the expression or activity of at least one phosphatidylcholine:diacylglycerol cholinephosphotransferase (PDCT) in one or more seeds or developing seeds of the plant, wherein the level, amount, or distribution of fatty acid unsaturation in the seed oil is modified relative to the seed oil of plants with normal seed expression of the PDCT. While the mutation or genetic alteration may be one that modulates PDCT expression and/or activity directly or indirectly, in particular aspects the mutation comprises a mutation of at least one PDCT sequence that modifies the expression or activity thereof in one or more seeds or developing seeds of the plant, wherein the level, amount, or distribution of fatty acid unsaturation in the seed oil is modified relative to the seed oil of plants with normal seed expression of the PDCT.

Additional aspects provide a seed or true-breeding seed derived from the oil seed-bearing plants or parts thereof as provided for herein.

Further aspects provide an oil derived from the oil seed-bearing plants or parts thereof as provided for herein.

Yet additional embodiments provide a fuel (e.g., bio-fuel), based at least in part on at least one oil derived from the oil seed-bearing plants or parts thereof as provided for herein.

BRIEF SUMMARY OF THE DRAWINGS

FIG. 4 shows the ROD1 mutant truncated amino acid sequence (SEQ ID NO:5) in DH4. According to particular aspects, a phosphatidylcholine:diacylglycerol cholinephosphotransferase (PDCT) mutant (rod1) coding sequence (SEQ ID NO:4) comprises a G>A change at nucleotide position 228, resulting in premature termination of the PDCT protein to provide a 75 amino acid truncated ROD1 mutant sequence (SEQ ID NO:5);

DETAILED DESCRIPTION OF EXEMPLARY EMBODIMENTS

Figures 1A, 1B, 1C, 1D:
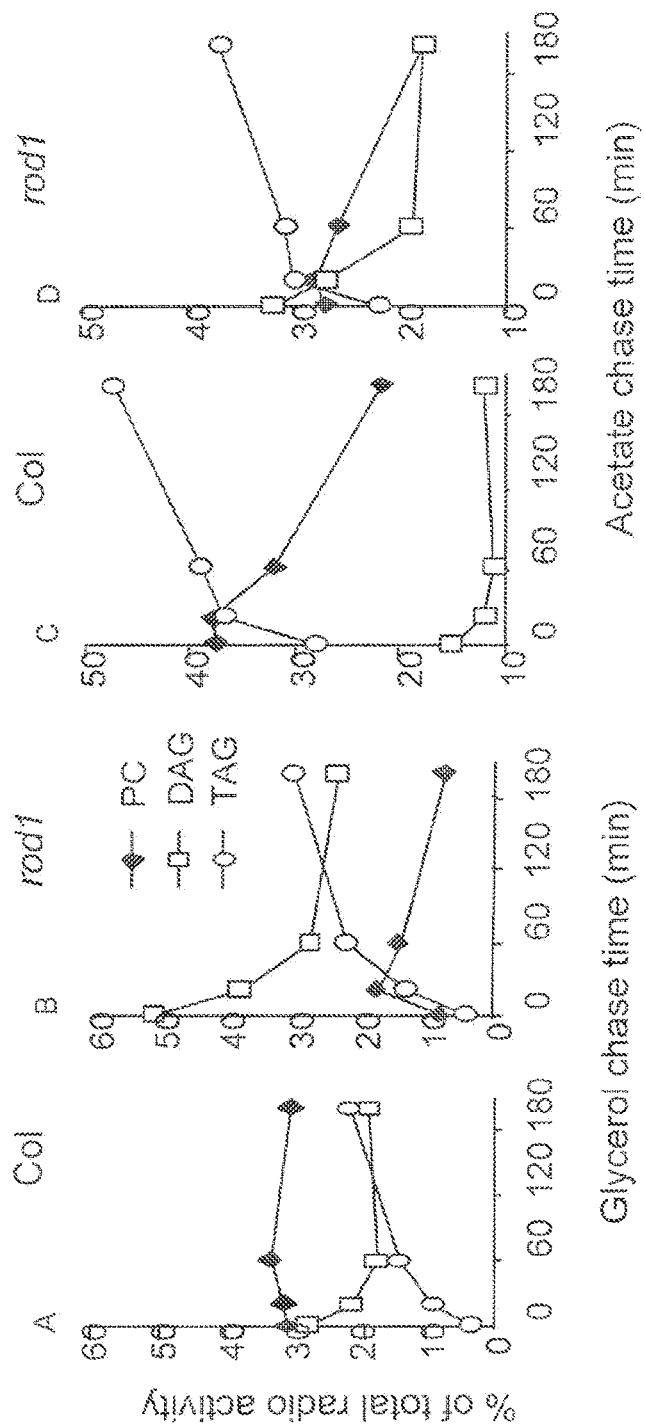
FIGS. 1A-1D show lipid synthesis in developing seeds of *Arabidopsis*. Developing seeds were labeled with radioactive acetate (to label fatty acids) (FIGS. 1C and 1D) and radioactive glycerol (to label the lipid backbone) (FIGS. 1A and 1B). After 15 min of pulse with [14-C] labeled glycerol (C) or acetate (D), the chase was carried out for 180 min. Radio activity in PC, DG and TG were determined at 0, 30, 60 and 180 min time points.
Figures 1E, 1F, 1G, 1H:
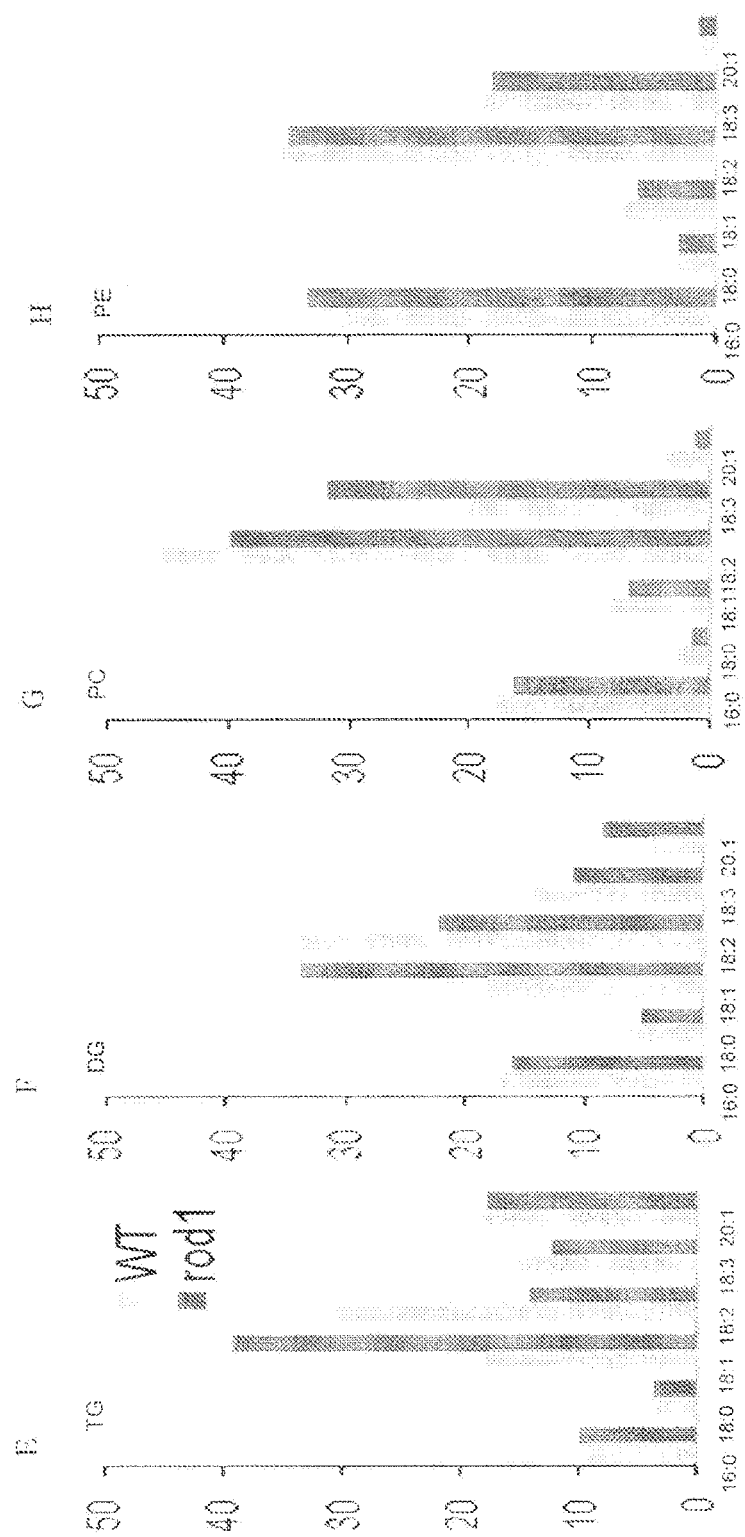
FIGS. 1E-1H show a comparison of fatty acid composition between rod1 and WT in TG, DG, PC and PE from developing seeds at 9 days after flowering.

Particular aspects provide novel compositions and methods for differential regulation of fatty acid unsaturation in seed oil and membrane lipids, without deleterious alterations in the unsaturation of membrane lipid components.

Additional aspects provide compositions and methods for differential regulation of fatty acid unsaturation in seed oil and membrane lipids of plants, based on modulation of a previously unknown biosynthetic pathway involving a novel phosphatidylcholine:diacylglycerol cholinephosphotransferase (PDCT) that regulates phosphatidylcholine biosynthesis in developing oilseed plants (e.g., of *Arabidopsis*, soybean (*Glycine max*), canola (*Brassica napus* or *B. rapa*), sunflower (*Helianthus annuus*), etc.).

Further aspects provide inventive PDCT sequences and polypeptides including, for example, mutants (e.g., SEQ ID NOS:4 and 5), variants, deletions, muteins, fusion proteins, and orthologs thereof (collectively PDCT proteins).

Yet additional aspects provide plants comprising such PDCT proteins or devoid or depleted of such PDCT sequences or proteins and/or activities, and methods for generating plants having altered or no PDCT expression and/or activity, including but not limited to art-recognized methods comprising mutagenesis, gene-silencing, antisense, siRNA, recombinant DNA, transgenics, etc.). Information about mutagens and mutagenizing seeds or pollen, for example, are presented in the IAEA's Manual on Mutation Breeding (IAEA, 1977). In certain embodiments, mutagenesis comprises chemical mutagenesis (e.g., comprising treatment of seeds with ethyl methane sulfonate (EMS). Various plant breeding methods are also useful in providing inventive plants are discussed in detail herein below.

As described herein below, specific exemplary aspects of the present invention provide a genetic and biochemical characterization of an *Arabidopsis* mutant plant with reduced desaturation in seed fatty acids (see Table 1 of EXAMPLE 2 below). The mutant plant, originally identified and named as DH4 (7), was indistinguishable from its parental wild type Col-0 plants grown under standard conditions. Applicants herein disclose a gene ROD1 (Reduced Oleate Desaturation 1) encoding the PDCT, which mutation in the DH4 *Arabidopsis* mutant causes reduced oleate desaturation levels in seed oils. The rod1 allele in DH4 is a single recessive Mendelian mutation as determined by genetic analysis. As shown herein (working EXAMPLE 2), the defective PDCT activity in the rod1 mutant resulted in impaired transfer of 18:1 fatty acid into phosphatidylcholine (PC) during triacylglycerol synthesis in developing seeds. The results indicate that PDCT is a major factor that regulates lipid flux into phosphatidylcholine, where most fatty acid modifications take place in oilseeds.

Significantly, compared to the fad2 mutant (5, 7), the fatty acid composition change in DH4 is restricted to seed oil.

As described under working EXAMPLE 3 herein below, specific exemplary aspects of the present invention show that the *Arabidopsis* mutant rod1 locus of DH4 was shown to mediate reduced oleate desaturation in seed oil due to a reduced transfer of 18:1 into PC via de novo synthesis from diacylglycerol (DAG).

According to additional aspects, as described in EXAMPLE 4 herein below, fine mapping of the *Arabidopsis* mutant rod1 of DH4 was performed and At3g15820 (SEQ ID NO:2) was herein identified as the locus of the rod1 mutant (SEQ ID NO:4), and for the first time was shown not only to be a phosphatidylcholine:diacylglycerol cholinephosphotransferase (PDCT), but also a PDCT that is highly expressed in developing seeds with the highest level at stage 6 of seed development, which coincides the peak stage of storage deposition.

Significantly, At3g15820 (SEQ ID NO:2) has previously been annotated as a putative type 2 phosphatidic acid phosphatase (PAP2)-like protein. Surprisingly however, upon analysis by Applicants, it did not show strong homology to known characterized PAP genes in *Arabidopsis* (AtLPP1, AtLPP2 and AtLPP3) (13, 14), and Applicants have determined herein that ROD1 contains essentially no sequence homology to these true PAP2 orthologues, and concluded that ROD1 encodes a different function.

Applicants tested ROD1 for PDCT activity, by expressing the cDNA of At3g15820 under control of the inducible GAL1 promoter in a double-mutant yeast strain HJ091 (17) lacking all CDP-choline:diacylglycerol cholinephosphotransferase activities. As detailed herein (EXAMPLE 4), these results indicate that ROD1 does not possess PA phosphatase activity, and substantially confirms that ROD1 rather confers a PDCT activity, which is consistent with the fact that the rod1 mutant is defective in PC synthesis in developing seeds.

According to additional aspects, as described in EXAMPLE 5 herein below, ROD1 (At3g15820) orthologs were identified that have significant sequence homology/identity. Tables 2 and 3 of EXAMPLE 5 show nucleotide similarity (% identity) and protein sequence similarity (% identity), respectively, for exemplary ROD1 orthologs from *Brassica* (SEQ ID NO:6; SEQ ID NO:7), Moss (SEQ ID NO:16; SEQ ID NO:17), Spruce (SEQ ID NO:14; SEQ ID NO:15), Grape (SEQ ID NO:12; SEQ ID NO:13), Rice (SEQ ID NO:10; SEQ ID NO:11) and Castor (SEQ ID NO:8; SEQ ID NO:9), showing a range of nucleic acid identity from about 46 to 80%, and range of protein sequence identity from about 42 to 85%.

According to further aspects, as described in EXAMPLE 6 herein below, the *Brassica napus* unigene Bna.6194 is identified as the true *Arabidopsis* ROD1 (At3g15820) homologue. Applicants named Bna.6194 as BnROD1. Quantitative RT-PCR showed that BnROD1 is highly expressed in canola developing seeds. *Brassica napus* is an amphidipoid including *Brassica rapa* and *Brassica oleracea* two subgenomes. The sequence alignment also suggested that BnROD1 might be the true homologue of *Brassica rapa* unigene Bra. 2038 and *Brassica oleracea* ES948687.

According to further aspects, as described in EXAMPLE 7 herein below, biological materials (e.g., plant seed oils), as provided for herein, that contain relatively high concentrations of long chain fats with modest unsaturation provide improved feedstocks for the production of biodiesel and related products, as well as food oils.

Specific Preferred Exemplary Embodiments

Particular aspects provide a method for regulation of fatty acid unsaturation in seed oil, comprising: obtaining an oilseed-bearing plant; and modulating the expression or activity of at least one phosphatidylcholine:diacylglycerol cholinephosphotransferase (PDCT) in one or more seeds or developing seeds of the plant, wherein the level, amount, or distribution of fatty acid unsaturation in the seed oil is modified relative to the seed oil of plants with normal seed expression of the PDCT. In certain embodiments, modulating the expression or activity of the at least one PDCT comprises down-regulating the expression or activity, wherein the level, amount, or distribution of fatty acid unsaturation in the seed oil is modified or reduced. Preferably, the method comprises differential regulation of fatty acid unsaturation in seed oil relative to fatty acid unsaturation in one or more membrane lipids. Preferably, the fatty acid unsaturation in seed oil relative to fatty acid unsaturation in one or more membrane lipids is differentially reduced in seed oil. In particular embodiments, the at least one PDCT comprises at least one sequence selected from the group consisting of SEQ ID NO:3, a sequence having at least 46, at least 48%, at least 58%, at least 64%, at least 71% or at least 85% amino acid sequence identity therewith, and PDCT-active portions thereof. In certain embodiments, the at least one PDCT comprises at least one sequence selected from the group consisting of SEQ ID NOS:7, 9, 11, 13, 15, 17, and PDCT-active portions thereof. In certain implementation, modulating the expression or activity of the at least one PDCT comprises the use of at least one of mutagenesis and recombinant DNA methods, including, but not limited to the use of at least one of gene-silencing, anti-sense methods, siRNA methods, transgenic methods.

Additional aspects provide a method of producing an oil seed-bearing plant or a part thereof, comprising imparting into the germplasm of an oil seed-bearing plant variety a mutation or genetic alteration that modifies the expression or activity of at least one PDCT in one or more seeds or developing seeds of the plant, wherein the level, amount, or distribution of fatty acid unsaturation in the seed oil is modified relative to the seed oil of plants with normal seed expression of the PDCT. Particular embodiments of the method comprise: providing germplasm of an oil seed-bearing plant variety; treating the germplasm with a mutagen to produce a mutagenized germplasm; selecting from the mutagenized germplasm an oil seed-bearing plant seed comprising a genotype, caused by the mutagen, that modifies the expression or activity of at least one phosphatidylcholine:diacylglycerol cholinephosphotransferase (PDCT) in one or more seeds or developing seeds of the plant, wherein the level, amount, or distribution of fatty acid unsaturation in the seed oil is modified relative to the seed oil of plants with normal seed expression of the PDCT; and growing an oil seed-bearing plant from the seed. In particular implementation of the method, producing a matagenized germplasm comprises producing a mutation of at least one phosphatidylcholine:diacylglycerol cholinephosphotransferase (PDCT) sequence that modifies the expression or activity thereof in one or more seeds or developing seeds of the plant, wherein the level, amount, or distribution of fatty acid unsaturation in the seed oil is modified relative to the seed oil of plants with normal seed expression of the PDCT. Further embodiments comprise an oil seed-bearing plant or a part thereof, comprising a mutation or genetic alteration that modifies the expression or activity of at least one phosphatidylcholine:diacylglycerol cholinephosphotransferase (PDCT) in one or more seeds or developing seeds of the plant, wherein the level, amount, or distribution of fatty acid unsaturation in the seed oil is modified relative to the seed oil of plants with normal seed expression of the PDCT. While the mutation or genetic alteration may be one that modulates PDCT expression and/or activity directly or indirectly, in particular aspects the mutation comprises a mutation of at least one PDCT sequence that modifies the expression or activity thereof in one or more seeds or developing seeds of the plant, wherein the level, amount, or distribution of fatty acid unsaturation in the seed oil is modified relative to the seed oil of plants with normal seed expression of the PDCT. In certain aspects, the oil seed-bearing plant or a part thereof is other than *Arabidopsis*. Preferably in such plants, modulating the expression or activity of the at least one PDCT comprises down-regulating the expression or activity, wherein the level, amount, or distribution of fatty acid unsaturation in the seed oil is modified is reduced. Preferably, modulating the expression or activity comprises differential regulation of fatty acid unsaturation in seed oil relative to fatty acid unsaturation in one or more membrane lipids. Particular plant embodiments comprise two or more different mutations or genetic alterations that modify the level, amount, or distribution of fatty acid unsaturation in the seed oil, wherein at least one of the two or more different mutations or genetic alterations is a mutation or genetic alteration that modifies the expression or activity of at least one phosphatidylcholine:diacylglycerol cholinephosphotransferase (PDCT) in one or more seeds or developing seeds of the plant. In particular embodiments of such plants, at least one of the two or more different mutations is a FAD2 desaturase mutation that reduces or eliminates FAD2 activity or amount in the seed or developing seed. In certain aspects, the at least one PDCT comprises at least one sequence selected from the group consisting of SEQ ID NO:3, a sequence having at least 46, at least 48%, at least 58%, at least 64%, at least 71% or at least 85% amino acid sequence identity therewith, and PDCT-active portions thereof. In particular embodiments, the at least one PDCT comprises at least one sequence selected from the group consisting of SEQ ID NOS:7, 9, 11, 13, 15, 17, and PDCT-active portions thereof.

Additional aspects provide a seed or true-breeding seed derived from the oil seed-bearing plants or parts thereof as provided for herein.

Further aspects, provide an oil derived from the oil seed-bearing plants or parts thereof as provided for herein.

Yet additional embodiments provide a fuel, based at least in part on an oil derived from the oil seed-bearing plants or parts thereof as provided for herein.

Plants and Plant Breeding

Particular aspects provide an oil seed-bearing plant or a part thereof, comprising a mutation or genetic modification that modifies the expression or activity of at least one phosphatidylcholine:diacylglycerol cholinephosphotransferase (PDCT) in one or more seeds or developing seeds of the plant, wherein the level, amount, or distribution of fatty acid unsaturation in the seed oil is modified relative to the seed oil of plants with normal seed expression of the PDCT. While the mutation or genetic modification may be any that modifies the PDCT expression and/or activity, in preferred aspect, the mutation comprises a mutation of at least one phosphatidylcholine:diacylglycerol cholinephosphotransferase (PDCT) sequence that modifies the expression or activity thereof in one or more seeds or developing seeds of the plant, wherein the level, amount, or distribution of fatty acid unsaturation in the seed oil is modified relative to the seed oil of plants with normal seed expression of the PDCT.

Various plant breeding methods are also useful in establishing useful plant varieties based on such mutations or genetic modifications.

Plant Breeding

Additional aspects comprise methods for using, in plant breeding, an oil seed-bearing plant, comprising a mutation that modifies the expression or activity of at least one phosphatidylcholine:diacylglycerol cholinephosphotransferase (PDCT) (as provided for herein) in one or more seeds or developing seeds of the plant, wherein the level, amount, or distribution of fatty acid unsaturation in the seed oil is modified relative to the seed oil of plants with normal seed expression of the PDCT. One such embodiment is the method of crossing a particular PDCT mutant variety with another variety of the plant to form a first generation population of F1 plants. The population of first generation F1 plants produced by this method is also an embodiment of the invention. This first generation population of F1 plants will comprise an essentially complete set of the alleles of the particular PDCT mutant variety. One of ordinary skill in the art can utilize either breeder books or molecular methods to identify a particular F1 plant produced using the particular PDCT mutant variety, and any such individual plant is also encompassed by this invention. These embodiments also cover use of transgenic or backcross conversions of particular PDCT mutant varieties to produce first generation F1 plants.

Yet additional aspects comprise a method of developing a particular PDCT mutant-progeny plant comprising crossing a particular PDCT mutant variety with a second plant and performing a breeding method is also an embodiment of the invention.

General Breeding and Selection Methods

Overview.

Plant breeding is the genetic manipulation of plants. The goal of plant breeding is to develop new, unique and superior plant varieties. In practical application of a plant breeding program, and as discussed in more detail herein below, the breeder initially selects and crosses two or more parental lines, followed by repeated 'selfing' and selection, producing many new genetic combinations. The breeder can theoretically generate billions of different genetic combinations via crossing, 'selfing' and naturally induced mutations. The breeder has no direct control at the cellular level, and two breeders will never, therefore, develop exactly the same line. Each year, the plant breeder selects the germplasm to advance to the next generation. This germplasm may be grown under unique and different geographical, climatic and soil conditions, and further selections may be made during and at the end of the growing season.

Proper testing can detect major faults and establish the level of superiority or improvement over current varieties. In addition to showing superior performance, it is desirable that this a demand for a new variety. The new variety should optimally be compatible with industry standards, or create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. Ideally, it should also be feasible to produce seed easily and economically.

The term 'homozygous plant' is hereby defined as a plant with homozygous genes at 95% or more of its loci.

The term "inbred" as used herein refers to a homozygous plant or a collection of homozygous plants.

Choice of Breeding or Selection Methods.

Choice of breeding or selection methods depends on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection should be based on mean values obtained from replicated evaluations of families of related plants. The complexity of inheritance also influences choice of the breeding method. Breeding generally starts with cross-hybridizing two genotypes (a "breeding cross"), each of which may have one or more desirable characteristics that is lacking in the other or which complements the other. If the two original parents do not provide all the desired characteristics, other sources can be included by making more crosses. In each successive filial generation (e.g., F1→F2; F2→F3; F3→F4; F4→F5, etc.), plants are 'selfed' to increase the homozygosity of the line. Typically in a breeding program five or more generations of selection and 'selfing' are practiced to obtain a homozygous plant. Each plant breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful varieties produced per unit of input (e.g., per year, per dollar expended, etc.).

Backcross Conversion

An additional embodiment comprises or is a backcross conversion of an oil seed-bearing plant, comprising a mutation that modifies the expression or activity of at least one phosphatidylcholine:diacylglycerol cholinephosphotransferase (PDCT) (as provided for herein) in one or more seeds or developing seeds of the plant, wherein the level, amount, or distribution of fatty acid unsaturation in the seed oil is modified relative to the seed oil of plants with normal seed expression of the PDCT. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to nutritional enhancements, industrial enhancements, disease resistance, insect resistance, herbicide resistance, agronomic enhancements, grain quality enhancement, waxy starch, breeding enhancements, seed production enhancements, and male steriltiy. A further embodiment comprises or is a method of developing a backcross conversion plant that involves the repeated backcrossing to such PDCT mutations. The number of backcrosses made may be 2, 3, 4, 5, 6 or greater, and the specific number of backcrosses used will depend upon the genetics of the donor parent and whether molecular markers are utilized in the backcrossing program.

Essentially Derived Varieties

Another embodiment of the invention is an essentially derived variety of an oil seed-bearing plant, comprising a mutation that modifies the expression or activity of at least one phosphatidylcholine:diacylglycerol cholinephosphotransferase (PDCT) (as provided for herein) in one or more seeds or developing seeds of the plant, wherein the level, amount, or distribution of fatty acid unsaturation in the seed oil is modified relative to the seed oil of plants with normal seed expression of the PDCT. As determined by the UPOV Convention, essentially derived varieties may be obtained for example by the selection of a natural or induced mutant, or of a somaclonal variant, the selection of a variant individual from plants of the initial variety, backcrossing, or transformation by genetic engineering. An essentially derived variety of such PDCT mutants is further defined as one whose production requires the repeated use thereof, or is predominately derived from genotype of a particular PDCT mutant. International Convention for the Protection of New Varieties of Plants, as amended on Mar. 19, 1991, Chapter V, Article 14, Section 5(c).

DNA Constructs

The present invention also contemplates the fabrication of DNA constructs (e.g., expression vectors, recombination vectors, anti-sense constructs, siRNA constructs, etc.) comprising the isolated nucleic acid sequence containing the genetic element and/or coding sequence from the disclosed PDCT mutant varieties operatively linked to plant gene expression control sequences. "DNA constructs" are defined herein to be constructed (not naturally-occurring) DNA molecules useful for introducing DNA into host cells, and the term includes chimeric genes, expression cassettes, and vectors.

As used herein "operatively linked" refers to the linking of DNA sequences (including the order of the sequences, the orientation of the sequences, and the relative spacing of the various sequences) in such a manner that the encoded protein is expressed. Methods of operatively linking expression control sequences to coding sequences are well known in the art. See, e.g., Maniatis, et al., Molecular Cloning: A Laboratory Manual, Cold Spring Harbor, N.Y., 1982; and Sambrook, et al., Molecular Cloning: A Laboratory Manual, Cold Spring Harbor, N.Y., 1989.

"Expression control sequences" are DNA sequences involved in any way in the control of transcription or translation. Suitable expression control sequences and methods of making and using them are well known in the art.

The expression control sequences preferably include a promoter. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley and Reynolds, Nucleic Acids Res., 15, 2343-2361, 1987. Also, the location of the promoter relative to the transcription start may be optimized. See, e.g., Roberts, et al., Proc. Natl. Acad. Sci. USA, 76:760-764, 1979.

Many suitable promoters for use in plants are well known in the art. For instance, suitable constitutive promoters for use in plants include the promoters of plant viruses, such as the peanut chlorotic streak caulimovirus (PC1SV) promoter (U.S. Pat. No. 5,850,019); the 35S and 19S promoter from cauliflower mosaic virus (CaMV) (Odell, et al., I 313:3810-812, 1985); promoters of the *Chlorella* virus methyltransferase genes (U.S. Pat. No. 5,563,328); the full-length transcript promoter from figwort mosaic virus (FMV) (U.S. Pat. No. 5,378,619); the promoters from such genes as rice actin (McElroy, et al., Plant Cell 2:163-171 (1990)), ubiquitin (Christiansen, et al., Plant Mol. Biol. 12:619-632, 1989), and (Christiansen, et al., Plant Mol. Biol. 18: 675-689, 1992), pEMU (Last, et al., Theor. Appl. Genet. 81:581-588, 1991), MAS (Velten, et al., Embo J. 3:2723-2730, 1984), wheat histone (Lepetit, et al., Mol. Gen. Genet. 231:276-285, 1992), and Atanassova, et al., Plant Journal 2:291-300, 1992), *Brassica napus* ALS3 (International Publication No. WO 1997/41228); and promoters of various *Agrobacterium* genes (see U.S. Pat. Nos. 4,771,002; 5,102, 796; 5,182,200; and 5,428,147).

Suitable inducible promoters for use in plants include: the promoter from the ACE1 system which responds to copper (Mett, et al., Proc. Natl. Acad. Sci. 90:4567-4571, 1993): the promoter of the wheat In 2 gene which responds to benzenesulfonomide herbicide safeners (U.S. Pat. No. 5,364,780 and Gatz, et al., Mol. Gen. Genet. 243:32-38, 1994), and the promoter of the Tet repressor from Tn10 (Gatz, et al., Mol. Gen. Genet. 227:229-237, 1991). According to one embodiment, the promoter for use in plants is one that responds to an inducing agent to which plants normally do not respond. An exemplary inducible promoter of this type is the inducible promoter from a steroid hormone gene, the transcriptional activity of which is induced by a glucosteroid hormone (Schena, et al., Proc. Natl. Acad. Sci. 88:10421, 1991) or the application of a chimeric transcription activator, XVE, for use in an estrogen receptor-based inducible plant expression system activated by estradiol (Zou, et al., Plant J. 24 265-273, 2000). Other inducible promoters for use in plants are described in European Patent No. 332104, International Publication No. WO 1993/21334 and International Publication No. WO 1997/06269, and discussed in Gatz and Lenk Trends Plant Sci., 3:352-358, 1998, and Zou and Chua, Curr. Opin. Biotechnol., 11:146-151, 2000. Finally, promoters composed of portions of other promoters and partially or totally synthetic promoters can be used. See, e.g., Ni, et al., Plant J. 7:661-676, 1995, and International Publication No. WO 1995/14098, which describes such promoters for use in plants.

The promoter may include, or be modified to include, one or more enhancer elements. Preferably, the promoter will include a plurality of enhancer elements. Promoters containing enhancer elements provide for higher levels of transcription as compared to promoters that do not include them. Suitable enhancer elements for use in plants include the PC1SV enhancer element (U.S. Pat. No. 5,850,019), the CaMV 35S enhancer element (U.S. Pat. Nos. 5,106,739 and 5,164,316), and the FMV enhancer element (Maiti, et al., Transgenic Res., 6:143-156, 1997). See also, International Publication No. WO 1996/23898 and Enhancers and Eukaryotic Expression (Cold Spring Harbor Press, Cold Spring Harbor, N.Y., 1983).

For efficient expression, the coding sequences are preferably also operatively linked to a 3' untranslated sequence. The 3' untranslated sequence will preferably include a transcription termination sequence and a polyadenylation sequence. The 3' untranslated region can be obtained from the flanking regions of genes from *Agrobacterium*, plant viruses, plants and other eukaryotes. Suitable 3' untranslated sequences for use in plants include those of the cauliflower mosaic virus 35S gene, the phaseolin seed storage protein gene, the pea ribulose-1,5-bisphosphate carboxylase small subunit E9 gene, the wheat 7S storage protein gene, the octopine synthase gene, and the nopaline synthase gene.

A 5' untranslated leader sequence can also be optionally employed. The 5' untranslated leader sequence is the portion of an mRNA that extends from the 5' CAP site to the translation initiation codon. This region of the mRNA is necessary for translation initiation in plants and plays a role in the regulation of gene expression. Suitable 5' untranslated leader sequence for use in plants includes those of alfalfa mosaic virus, cucumber mosaic virus coat protein gene, and tobacco mosaic virus.

The DNA construct may be a 'vector.' The vector may contain one or more replication systems which allow it to replicate in host cells. Self-replicating vectors include plasmids, cosmids and virus vectors. Alternatively, the vector may be an integrating vector which allows the integration into the host cell's chromosome of the DNA sequence encoding the root-rot resistance gene product. The vector desirably also has unique restriction sites for the insertion of DNA sequences. If a vector does not have unique restriction sites it may be modified to introduce or eliminate restriction sites to make it more suitable for further manipulation.

Vectors suitable for use in expressing the nucleic acids, which when expressed in a plant modulate the expression or activity of at least one phosphatidylcholine:diacylglycerol cholinephosphotransferase (PDCT) (as provided for herein) in one or more seeds or developing seeds of the plant, wherein the level, amount, or distribution of fatty acid unsaturation in the seed oil is modified relative to the seed oil of plants with normal seed expression of the PDCT, include but are not limited to pMON979, pMON977, pMON886, pCaMVCN, and vectors derived from the tumor inducing (Ti) plasmid of *Agrobacterium tumefaciens* described by Rogers, et al., Meth. Enzymol., 153:253-277, 1987. The nucleic acid is inserted into the vector such that it is operably linked to a suitable plant active promoter. Suitable plant active promoters for use with the nucleic acids include, but are not limited to CaMV35S, ACTIN, FMV35S, NOS and PCSLV promoters. The vectors comprising the nucleic acid can be inserted into a plant cell using a variety of known methods. For example, DNA transformation of plant cells include but are not limited to *Agrobacterium*-mediated plant transformation, protoplast transformation, electroporation, gene transfer into pollen, injection into reproductive organs, injection into immature embryos and particle bombardment. These methods are described more fully in U.S. Pat. No. 5,756,290, and in a particularly efficient protocol for wheat described in U.S. Pat. No. 6,153,812, and the references cited therein. Site-specific recombination systems can also be employed to reduce the copy number and random integration of the nucleic acid into the plant genome. For example, the Cre/lox system can be used to immediate lox site-specific recombination in plant cells. This method can be found at least in Choi, et al., Nuc. Acids Res. 28:B19, 2000).

Transgenes:

Molecular biological techniques allow the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes." Several methods for producing transgenic plants have been developed, and the present invention, in particular embodiments, also relates to transformed versions of the genotypes of the invention and/or transformed versions comprising one or more transgenes modify directly or indirectly the expression or activity of at least one phosphatidylcholine:diacylglycerol cholinephosphotransferase (PDCT) (as provided for herein) in one or more seeds or developing seeds of the plant, wherein the level, amount, or distribution of fatty acid unsaturation in the seed oil is modified relative to the seed oil of plants with normal seed expression of the PDCT.

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick, B. R. and Thompson, J. E. Eds. (CRC Press, Inc., Boca Raton, 1993), pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements. Various genetic elements can be introduced into the plant genome using transformation. These elements include but are not limited to genes; coding sequences (in sense or anti-sense orientation); inducible, constitutive, and tissue specific promoters; enhancing sequences; and signal and targeting sequences.

A genetic trait which has been engineered into a particular plant using transformation techniques could be moved into another line using traditional breeding techniques that are well known in the plant breeding arts. For example, a backcrossing approach could be used to move a transgene from a transformed oil seed-bearing plant to an elite plant variety and the resulting progeny would comprise a transgene. As used herein, "crossing" can refer to a simple X by Y cross, or the process of backcrossing, depending on the context. The term "breeding cross" excludes the processes of selfing or sibbing.

With transgenic plants according to the present invention, a foreign protein and/or and modified expression of an endogenous protein or product (e.g., oil) can be produced in commercial quantities. Thus, techniques for the selection and propagation of transformed plants, which are well understood in the art, yield a plurality of transgenic plants which are harvested in a conventional manner, and a plant product can then can be extracted from a tissue of interest or from total biomass. Protein and oil extraction from plant biomass can be accomplished by known methods which are discussed, for example, by Heney and Orr, Anal. Biochem. 114:92-96, 1981.

According to a preferred embodiment, the transgenic plant provided for commercial production of foreign protein is canola (e.g., *Brassica napus* or *B. rapa*), soybean (e.g., *Glycine max*), or sunflower (e.g., *Helianthus annuus*). In another preferred embodiment, the biomass of interest is seed. A genetic map can be generated, primarily via conventional RFLP, PCR, and SSR analysis, which identifies the approximate chromosomal location of the integrated DNA molecule. For exemplary methodologies in this regard, see Glick and Thompson, Methods in Plant Molecular Biology and Biotechnology 269-284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Introduction of Transgenes of Agronomic Interest by Transformation

Agronomic genes can be expressed in transformed plants. For example, plants can be genetically engineered to express various phenotypes of agronomic interest, or, alternatively, transgenes can be introduced into a plant by breeding with a plant that has the transgene. Through the transformation of plant, the expression of genes can be modulated to enhance disease resistance, insect resistance, herbicide resistance, water stress tolerance and agronomic traits as well as seed quality traits. Transformation can also be used to insert DNA sequences which control or help control male-sterility. DNA sequences native to particular plants as well as non-native DNA sequences can be transformed and used to modulate levels of native or non-native proteins. Anti-sense technology, siRNA technology, various promoters, targeting sequences, enhancing sequences, and other DNA sequences can be inserted into the particular genome for the purpose of modulating the expression of proteins. Many exemplary genes implicated in this regard are known in the art.

Variants of Phosphatidylcholine:Diacylglycerol Cholinephosphotransferase (PDCT) Nucleic Acids and Proteins As used herein, a "biological activity" refers to a function of a polypeptide including but not limited to complexation, dimerization, multimerization, receptor-associated ligand binding and/or endocytosis, receptor-associated protease activity, phosphorylation, dephosphorylation, autophosphorylation, ability to form complexes with other molecules, ligand binding, catalytic or enzymatic activity, activation including auto-activation and activation of other polypeptides, inhibition or modulation of another molecule's function, stimulation or inhibition of signal transduction and/or cellular responses such as cell proliferation, migration, differentiation, and growth, degradation, membrane localization, and membrane binding. A biological activity can be assessed by assays described herein and by any suitable assays known to those of skill in the art, including, but not limited to in vitro assays, including cell-based assays, in vivo assays, including assays in animal models for particular diseases.

Preferably, the phosphatidylcholine:diacylglycerol cholinephosphotransferase (PDCT), or variants thereof) comprises an amino acid sequence of SEQ ID NO:3 (or of SEQ ID NO:5 having from 1, to about 3, to about 5, to about 10, or to about 20 conservative amino acid substitutions), or a fragment of a sequence of SEQ ID NO:3 (or of SEQ ID NO:5 having from 1, to about 3, to about 5, to about 10, or to about 20 conservative amino acid substitutions). Preferably, phosphatidylcholine:diacylglycerol cholinephosphotransferase (PDCT), or variant thereof, comprises a sequence of SEQ ID NO:2, or SEQ ID NO:5, or a conservative amino acid substitution variant thereof.

Functional phosphatidylcholine:diacylglycerol cholinephosphotransferase (PDCT), variants are those proteins that display (or lack) one or more of the biological activities of phosphatidylcholine:diacylglycerol cholinephosphotransferase (PDCT).

As used herein, the term "wild type ROD1 or PDCT", means a naturally occurring ROD1 or PDCT allele found within plants which encodes a functional ROD1 or PDCT protein. In contrast, the term "mutant ROD1 or PDCT", as used herein, refers to an ROD1 or PDCT allele, which does not encode a functional ROD1 or PDCT protein, i.e., an ROD1 or PDCT allele encoding a non-functional ROD1 or PDCT protein, which, as used herein, refers to an ROD1 or PDCT protein having no biological activity or a significantly reduced biological activity as compared to the corresponding wild-type functional ROD1 or PDCT protein, or encoding no ROD1 or PDCT protein at all. Such a "mutant ROD1 or PDCT allele" (also called "full knock-out" or "null" allele) is a wild-type ROD1 or PDCT allele, which comprises one or more mutations in its nucleic acid sequence, whereby the mutation(s) preferably result in a significantly reduced (absolute or relative) amount of functional ROD1 or PDCT protein in the cell in vivo. Mutant alleles of the ROD1 or PDCT protein-encoding nucleic acid sequences are designated as "rod1 or pdct" herein. Mutant alleles can be either "natural mutant" alleles, which are mutant alleles found in nature (e.g., produced spontaneously without human application of mutagens) or induced mutant" alleles, which are induced by human intervention, e.g., by mutagenesis.

As used herein, the term "wild type ROD1 or PDCT", means a naturally occurring ROD1 or PDCT allele found within plants which encodes a functional ROD1 or PDCT protein. In contrast, in particular aspects, the term "mutant ROD1 or PDCT", as used herein, refers to an ROD1 or PDCT allele, which does not encode a functional ROD1 or PDCT protein, i.e., an ROD1 or PDCT allele encoding a non-functional ROD1 or PDCT protein, which, as used herein, refers to an ROD1 or PDCT protein having no biological activity or a significantly reduced biological activity as compared to the corresponding wild-type functional ROD1 or PDCT protein, or encoding no ROD1 or PDCT protein at all. Such a "mutant ROD1 or PDCT allele" (also called "full knock-out" or "null" allele) is a wild-type ROD1 or PDCT allele, which comprises one or more mutations in its nucleic acid sequence, whereby the mutation(s) preferably result in a significantly reduced (absolute or relative) amount of functional ROD1 or PDCT protein in the cell in vivo. Mutant alleles of the ROD1 or PDCT protein-encoding nucleic acid sequences are designated as "rod1 or pdct" herein. Mutant alleles can be either "natural mutant" alleles, which are mutant alleles found in nature (e.g., produced spontaneously without human application of mutagens) or induced mutant" alleles, which are induced by human intervention, e.g., by mutagenesis.

Variants of phosphatidylcholine:diacylglycerol cholinephosphotransferase (PDCT) have utility for aspects of the present invention. Variants can be naturally or non-naturally occurring. Naturally occurring variants (e.g., polymorphisms) are found in various species and comprise amino acid sequences which are substantially identical to the amino acid sequence shown in SEQ ID NO:3 or SEQ ID NO:5. Species homologs of the protein can be obtained using subgenomic polynucleotides of the invention, as described below, to make suitable probes or primers for screening cDNA expression libraries from other species, such as mice, monkeys, yeast, or bacteria, identifying cDNAs which encode homologs of the protein, and expressing the cDNAs as is known in the art. Orthologs are provided for herein.

Non-naturally occurring variants which retain (or lack) substantially the same biological activities as naturally occurring protein variants are also included here. Preferably, naturally or non-naturally occurring variants have amino acid sequences which are at least 85%, 90%, 95%, 96%, 97%, 98%, 99% or greater than 99% identical to the amino acid sequence shown in SEQ ID NOS:3 or 5. More preferably, the molecules are at least 98%, 99% or greater than 99% identical. Percent identity is determined using any method known in the art. A non-limiting example is the Smith-Waterman homology search algorithm using an affine gap search with a gap open penalty of 12 and a gap extension penalty of 1. The Smith-Waterman homology search algorithm is taught in Smith and Waterman, *Adv. Appl. Math.* 2:482-489, 1981.

As used herein, "amino acid residue" refers to an amino acid formed upon chemical digestion (hydrolysis) of a polypeptide at its peptide linkages. The amino acid residues described herein are generally in the "L" isomeric form. Residues in the "D" isomeric form can be substituted for any L-amino acid residue, as long as the desired functional property is retained by the polypeptide. NH2 refers to the free amino group present at the amino terminus of a polypeptide. COOH refers to the free carboxy group present at the carboxyl terminus of a polypeptide. In keeping with standard polypeptide nomenclature described in J. Biol. Chem., 243:3552-59 (1969) and adopted at 37 C.F.R. §§ 1.821-1.822, abbreviations for amino acid residues are shown in Table 2:

TABLE 2

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | Asparagines |
| B | Asx | Asn and/or Asp |
| C | Cys | Cysteine |
| X | Xaa | Unknown or other |

It should be noted that all amino acid residue sequences represented herein by a formula have a left to right orientation in the conventional direction of amino-terminus to carboxyl-terminus. In addition, the phrase "amino acid residue" is defined to include the amino acids listed in the Table of Correspondence and modified and unusual amino acids, such as those referred to in 37 C.F.R. §§ 1.821-1.822, and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxyl-terminal group such as COOH.

Guidance in determining which amino acid residues can be substituted, inserted, or deleted without abolishing biological or immunological activity can be found using computer programs well known in the art, such as DNASTAR software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids. Preferably, amino acid changes in the phosphatidylcholine:diacylglycerol cholinephosphotransferase (PDCT) polypeptide variants are conservative amino acid changes, i.e., substitutions of similarly charged or uncharged amino acids.

It is reasonable to expect that an isolated replacement of a leucine with an isoleucine or valine, an aspartate with a glutamate, a threonine with a serine, or a similar replacement of an amino acid with a structurally related amino acid will not have a major effect on the biological properties of the resulting variant. Properties and functions of phosphatidylcholine:diacylglycerol cholinephosphotransferase (PDCT) polypeptide protein or polypeptide variants are of the same type as a protein comprising the amino acid sequence encoded by the nucleotide sequence shown in SEQ ID NOS:3 and 5, although the properties and functions of variants can differ in degree.

Variants of the phosphatidylcholine:diacylglycerol cholinephosphotransferase (PDCT) polypeptide disclosed herein include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do or do not affect functional activity of the proteins are also variants. Covalent variants can be prepared by linking functionalities to groups which are found in the amino acid chain or at the N- or C-terminal residue, as is known in the art.

A subset of mutants, called muteins, is a group of polypeptides in which neutral amino acids, such as serines, are substituted for cysteine residues which do not participate in disulfide bonds. These mutants may be stable over a broader temperature range than native secreted proteins (see, e.g., Mark, et al., U.S. Pat. No. 4,959,314).

It will be recognized in the art that some amino acid sequences of the phosphatidylcholine:diacylglycerol cholinephosphotransferase (PDCT) polypeptides of the invention can be varied without significant effect on the structure or function of the protein. If such differences in sequence are contemplated, it should be remembered that there are critical areas on the protein which determine activity. In general, it is possible to replace residues that form the tertiary structure, provided that residues performing a similar function are used. In other instances, the type of residue may be completely unimportant if the alteration occurs at a non-critical region of the protein. The replacement of amino acids can also change the selectivity of ligand binding to cell surface receptors (Ostade, et al., *Nature* 361:266-268, 1993). Thus, the phosphatidylcholine:diacylglycerol cholinephosphotransferase (PDCT) polypeptides of the present invention may include one or more amino acid substitutions, deletions or additions, either from natural mutations or human manipulation.

Amino acids in the phosphatidylcholine:diacylglycerol cholinephosphotransferase (PDCT) polypeptides of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as binding to a natural or synthetic binding partner. Sites that are critical for ligand-receptor binding can also be determined by structural analysis such as crystallization, nuclear magnetic resonance or photoaffinity labeling (Smith, et al., *J. Mol. Biol.* 224:899-904 (1992) and de Vos, et al. *Science* 255:306-312 (1992)).

As indicated, changes in particular aspects are preferably of a minor nature, such as conservative amino acid substitutions that do not significantly affect the folding or activity of the protein. Of course, the number of amino acid substitutions a skilled artisan would make depends on many factors, including those described above. Other embodiments comprise non-conservative substitutions. Generally speaking, the number of substitutions for any given phosphatidylcholine:diacylglycerol cholinephosphotransferase (PDCT) polypeptide will not be more than 50, 40, 30, 25, 20, 15, 10, 5, or 3.

Fusion Proteins

Fusion proteins comprising proteins or polypeptide fragments of phosphatidylcholine:diacylglycerol cholinephosphotransferase (PDCT) polypeptide can also be constructed. Fusion proteins are useful for generating antibodies against amino acid sequences and for use in various targeting and assay systems. For example, fusion proteins can be used to identify proteins which interact with a phosphatidylcholine:diacylglycerol cholinephosphotransferase (PDCT) polypeptide of the invention or which interfere with its biological function. Physical methods, such as protein affinity chromatography, or library-based assays for protein-protein interactions, such as the yeast two-hybrid or phage display systems, can also be used for this purpose. Such methods are well known in the art and can also be used as drug screens. Fusion proteins comprising a signal sequence can be used.

A fusion protein comprises two protein segments fused together by means of a peptide bond. Amino acid sequences for use in fusion proteins of the invention can be utilize the amino acid sequence shown in SEQ ID NOS:3 or 5, or can be prepared from biologically active variants of SEQ ID NOS:3 or 5, such as those described above. The first protein segment can include of a full-length phosphatidylcholine:diacylglycerol cholinephosphotransferase (PDCT) polypeptide. Other first protein segments can consist of about functional portions of SEQ ID NOS:3 and 5.

The second protein segment can be a full-length protein or a polypeptide fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and virus protein fusions.

These fusions can be made, for example, by covalently linking two protein segments or by standard procedures in the art of molecular biology. Recombinant DNA methods can be use to prepare fusion proteins, for example, by making a DNA construct which comprises a coding region for the protein sequence of SEQ ID NOS:3 and 5 in proper reading frame with a nucleotide encoding the second protein segment and expressing the DNA construct in a host cell, as is known in the art. Many kits for constructing fusion proteins are available from companies that supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Nucleic Acid Sequences Encoding Mutant ROD1 or PDCT Proteins

Nucleic acid sequences comprising one or more nucleotide deletions, insertions or substitutions relative to the wild type nucleic acid sequences are another embodiment of the invention, as are fragments of such mutant nucleic acid molecules. Such mutant nucleic acid sequences (referred to as ROD1 or PDCT sequences) can be generated and 1 identified using various known methods, as described further below. Again, such nucleic acid molecules are provided both in endogenous form and in isolated form. In one embodiment, the mutation(s) result in one or more changes (deletions, insertions and/or substitutions) in the amino acid sequence of the encoded ROD1 or PDCT protein (i.e., it is not a "silent mutation"). In another embodiment, the mutation(s) in the nucleic acid sequence result in a significantly reduced or completely abolished biological activity of the encoded ROD1 or PDCT protein relative to the wild type protein.

The nucleic acid molecules may, thus, comprise one or more mutations, such as:

(a) a "missense mutation", which is a change in the nucleic acid sequence that results in the substitution of an amino acid for another amino acid;

(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.

(c) an "insertion mutation" of one or more amino acids, due to one or more codons having been added in the coding sequence of the nucleic acid;

(d) a "deletion mutation" of one or more amino acids, due to one or more codons having been deleted in the coding sequence of the nucleic acid;

(e) a "frameshift mutation", resulting in the nucleic acid sequence being translated in a different frame downstream of the mutation. A frameshift mutation can have various causes, such as the insertion, deletion or duplication of one or more nucleotides.

It is desired that the mutation(s) in the nucleic acid sequence preferably result in a mutant protein comprising significantly reduced or no biological activity in vivo or in the production of no protein. Basically, any mutation which results in a protein comprising at least one amino acid insertion, deletion and/or substitution relative to the wild type protein can lead to significantly reduced or no biological activity. It is, however, understood that mutations in certain parts of the protein are more likely to result in a reduced function of the mutant ROD1 or PDCT protein, such as mutations leading to truncated proteins, whereby significant portions of the functional domains are lacking.

Thus in one embodiment, nucleic acid sequences comprising one or more of any of the types of mutations described above are provided. In another embodiment, ROD1 or PDCT sequences comprising one or more stop codon (nonsense) mutations, one or more missense mutations and/or one or more frameshift mutations are provided. Any of the above mutant nucleic acid sequences are provided per se (in isolated form), as are plants and plant parts comprising such sequences endogenously. In the tables herein below the most preferred ROD1 or PDCT alleles are described.

A nonsense mutation in an ROD1 or PDCT allele, as used herein, is a mutation in an ROD1 or PDCT allele whereby one or more translation stop codons are introduced into the coding DNA and the corresponding mRNA sequence of the corresponding wild 1 type ROD1 or PDCT allele. Translation stop codons are TGA (UGA in the mRNA), TAA (UAA) and TAG (UAG). Thus, any mutation (deletion, insertion or substitution) that leads to the generation of an in-frame stop codon in the coding sequence will result in termination of translation and truncation of the amino acid chain. In one embodiment, a mutant ROD1 or PDCT allele comprising a nonsense mutation is an ROD1 or PDCT allele wherein an in-frame stop codon is introduced in the ROD1 or PDCT codon sequence by a single nucleotide substitution, such as the mutation of CAG to TAG, TGG to TAG, TGG to TGA, or CAA to TAA. In another embodiment, a mutant ROD1 or PDCT allele comprising a nonsense mutation is an ROD1 or PDCT allele wherein an in-frame stop codon is introduced in the ROD1 or PDCT codon sequence by double nucleotide substitutions, such as the mutation of CAG to TAA, TGG to TAA, or CGG to TAG or TGA. In yet another embodiment, a mutant ROD1 or PDCT allele comprising a nonsense mutation is an ROD1 or PDCT allele wherein an in-frame stop codon is introduced in the ROD1 or PDCT codon sequence by triple nucleotide substitutions, such as the mutation of CGG to TAA. The truncated protein lacks the amino acids encoded by the coding DNA downstream of the mutation (i.e., the C-terminal part of the ROD1 or PDCT protein) and maintains the amino acids encoded by the coding DNA upstream of the mutation (i.e., the N-terminal part of the ROD1 or PDCT protein).

The Tables herein below describe a range of possible nonsense mutations in the ROD1 or PDCT sequences provided herein:

TABLE 1a

Potential STOP codon mutations in At-ROD1 (SEQ ID NO: 1)

| gene | position | position | initial codon | stop_codon |
| --- | --- | --- | --- | --- |
| At_rod 1 | 199 | 201 | TGG | TAG |
| At_rod 1 | 199 | 201 | TGG | TAA |
| At_rod 1 | 199 | 201 | TGG | TGA |
| At_rod 1 | 226 | 228 | TGG | TGA |
| At_rod 1 | 226 | 228 | TGG | TAG |
| At_rod 1 | 226 | 228 | TGG | TAA |
| At_rod 1 | 265 | 267 | TGG | TGA |
| At_rod 1 | 265 | 267 | TGG | TAA |
| At_rod 1 | 265 | 267 | TGG | TAG |
| At_rod 1 | 325 | 327 | CAG | TAG |
| At_rod 1 | 325 | 327 | CAG | TAA |
| At_rod 1 | 457 | 459 | CAA | TAA |
| At_rod 1 | 475 | 477 | TGG | TAA |
| At_rod 1 | 475 | 477 | TGG | TAG |
| At_rod 1 | 475 | 477 | TGG | TGA |
| At_rod 1 | 481 | 483 | TGG | TAG |
| At_rod 1 | 481 | 483 | TGG | TGA |
| At_rod 1 | 481 | 483 | TGG | TAA |

TABLE 1a-continued

Potential STOP codon mutations in At-ROD1 (SEQ ID NO: 1)

| gene | position | position | initial codon | stop_codon |
| --- | --- | --- | --- | --- |
| At_rod 1 | 496 | 498 | CGA | TGA |
| At_rod 1 | 496 | 498 | CGA | TAA |
| At_rod 1 | 502 | 504 | CGA | TGA |
| At_rod 1 | 502 | 504 | CGA | TAA |
| At_rod 1 | 562 | 564 | CAG | TAA |
| At_rod 1 | 562 | 564 | CAG | TAG |
| At_rod 1 | 577 | 579 | CAG | TAG |
| At_rod 1 | 577 | 579 | CAG | TAA |
| At_rod 1 | 691 | 693 | CAG | TAG |
| At_rod 1 | 691 | 693 | CAG | TAA |
| At_rod 1 | 736 | 738 | CAG | TAG |
| At_rod 1 | 736 | 738 | CAG | TAA |

TABLE 2b

Potential STOP codon mutations in ROD1 orthologue from *Brassica napus* (SEQ ID NO: 19)

| position | position | initial codon | stop_codon |
| --- | --- | --- | --- |
| 166 | 168 | TGG | TGA |
| 166 | 168 | TGG | TAG |
| 166 | 168 | TGG | TAA |
| 205 | 207 | TGG | TGA |
| 205 | 207 | TGG | TAA |
| 205 | 207 | TGG | TAG |
| 265 | 267 | CAG | TAG |
| 265 | 267 | CAG | TAA |
| 397 | 399 | CAA | TAA |
| 415 | 417 | TGG | TAG |
| 415 | 417 | TGG | TGA |
| 415 | 417 | TGG | TAA |
| 421 | 423 | TGG | TAG |
| 421 | 423 | TGG | TGA |
| 421 | 423 | TGG | TAA |
| 442 | 444 | CGA | TGA |
| 442 | 444 | CGA | TAA |
| 502 | 504 | CAG | TAA |
| 502 | 504 | CAG | TAG |
| 517 | 519 | CAG | TAG |
| 517 | 519 | CAG | TAA |
| 631 | 633 | CAG | TAA |
| 631 | 633 | CAG | TAG |
| 676 | 678 | CAA | TAA |

Obviously, mutations are not limited to the ones shown in the above tables and it is understood that analogous STOP mutations may be present in ROD1 or PDCT alleles other than those depicted in the sequence listing and referred to in the tables above.

A missense mutation in an ROD1 or PDCT allele, as used herein, is any mutation (deletion, insertion or substitution) in an ROD1 or PDCT allele whereby one or more codons are changed in the coding DNA and the corresponding mRNA sequence of the corresponding wild type ROD1 or PDCT allele, resulting in the substitution of one or more amino acids in the wild type ROD1 or PDCT protein for one or more other amino acids in the mutant ROD1 or PDCT protein.

A frameshift mutation in an ROD1 or PDCT allele, as used herein, is a mutation (deletion, insertion, duplication, and the like) in an ROD1 or PDCT allele that results in the nucleic acid sequence being translated in a different frame downstream of the mutation.

Downregulation of ROD1:

Several methods are available in the art to produce a silencing RNA molecule, i.e., an RNA molecule which when expressed reduces the expression of a particular gene or group of genes, including the so-called "sense" or "antisense" RNA technologies.

Antisense Technology.

Thus in one embodiment, the inhibitory RNA molecule encoding chimeric gene is based on the so-called antisense technology. In other words, the coding region of the chimeric gene comprises a nucleotide sequence of at least 19 or 20 consecutive nucleotides of the complement of the nucleotide sequence of the ROD1 or an orthologue thereof. Such a chimeric gene may be constructed by operably linking a DNA fragment comprising at least 19 or 20 nucleotides from ROD1 encoding gene or an orthologue thereof, isolated or identified as described elsewhere in this application, in inverse orientation to a plant expressible promoter and 3' end formation region involved in transcription termination and polyadenylation.

Co-Suppression Technology.

In another embodiment, the inhibitory RNA molecule encoding chimeric gene is based on the so-called co-suppression technology. In other words, the coding region of the chimeric gene comprises a nucleotide sequence of at least 19 or 20 consecutive nucleotides of the nucleotide sequence of the ROD1 encoding gene or an orthologue thereof (or in some embodiments, the fiber selective β-1,3 endoglucanase gene). Such a chimeric gene may be constructed by operably linking a DNA fragment comprising at least 19 or 20 nucleotides from the ROD1 encoding gene or an orthologue thereof, in direct orientation to a plant expressible promoter and 3' end formation region involved in transcription termination and polyadenylation.

The efficiency of the above mentioned chimeric genes in reducing the expression of the the ROD1 encoding gene or an orthologue thereof may be further enhanced by the inclusion of DNA element which result in the expression of aberrant, unpolyadenylated inhibitory RNA molecules or results in the retention of the inhibitory RNA molecules in the nucleus of the cells. One such DNA element suitable for that purpose is a DNA region encoding a self-splicing ribozyme, as described in PCT/IB2000/01133, published as WO 2001/012824 (incorporated herein by reference in its entirety and particularly for its teachings on self-splicing ribozymes). Another such DNA element suitable for that purpose is a DNA region encoding an RNA nuclear localization or retention signal, as described in PCT/AU2003/00292, published as WO 2003/076619 (incorporated by reference).

Double-Stranded RNA (dsRNA) or Interfering RNA (RNAi).

A convenient and very efficient way of downregulating the expression of a gene of interest uses so-called double-stranded RNA (dsRNA) or interfering RNA (RNAi), as described e.g., in WO 1999/53050 (incorporated herein by reference in its entirety and particularly for its teachings on RNAi)). In this technology, an RNA molecule is introduced into a plant cell, whereby the RNA molecule is capable of forming a double stranded RNA region over at least about 19 to about 21 nucleotides, and whereby one of the strands of this double stranded RNA region is about identical in nucleotide sequence to the target gene ("sense region"), whereas the other strand is about identical in nucleotide sequence to the complement of the target gene or of the sense region ("antisense region"). It is expected that for silencing of the target gene expression, the nucleotide sequence of the 19 consecutive nucleotide sequences may have one mismatch, or the sense and antisense region may differ in one nucleotide. To achieve the construction of such RNA molecules or the encoding chimeric genes, use can be made of the vector as described in WO 2002/059294.

Thus, in one embodiment of the invention, a method for regulating fatty acid unsaturation in seed oil, is provided comprising the step of introducing a chimeric gene into a cell of the plant, wherein the chimeric gene comprises the following operably linked DNA elements:

(a) a plant expressible promoter;
(b) a transcribed DNA region, which when transcribed yields a double-stranded RNA molecule capable of reducing specifically the expression of ROD1 or an orthologue thereof, and the RNA molecule comprising a first and second RNA region wherein
   i) the first RNA region comprises a nucleotide sequence of at least 19 consecutive nucleotides having at least about 94% sequence identity to the nucleotide sequence of ROD1 or of an orthologue thereof;
   ii) the second RNA region comprises a nucleotide sequence complementary to the at least 19 consecutive nucleotides of the first RNA region;
   iii) the first and second RNA region are capable of base-pairing to form a double stranded RNA molecule between at least the 19 consecutive nucleotides of the first and second region; and
(c) a 3' end region comprising transcription termination and polyadenylation signals functioning in cells of the plant.

The length of the first or second RNA region (sense or antisense region) may vary from about 19 nucleotides (nt) up to a length equaling the length (in nucleotides) of the endogenous gene involved in callose removal. The total length of the sense or antisense nucleotide sequence may thus be at least at least 25 nt, or at least about 50 nt, or at least about 100 nt, or at least about 150 nt, or at least about 200 nt, or at least about 500 nt. It is expected that there is no upper limit to the total length of the sense or the antisense nucleotide sequence. However for practical reasons (such as e.g., stability of the chimeric genes) it is expected that the length of the sense or antisense nucleotide sequence should not exceed 5000 nt, particularly should not exceed 2500 nt and could be limited to about 1000 nt.

It will be appreciated that the longer the total length of the sense or antisense region, the less stringent the requirements for sequence identity between these regions and the corresponding sequence in ROD1 gene and orthologues or their complements. Preferably, the nucleic acid of interest should have a sequence identity of at least about 75% with the corresponding target sequence, particularly at least about 80%, more particularly at least about 85%, quite particularly about 90%, especially about 95%, more especially about 100%, quite especially be identical to the corresponding part of the target sequence or its complement. However, it is preferred that the nucleic acid of interest always includes a sequence of about 19 consecutive nucleotides, particularly about 25 nt, more particularly about 50 nt, especially about 100 nt, quite especially about 150 nt with 100% sequence identity to the corresponding part of the target nucleic acid. Preferably, for calculating the sequence identity and designing the corresponding sense or antisense sequence, the number of gaps should be minimized, particularly for the shorter sense sequences.

dsRNA encoding chimeric genes according to the invention may comprise an intron, such as a heterologous intron, located e.g., in the spacer sequence between the sense and antisense RNA regions in accordance with the disclosure of WO 1999/53050 (incorporated herein by reference).

Synthetic Micro-RNAs (miRNAs).

The use of synthetic micro-RNAs to downregulate expression of a particular gene in a plant cell, provides for very high sequence specificity of the target gene, and thus allows conveniently to discriminate between closely related alleles as target genes the expression of which is to be downregulated.

Thus, in another embodiment of the invention, the biologically active RNA or silencing RNA or inhibitory RNA molecule may be a microRNA molecule, designed, synthesized and/or modulated to target and cause the cleavage ROD1 encoding gene or an orthologue thereof in a plant. Various methods have been described to generate and use miRNAs for a specific target gene (including but not limited to Schwab, et al. (2006, Plant Cell, 18(5):1121-1133), WO 2006/044322, WO 2005/047505, EP 06009836, all incorporated herein by reference in their entirety, and particularly for their respective teachings relating to miRNA). Usually, an existing miRNA scaffold is modified in the target gene recognizing portion so that the generated miRNA now guides the RISC complex to cleave the RNA molecules transcribed from the target nucleic acid. miRNA scaffolds could be modified or synthesized such that the miRNA now comprises 21 consecutive nucleotides of the ROD1 encoding nucleotide sequence or an orthologue thereof, such as the sequences represented in the Sequence listing, and allowing mismatches according to the herein below described rules.

Thus, in one embodiment, the invention provides a method for regulation of fatty acid unsaturation in seed oil comprising the steps of:
  a. Introducing a chimeric gene into cells of an oilseed bearing plant, said chimeric gene comprising the following operably linked DNA regions:
    i. a plant expressible promoter;
    ii. a DNA region which upon introduction and transcription in a plant cell is processed into a miRNA, whereby the miRNA is capable of recognizing and guiding the cleavage of the mRNA of a ROD1 encoding gene or an orthologue thereof of the plant; and
    iii. optionally, a 3' DNA region involved in transcription termination and polyadenylation.

The mentioned DNA region processed into a miRNA may comprise a nucleotide sequence which is essentially complementary to a nucleotide sequence of at least 21 consecutive nucleotides of a ROD1 encoding gene or orthologue, provided that one or more of the following mismatches are allowed:
  a. A mismatch between the nucleotide at the 5' end of the miRNA and the corresponding nucleotide sequence in the RNA molecule;
  b. A mismatch between any one of the nucleotides in position 1 to position 9 of the miRNA and the corresponding nucleotide sequence in the RNA molecule; and/or
  c. Three mismatches between any one of the nucleotides in position 12 to position 21 of the miRNA and the corresponding nucleotide sequence in the RNA molecule provided that there are no more than two consecutive mismatches.

As used herein, a "miRNA" is an RNA molecule of about 20 to 22 nucleotides in length which can be loaded into a RISC complex and direct the cleavage of another RNA molecule, wherein the other RNA molecule comprises a nucleotide sequence essentially complementary to the nucleotide sequence of the miRNA molecule whereby one or more of the following mismatches may occur:
  d. A mismatch between the nucleotide at the 5' end of said miRNA and the corresponding nucleotide sequence in the target RNA molecule;
  e. A mismatch between any one of the nucleotides in position 1 to position 9 of said miRNA and the corresponding nucleotide sequence in the target RNA molecule;
  f. Three mismatches between any one of the nucleotides in position 12 to position 21 of said miRNA and the corresponding nucleotide sequence in the target RNA molecule provided that there are no more than two consecutive mismatches; and/or
  g. No mismatch is allowed at positions 10 and 11 of the miRNA (all miRNA positions are indicated starting from the 5' end of the miRNA molecule).

A miRNA is processed from a "pre-miRNA" molecule by proteins, such as DicerLike (DCL) proteins, present in any plant cell and loaded onto a RISC complex where it can guide the cleavage of the target RNA molecules.

As used herein, a "pre-miRNA" molecule is an RNA molecule of about 100 to about 200 nucleotides, preferably about 100 to about 130 nucleotides which can adopt a secondary structure comprising a double stranded RNA stem and a single stranded RNA loop and further comprising the nucleotide sequence of the miRNA (and its complement sequence) in the double stranded RNA stem. Preferably, the miRNA and its complement are located about 10 to about 20 nucleotides from the free ends of the miRNA double stranded RNA stem. The length and sequence of the single stranded loop region are not critical and may vary considerably, e.g., between 30 and 50 nt in length. Preferably, the difference in free energy between unpaired and paired RNA structure is between −20 and −60 kcal/mole, particularly around −40 kcal/mole. The complementarity between the miRNA and the miRNA* need not be perfect and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

Naturally occurring miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds.

The pre-miRNA molecules (and consequently also the miRNA molecules) can be conveniently introduced into a plant cell by providing the plant cells with a gene comprising a plant-expressible promoter operably linked to a DNA region, which when transcribed yields the pre-miRNA molecule. The plant expressible promoter may be the promoter naturally associated with the pre-miRNA molecule or it may be a heterologous promoter.

Example 1

Materials and Methods

Plant Materials.

Mutant line rod1 in the *Arabidopsis thaliana* Col-0 background was isolated from an M3 population of about 3,000 plants after mutagenesis with ethyl methanesulfonate by directly analyzing the fatty acid composition of seed samples by gas chromatography (1). Plants were grown on soil in controlled environment chambers at 22° C. under continuous florescent illumination (150 µmol quanta/m$^2$/s).

Fatty Acid and Lipid Analysis.

The overall fatty acid compositions of seeds and other tissues were determined as described (2). Pulse-chase labeling was carried out in developing seeds harvested from siliques nine days after flowering. The seeds were pulsed with [1-$^{14}$C]glycerol or [1-$^{14}$C]acetate for 15 min. After labeling, the tissues were chased with unlabelled acetate or glycerol. At different time intervals, total lipids were extracted and analyzed in silica-TLC and the radioactivity in PC, DG and TG determined by scintillation counting as described (3).

Genetic Analysis and Map-Based Cloning of ROD1.

To determine the genetic basis of the rod1 mutation, rod1 plants were crossed to Col-0 wild-type (WT). F1 seeds showed a fatty acid profile similar to that of the WT parent. F1 plants were grown and allowed to self. Of 263 F2 plants analyzed, 69 had seed fatty acid profile similar to original rod1 seeds, while the remaining 194 had fatty acid compositions similar to WT. This pattern of segregation is a good fit to the hypothesized 3:1 ratio ($\chi^2$=0.21, p>0.05).

Figures 2A, 2B, 2C, 2D:
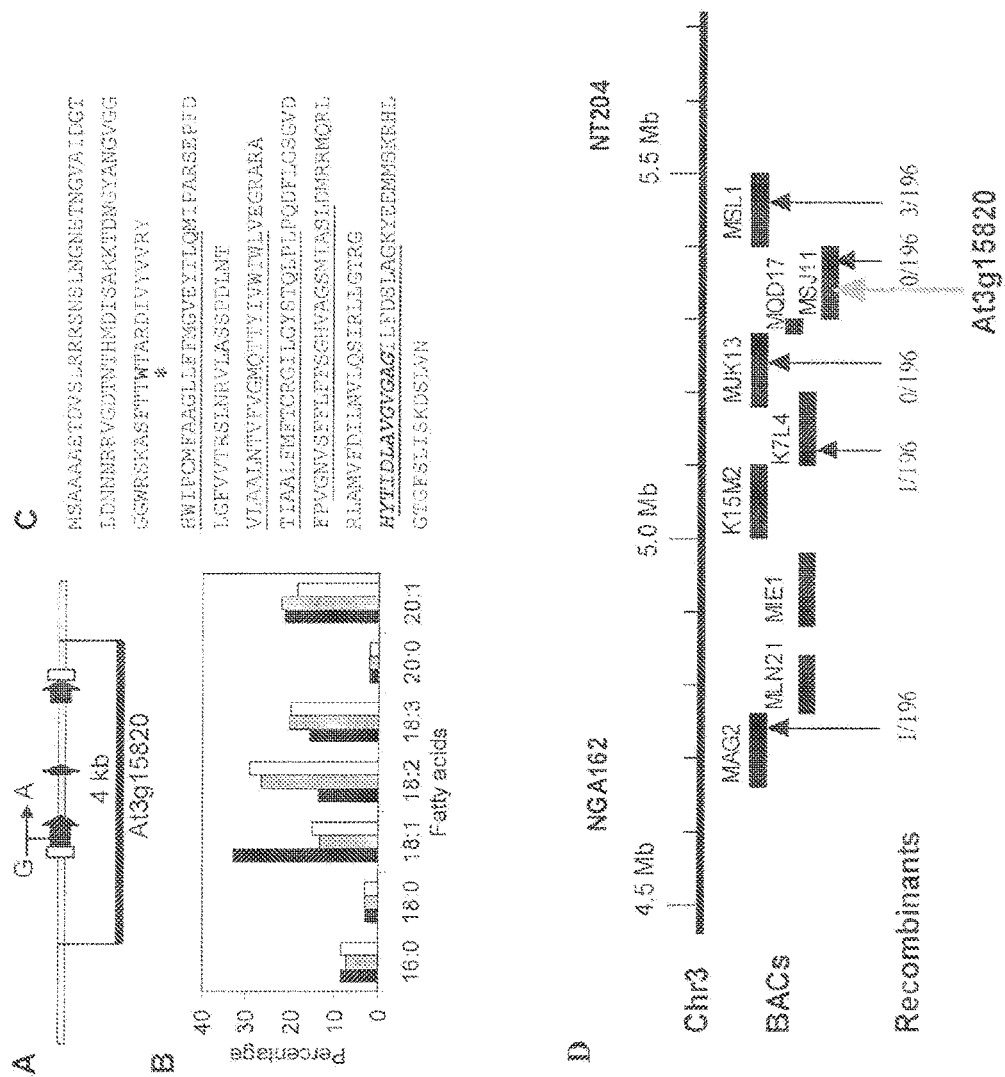
FIGS. 2A-2C show that the ROD1 gene was identified as At3g15820 in *Arabidopsis*.
FIG. 2D shows map-based identification of the ROD1 Locus on *Arabidopsis* chromosome 3.

The rod1 locus was identified by map-based cloning using 800 F2 plants derived from a cross between rod1 mutant and the Landsberg erecta WT. Initial screening by bulk segregant analysis of a set of 20 simple sequence length polymorphism (SSLP) markers that are evenly distributed in the *Arabidopsis* genome (4) resulted in the linkage of rod1 to the marker NGA162 in chromosome 3 (FIG. 2D). To fine map the rod1 locus, 196 individual F2 plants were identified that were homozygous at the rod1 locus indicated by increased 18:1 in seed fatty acid composition. Segregation analysis using available polymorphic SSLP markers vicinity of NGA162 delimited the rod1 mutation to an interval between NGA162 and NT204. More polymorphic markers were then designed using PCR primers, and subsequently located the rod1 locus in the region of chromosome 3 covered by BAC clones MJK13, MQD17 and MSJ11 (FIG. 2D).

Within this region, eight genes were annotated as encoding proteins with known or possible functions in lipid metabolism. After considering published information (5, 6), Applicants amplified, by PCR, rod1 genomic DNA corresponding to six of the genes, including At3g15820. A G→A transition was identified in this gene that is predicted to change Trp$^{76}$ to a stop codon. The remaining five genes showed no changes from WT.

To confirm At3g15820 as the ROD1 locus, a PCR fragment of 3,961 bp containing the At3g15820 gene was amplified using genomic DNA extracted from Col-0 WT plants. This genomic fragment was cloned into a binary vector pGate-Phas-DsRed at the AflII and EcoRI sites (2) and then transferred into *Agrobacterium tumefaciens* strain GV3101 (pMP90) for transformation of the rod1 mutant plants. Transformants were selected based on DsRed expression (7). Fatty acyl methyl esters derived from individual seeds of ten red transgenic seeds and three brown non-transgenic seeds were used to determine seed fatty acid composition using gas chromatography.

Figure 7:
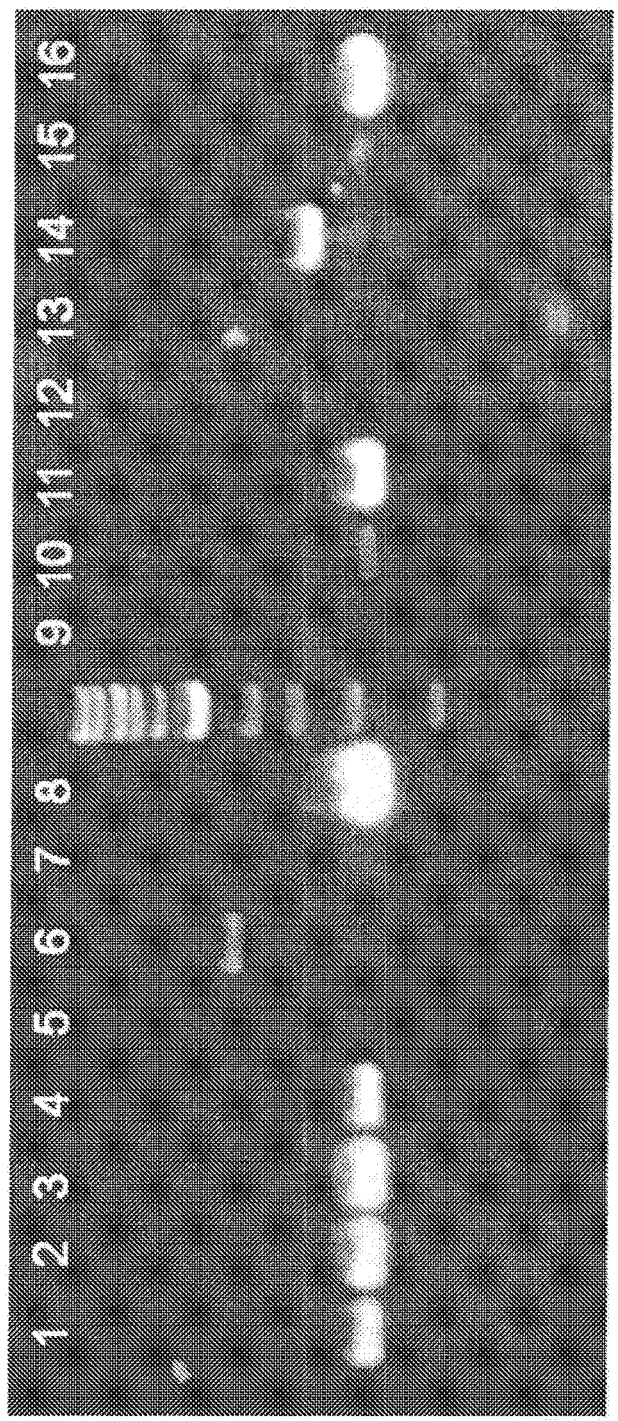
FIG. 7 shows, according to particular exemplary aspects, RT-PCR of ROD1 and At3g15830 expression in *Arabidopsis* and yeast cells. Lanes 1-8 are results for ROD1, and lanes 9-16 are for At3g15830. RT-PCR samples are total RNA from germinating seedlings (1,9), young leaves (2, 10), flowers (3,11), siliques (4, 12) of WT *Arabidopsis* and siliques from rod1 mutant plants (5, 13); yeast cells containing p424GPD (7, 15) or p424ROD1 (8) and p424-At3g15830 (16); and genomic DNA from rod1 (6, 14)

ROD1 enzyme activity assays. The ROD1 open reading frame was amplified by PCR and cloned into the p424GPD yeast expression vector (8) for expression in *Saccharomyces cerevisiae* under control of the glyceraldehydes-phosphate dehydrogenase promoter. The resulting construct p424ROD1 and the empty p424GPD vector were transformed separately into the cells of HJ091 (cpt1::LEU2, ept1$^-$) kindly provided by Dr. C. McMaster (Dalhousie University, NS, Canada). Expression of ROD1 transcripts was confirmed by RT-PCR (FIG. 7).

Yeast cells were inoculated from overnight cultures and grown to mid-log phase (OD$_{600}$=0.5-1.5) by rotary shaking at 30° C. in liquid synthetic minimal media lacking uracil and tryptophan supplemented with 2% glucose (Clontech, Mountain View, Calif.). To prepare microsomes, yeast cells were harvested by centrifugation for 10 min at 1,000 g. The cell pellet was washed once with sterile water and resuspended in ice-cold GTE buffer (20% glycerol, 50 mM Tris-HCl (pH 7.4), 1 mM EDTA) to prepare the membrane fraction using glass beads as described (9). CDP-Choline: diacylglycerol cholinephosphotransferase (CPT) assays (reactions in FIG. 9A) were conducted as described (9) using 0.1 mol diolein and 1 nmol [$^{14}$C]CDP-choline as substrates.

The phosphatidylcholine: diacylglycerol cholinephosphotransferase (PDCT) activities in membrane preparations of HJ091 cells transformed with p424GPD (mock) or p424ROD1 were determined as the amount of [$^{14}$C]dioleoyl-PC produced from [$^{14}$C-Glycerol]diolein (reaction A) or [$^{14}$C-Choline]dimyristyl-phosphatidylcholine (reaction B). The substrates of 1.8 nmol (200,000 cpm) [$^{14}$C-Glycerol]diolein (American Radiolabeled Chemicals, St. Louis, Mo.) and 0.1 µmol dioleoyl-PC (reaction A) or 0.1 µmol diolein and 1 µmol [$^{14}$C-Choline]di-14:0-PC and 0.1 µmol dioleoyl-PC (reaction B) were dried under nitrogen gas and resuspended in 50 µl 4× reaction buffer (final concentrations: 50 mM MOPS/NaOH pH 7.5, 20 mM MgCl$_2$, 0.45% Triton X-100) with the aid of a sonicating bath (9). Reactions (200 µl) were started by adding 20-250 µg of microsomal proteins suspended in the GTE buffer. Unless otherwise indicated, assays were incubated at 15° C. for 15 min and were terminated by the addition of 3 ml of chloroform/ethanol (2:1, v/v) followed by 1.5 ml of 0.9% KCl. Tubes were mixed by vortexing and phase separation was facilitated by centrifugation at 2000 g for 2 min. The aqueous phase was aspirated and the organic phase was washed twice with 1.5 ml of 40% (v/v) ethanol. Samples were analyzed by TLC on silica gel plates in a solvent system of chloroform/methanol/water (65:25:4, by vol.) followed by phosphorimager analysis or radioautography. Corresponding bands were scraped and radio activities were determined by scintillation counting.

Expression of ROD1 and At3g15830.

Figure 8:
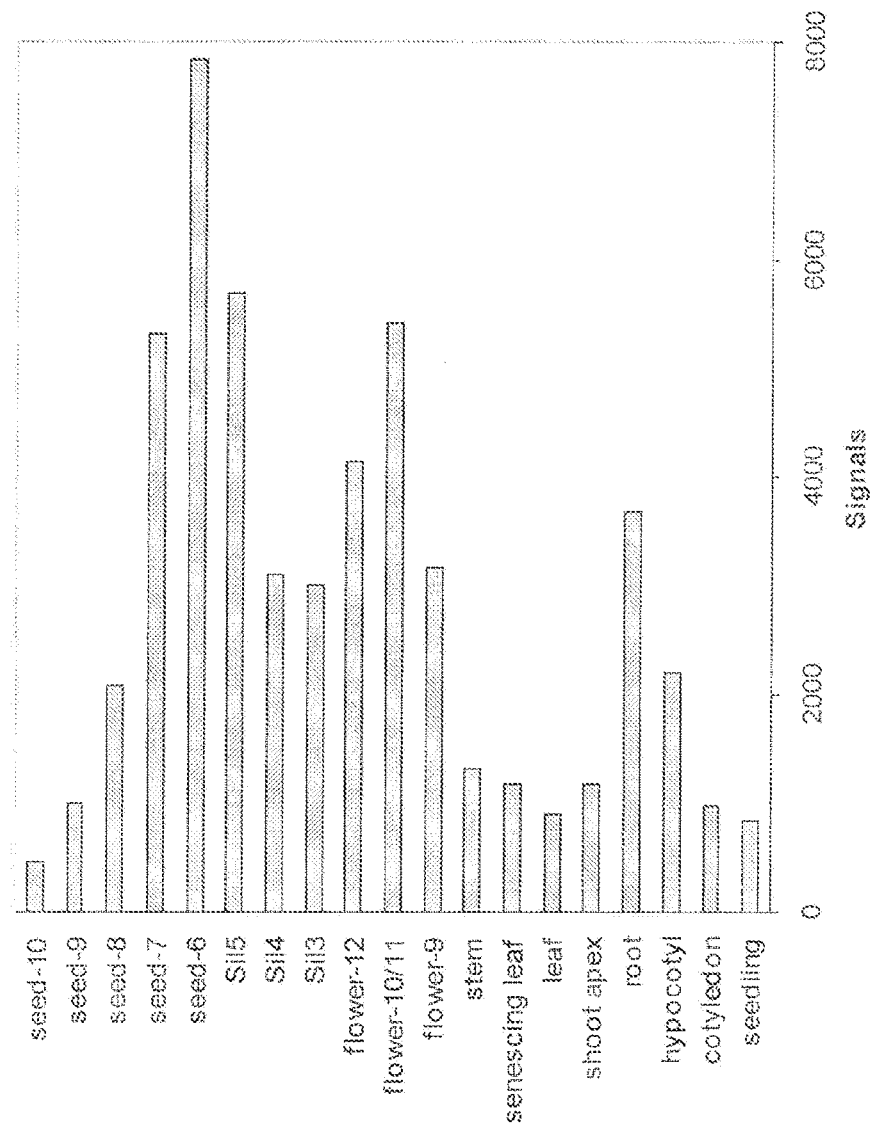
FIG. 8 shows, according to particular exemplary aspects, digital Northern Analysis of ROD1 Gene in *Arabidopsis*. Data used to create the digital Northern were obtained from AtGenExpress at the Genevestigator site (genevestigator.ethz.ch/). Signal intensities were averaged for all the stages that are included in this figure.

Expression data for ROD1 (affymetrixarrayelement258249_s_at) database is shown in FIG. 8. The same array element also detects transcript of a second gene, At3g15830, but data from the *Arabidopsis* Massively Parallel Signal Sequence (MPSS) database (mpss.udel.edu/at/) indicates that this second gene is only expressed in floral tissues (data not shown). To confirm these data, Applicants prepared RNA from germinating seedlings, rosette leaves, flowers and green siliques of WT plants, as well as green siliques of Rod1 mutant plants. Using oligonucleotide primers specific for ROD1 and At3g15830, reverse-transcriptase PCR (RT-PCR) was performed on each of the RNA samples using the Superscript III one-step system, according to the manufacturer's instructions (Invitrogen, Carlsbad, Calif.). The results shown in FIG. 7 indicate that expression of At3g15830 is restricted to the flowers and that transcript of this gene could not be detected in developing siliques of either WT or rod1 plants. To test if At3g15830 also had a PDCT activity, a cDNA was cloned into the p424GPD vector as described above. The resulting construct p424-At3g15830 was then transformed into HJ091 and its expression was confirmed by RT-PCR (FIG. 7, lane 16). PDCT assays using the same reaction conditions for ROD1 yielded no radiolabeled PC indicating that the At3g15830 protein does not have PDCT activity (data not shown).

Phylogenic Analyses.

The methods for producing the parsimony bootstrap tree (10) involved 1000 bootstrap replicate data sets each analyzed using tree bisection reconnection, steepest decent, and other settings to maximize the detection of global optima or the maxmimization of the parsimony optimality criteria.

The methods for producing the Bayesian consensus tree (11) included prior settings for the most complex WAG+F+I+G amino acid substitution model and letting two Markov chains each run for 1,000,000 generation (sufficient for the two separate runs to converge before the second parameter samples were made) while sampling every 10,000 generations at likelihood stationarity in order to avoid autocorrelated parameter estimates.

REFERENCES CITED AND INCORPORATED HEREIN FOR THIS EXAMPLE 1

1. B. Lemieux, M. Miguel, C. Somerville, J. Browse, *Theor. Appl. Genetics* 80, 234 (1990).
2. C. Lu, M. Fulda, J. G. Wallis, J. Browse, *Plant J.* 45, 847 (2006).
3. C. R. Slack, P. G. Roughan, N. Balasingham, *Biochem. J.* 170, 421 (1978).
4. W. Lukowitz, C. S. Gillmor, W. R. Scheible, *Plant Physiol.* 123, 795 (2000).
5. L. Fan, S. Zheng, X. Wang, *Plant Cell* 9, 2183 (1997).
6. I. Heilmann, S. Mekhedov, B. King, J. Browse, J. Shanklin, *Plant Physiol.* 136, 4237 (2004).
7. A. R. Stuitje, *Plant Biotech. J.* 1, 301 (2003).
8. D. Mumberg, R. Müller, M. Funk, *Gene* 156, 119 (1995).
9. R. Hjelmstad, R. Bell, *J. Biol. Chem.* 266, 4357 (1991).
10. D. L. Swofford. *PAUP*. Phylogenetic Analysis Using Parsimony (*and Other Methods), Version 4 (Sinauer Associates, Sunderland, Mass., 2003).
11. F. Ronquist, J. P. Huelsenbeck, *Bioinformatics* 19, 1572 (2003).

Example 2

The *Arabidopsis* Mutant Rod1 was Shown to have a Marked Decrease in Polyunsaturated Fatty Acids in Seeds Table 1A and 1B show that the *Arabidopsis* mutant rod1 of DH4 has a marked decrease in polyunsaturated fatty acids (PUFA) in seeds. Seed fatty acid compositions of the rod1 mutant differ from those of wild type (WT) and the fad2 mutant of *Arabidopsis thaliana*. Compared to the fad2 mutant (5, 7), the fatty acid composition change in DH4 is restricted to seed oil.

TABLES 1A and 1B

Seed fatty acid compositions of the rod1 mutant differ from those of wild type (WT) and the fad2 mutant of *Arabidopsis thaliana*. TAG, triacylglycerol; DAG, diacylglycerol; PC, phosphatidylcholine; PE, phosphatidylethanolamine

|  |  | Mol % of fatty acid species | | | | | |
|---|---|---|---|---|---|---|---|
|  |  | 16:0 | 18:0 | 18:1 | 18:2 | 18:3 | 20:1 |
| A. Mature seeds | | | | | | | |
| TAG | WT | 8.4 | 3.1 | 15.1 | 29.2 | 19.9 | 18.6 |
|  | rod1 | 8.5 | 3.3 | 32.8 | 13.8 | 15.6 | 20.6 |
|  | fad2 | 6.0 | 2.4 | 65.0 | 0.2 | 1.6 | 24.0 |
|  | WT × rod1 | 8.3 | 3.1 | 16.9 | 29.1 | 20.4 | 19.9 |
|  | rod1 × fad2 | 8.3 | 2.4 | 20.1 | 24.3 | 21.0 | 22.4 |
| B. Developing seeds at 9 days after flowering | | | | | | | |
| TAG | WT | 9.2 | 3.7 | 17.9 | 30.5 | 16.2 | 18.6 |
|  | rod1 | 9.9 | 3.8 | 39.1 | 14.2 | 12.3 | 17.9 |
| DAG | WT | 17.0 | 6.5 | 18.2 | 33.8 | 14.2 | 4.3 |
|  | rod1 | 16.1 | 5.3 | 33.8 | 22.2 | 10.9 | 8.6 |
| PC | WT | 17.5 | 2.4 | 7.9 | 45.4 | 19.9 | 3.5 |
|  | rod1 | 16.1 | 1.3 | 6.6 | 39.8 | 31.7 | 1.1 |
| PE | WT | 30.6 | 3.3 | 7.5 | 35.4 | 18.9 | 1.3 |
|  | rod1 | 33.2 | 3.2 | 6.4 | 34.9 | 18.3 | 1.6 |

As shown in Tables 1A and 1B, to further characterize the rod1 effect on seed lipid synthesis, fatty acid compositions of different classes of glycerolipids were analyzed in mature (Table 1A) and developing seeds (Table 1B) at 9 days after flowering, the peak stage for fatty acid synthesis. Compared to wild type, the seed oil of the rod1 mutant of *Arabidopsis* has a marked decrease in polyunsaturated fatty acids, but there is no effect on the fatty acid compositions of leaf or root tissues. The rod1 mutant of *Arabidopsis* has an increased level of 18:1 in both DAG and TAG, but displayed a decreased amount of 18:2 and 18:3 (Tables 1A and 1B). However, for the fatty acids in phosphatidylethanolamine, little difference was detected between rod1 and wild type. Interestingly, analysis of individual lipids from developing seeds of rod1 and wild type revealed that the rod1 mutant had a slightly decreased level of both 18:1 and 18:2 in PC compared to the wild type, and an increase in 18:3, relative to wild-type. Thus, the deficiency in 18:2 and 18:3 was confined to the DAG and TAG of developing rod1 seeds. These findings are consistent with reduced transfer of 18:1 into PC, and indicated that the reduced oleate desaturation is not caused by desaturation activities, but due to a reduced transfer of 18:1 into PC either via de novo synthesis from diacylglycerol (DAG) (8), or via the acyl-CoA:lyso-PC acyltransferase exchange (9).

These changes are similar to, but smaller than, those observed in the fad2 mutants (5, 7) presenting the possibility that rod1 represented a hypomorphic allele of fad2. Whereas mutations at fad2 reduce PUFA synthesis in leaves and roots as well as seeds, changes in fatty acid composition are only seen in seeds of rod1 plants (Table 1A and B, and Table 1C).

TABLE 1C

Fatty acid composition in rod1 leaf and root lipids is similar to that of wild type

| | | Mol % of fatty acid species | | | | | |
|---|---|---|---|---|---|---|---|
| | | 16:0 | 16:3 | 18:0 | 18:1 | 18:2 | 18:3 |
| Leaf | WT | 14.3 ± 0.4 | 13.7 ± 0.4 | 1.1 ± 0.1 | 3.8 ± 0.1 | 16.1 ± 0.5 | 46.3 ± 1.4 |
| | rod1 | 14.3 ± 0.3 | 14.8 ± 0.5 | 1.2 ± 0.1 | 3.8 ± 0.1 | 15.5 ± 0.4 | 44.9 ± 1.5 |
| Root | WT | 22.9 ± 1.6 | — | 1.7 ± 0.3 | 7.6 ± 1.2 | 42.4 ± 1.5 | 25.7 ± 1.6 |
| | rod1 | 23.6 ± 0.8 | — | 1.3 ± 0.1 | 6.8 ± 0.9 | 39.3 ± 0.8 | 29.0 ± 1.0 |

Crosses between rod1 and fad2 produced F1 seeds with PUFA levels considerably higher than those of either parent, confirming that the rod1 mutation is at a locus distinct from fad2. These and additional test crosses indicate that rod1 is a single, recessive Mendelian mutation.

As shown in Table 1A (mature seeds), genetic complementation tests between DH4 and the fad2 mutant further confirmed that the mutant locus rod1 in DH4 is not allelic to fad2. The mutation (as discussed in more detail in EXAMPLE 4 herein below) occurred at the locus At3g15820 that, according to particular aspects of the present invention, normally (wild-type) encodes a novel phosphatidylcholine:diacylglycerol cholinephosphotransferase (PDCT) as determined by enzyme activity assay using heterologous expression in yeast. Applicants have designated this mutant allele as rod1 (reduced oleate desaturation 1), which is a single recessive Mendelian mutation as determined by standard genetic analysis (data not shown).

Example 3

(The *Arabidopsis* mutant rod1 of DH4 was shown to have reduced oleate desaturation in seed oil due to a reduced transfer of 18:1 into PC via de novo synthesis from diacylglycerol (DAG))

The growth, development and seed production of rod1 plants were indistinguishable from WT. The weight of mature rod1 seeds was indistinguishable from WT (17.7±0.2 and 17.9±0.1 μg/seed (av.±s.e.), respectively). Oil content of mature rod1 seeds was 4.9±0.32 μg/seed (av.±s.e.) compared with 4.6±0.19 μg/seed for WT, and the timing of lipid accumulation was similar in the two lines with a maximum 7-9 days after pollination (data not shown). The fatty acid compositions of different classes of glycerolipids extracted from seeds was analyzed during this stage of maximum triglyceride synthesis. Compared to WT, the rod1 mutant had substantially reduced levels of PUFAs in both TG and the immediate precursor diglycerides (DG) (FIGS. 1E-1H). Surprisingly, however, PC contained increased PUFAs with the most highly unsaturated fatty acid, 18:3, accounting for 31.7% of total acyl groups compared to 19.9% in WT. The second most abundant phospholipid in seeds, phosphatidylethanolamine, does not have any major role in TG synthesis, and the fatty acid composition of this lipid was similar in the WT and rod1 samples.

Because PC is the substrate for the FAD2 and FAD3 desaturases that convert 18:1 to 18:2 and 18:3 PUFAs, these data indicated the possibility that the rod1 mutation reduces transfer of 18:1 into PC for desaturation. Prior art models of TG synthesis in oilseeds propose that 18:1 can enter the PC pool either by action of acyl-CoA:lyso-PC acyltransferase (LPCAT) or by the action of CDP-choline:DAG cholinephosphotransferase (CPT) on 18:1-DAG.

To distinguish whether the reduced oleate desaturation is due to a reduced transfer of 18:1 into PC either via de novo synthesis from diacylglycerol (DAG) (8), or via the acyl-CoA:lyso-PC acyltransferase exchange (9), developing seeds were labeled with radioactive acetate (to label fatty acids) (FIGS. 1C and 1D) and radioactive glycerol (to label the lipid backbone) (FIGS. 1A and 1B). In the glycerol chase experiment, PC was the most heavily labeled lipid (30%) in wild type seeds, and it remained relatively stable during the chasing period. A similar amount of label (27%) was also present in DAG at the end of pulse, which decreased during the chasing course, and consequently the lost label was found in TAG (FIG. 1A). In rod1 seeds, only 8% of label was detected in PC, but DAG contained 51% of total radioactivity at the end of pulse. The label present in TAG in rod1 seeds was at similar level to that in wild type. Similar results were also obtained from acetate chasing experiments. These results indicate that rod1 seeds have reduced de novo synthesis of PC from DAG, since a lesion in acyl-CoA:lyso-PC acyltransferase would not be expected to restrict the flux of glycerol into PC.

FIGS. 1A-1D show lipid synthesis in developing seeds of *Arabidopsis*. After 15 minutes of pulse with [14-C] labeled glycerol or acetate, the chase was carried out for 180 minutes. Radio activity in PC, DAG and TAG were determined at 0, 30, 60 and 180 minute time points. Developing seeds were labeled with radioactive acetate (to label fatty acids) (FIGS. 1C and 1D) and radioactive glycerol (to label the lipid backbone) (FIGS. 1A and 1B).

Example 4

(Fine mapping of the *Arabidopsis* mutant rod1 of DH4 was performed and At3g15820 was herein identified as the locus of the rod1 mutant, and for the first time was shown not only to be a phosphatidylcholine:diacylglycerol cholinephosphotransferase (PDCT), but also a PDCT that is highly expressed in developing seeds with the highest level at stage 6 of seed development, which coincides the peak stage of storage deposition)

The de novo PC synthesis in oilseeds is known to be catalyzed by the CDP-choline:DAG cholinephosphotransferases (CPT). There are two homologue genes for CPT in the *Arabidopsis* genome (10). Applicants, therefore, initially presumed (incorrectly) that rod1 was likely a mutation in one of the two *Arabidopsis* CDP-choline:DAG cholinephosphotransferase genes, At1g13560 (AAPT1) or At3g25585 (AAPT2). Surprisingly, however, Applicants' initial mapping data for rod1 placed this gene approximately 20 cM north of AAPT2 on chromosome 3.

Specifically, the genomic DNA covering the two CPT coding regions was sequenced, but there were no sequence mutations in the CPT genes in the rod1 mutant. This result indicated that the CPTs in rod1 function normally and that there was likely another mechanism(s) for synthesizing PC in developing seeds. A map-based cloning approach was therefore conducted to identify the rod1 locus using F2 plants derived from a cross between rod1 and the Landsberg erecta wild type (see "Genetic analysis and map-based cloning of ROD1" under "Materials and Methods" of Example 1 above). This approach allowed identification of a mutation at the locus At3g15820 on chromosome 3. A single nucleotide change from G to A in the first exon of At3g15820 resulted in a change of Trp$^{76}$ to a stop codon (see FIG. 2C). Compared to the wild-type nucleic acid sequence (SEQ ID NO:2), the rod1 allele nucleic acid sequence (SEQ ID NO:4) of this gene coding sequence contains a mutation that creates a stop codon at residue 76 of the predicted opening reading frame.

The identity of ROD1 and At3g15820 was subsequently confirmed by complementing the rod1 mutant with a wild-type ~4-kb genomic sequence (SEQ ID NO:1) including the At3g15820 coding regions and its endogenous promoter and terminator (4 kb genomic fragment of wild-type DNA, including the coding region of At3g15820 and a total of 2 kb of 5' and 3' flanking sequence) (FIG. 2A). This DNA fragment was cloned into a binary plant transformation vector using the DsRed as a selection marker (11). Transgenic seeds were identified by DsRed expression, and their fatty acyl methyl esters (FAMEs) were analyzed by gas chromatography and compared with those of untransformed seeds from the same plants. The fatty acid composition of the transgenic seeds was nearly identical to that of the wild type (FIG. 2B), confirming that the rod1 mutation is indeed at the At3g15820 locus.

FIGS. 2A-2C show that the ROD1 gene was identified as At3g15820 in *Arabidopsis*. (A) The structure of the ROD1 gene with the position of the molecular lesion in the mutant. An approximately 4 Kb region (SEQ ID NO:1) showing exons (bold arrows) and untranslated regions (boxes) was used to complement mutation in rod1. (B) Comparison of seed fatty acid compositions of the At3g15820-transformants (white hatched) and the Col wild-type (white) indicated that At3g15820 fully restored the rod1 mutation (black), thus confirming the identity of ROD1. (C) Deduced amino acid sequence (SEQ ID NO:3) of At3g15820 arranged to show putative transmembrane regions predicted by HMMTOP (underlined). The asterisk marks the position of the change of the codon for Trp 76 into a stop codon) in the mutant sequence SEQ ID NO:4 (single point mutation; G to A in the first exon sequence). The putative lipid phosphate phosphatase motif is shown in bold and italics.

Figure 4:
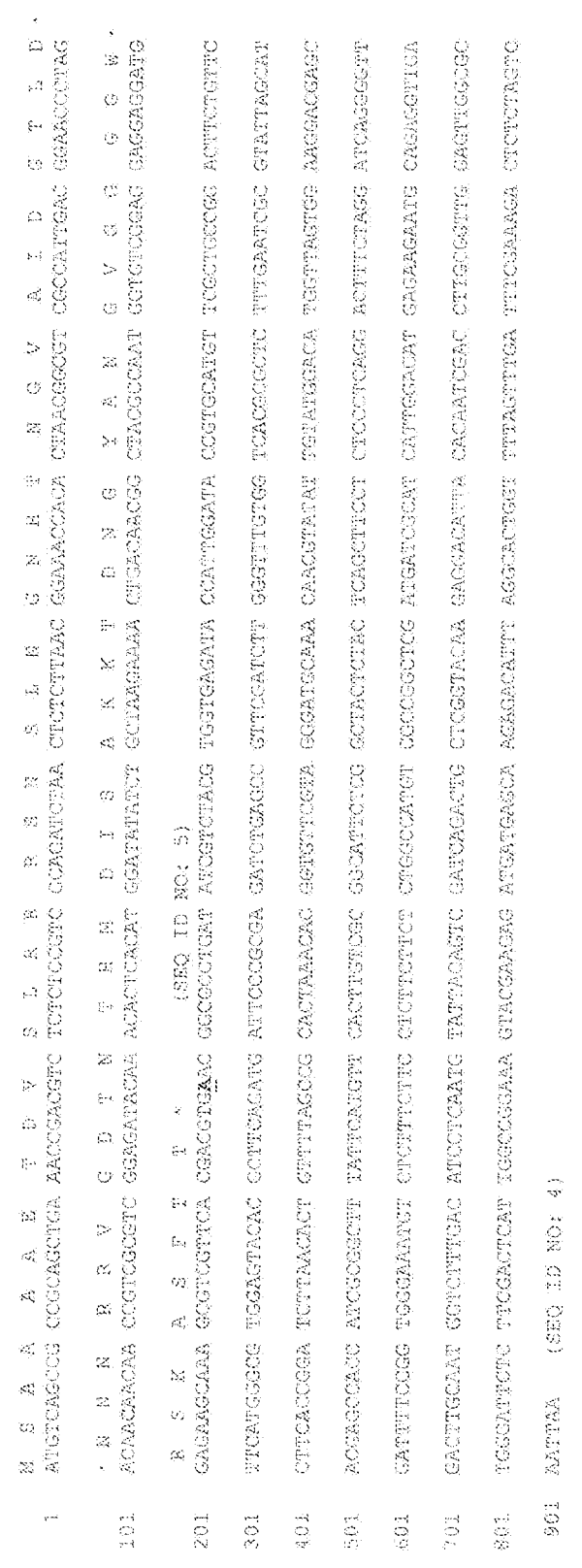

FIG. 4 shows the ROD1 mutant truncated amino acid sequence (SEQ ID NO:5) in DH4. According to particular aspects, a phosphatidylcholine:diacylglycerol cholinephosphotransferase (PDCT) mutant (rod1) coding sequence (SEQ ID NO:4) comprises a G>A change at nucleotide position 228, resulting in premature termination of the PDCT protein to provide a 75 amino acid truncated ROD1 mutant sequence (SEQ ID NO:5).

Analyzing publicly available microarray data (https://www.genevestigator.ethz.ch/) (12) indicated that At3g15820 is highly expressed in developing seeds with the highest level at stage 6 of seed development, which coincides the peak stage of storage deposition. This is in agreement with the seed-specific decreased oleate desaturation in the rod1 mutant (Table 1). According to additional aspects, the only gene in *Arabidopsis* that shares high homology to At3g15820 is At3g15830, which is located just 1.2 kb downstream. However, At3g15830 is only expressed in inflorescence, and Applicants' RT-PCR results also confirmed that At3g15830 is not expressed in developing seeds.

Significantly, At3g15820 was annotated as a putative type 2 phosphatidic acid phosphatase (PAP2)-like protein, however, upon analysis by Applicants, it did not show strong homology to known characterized PAP genes in *Arabidopsis* (AtLPP1, AtLPP2 and AtLPP3) (13, 14). Specifically, ROD1 was rechecked against the PFAM database, and the E-value for identification of a PAP2 domain (0.017) was above the recommended cutoff Not only was the sequence match poor, with only 8 of the 15 most conserved residues being present in ROD1, but the alignment also showed that ROD1 had (would need to have) deletions totaling 61 residues (out of 176) in the center of the motif sequence. The *Arabidopsis* genome contains at least four genes with clearly identified PAP2 domains (E values $<e^{-40}$) including LPP1 (At3g02600) and LPP2 (At1g15080), which have been shown to have PA phosphatase activity. Applicants determined, therefore, that ROD1 contains essentially no sequence homology to these true PAP2 orthologues, and thus concluded that ROD1 encodes a different function. Additionally, when expressed in yeast (*Saccharomyces cerevisiae*) by Applicants, ROD1 did not confer significantly higher PAP activity than the control strain. These results indicated that ROD1 was no likely to possess PA phosphatase activity.

The position-specific iterated BLAST (PSI-BLAST) algorithm was used, and the third iteration identified a non-plant protein phosphatidylcholine: ceramide cholinephosphotransferase (a mammalian phosphatidylcholine:ceramide cholinephosphotransferase (EC 2.7.8.27)), which belongs to a large family of lipid phosphate phosphatases (LPP). This enzyme, also called sphingomyelin synthase (15), catalyzes the transfer of the phosphocholine head group from PC to the alcohol group of ceramide. Applicants appreciated that in the structures and metabolism of sphingolipids, ceramide has a role that is analogous to DAG for glycerolipids. ROD1 is a membrane bound protein containing 5 predicted transmembrane domains according to the program HMMTOP (16), and its sequence contains a LPP motif (FIG. 2C). These results suggested to Applicants that ROD1 would be able to transfer the phosphocholine head group from PC to DAG in plants, an analogous reaction of PC with ceramide in animals. Applicants, therefore, termed this putative new enzyme as phosphatidylcholine: diacylglycerol cholinephosphotransferase (PDCT).

Figure 5:
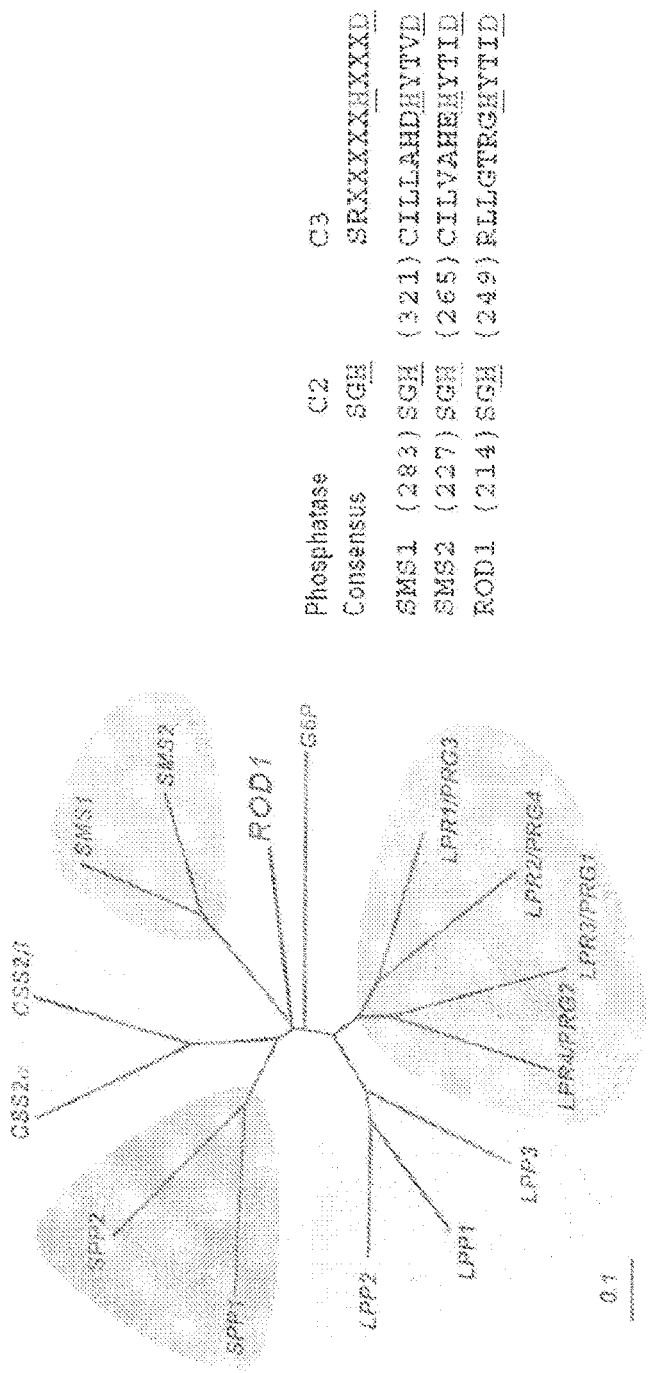
FIG. 5 shows, according to particular exemplary aspects, primary sequence relationships between LPT family members. According to particular aspects, ROD1 belongs to a lipid phosphatase/phosphotransferase family.
Figure 6:
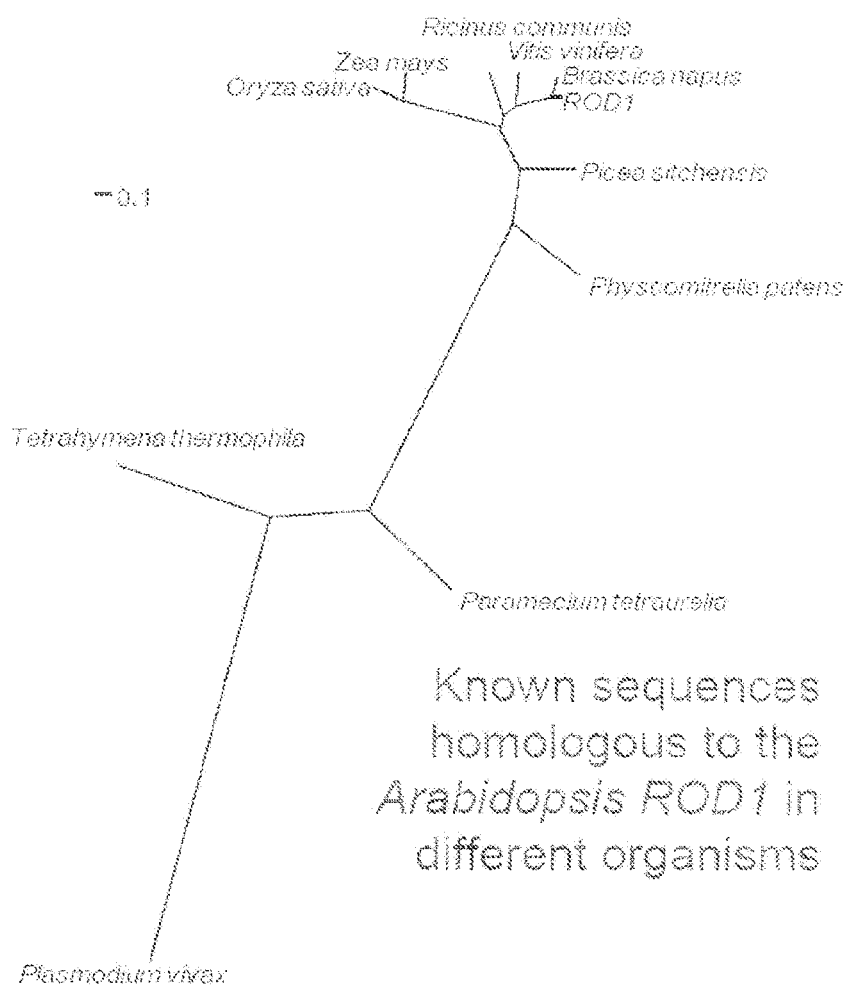
FIG. 6 shows, according to particular exemplary aspects, known sequences homologous to the *Arabidopsis* ROD1 in different organisms. According to particular aspects, ROD1 regulates Equilibration between Diacylglycerol and Phosphatidylcholine in Oilseeds.

Phylogenetic analysis places ROD1 in close relationship to the SMS1 and SMS2 proteins within the LPT family (FIG. 5) and topology prediction programs identify ROD1 as an integral-membrane protein with up to six putative transmembrane domains—similar to predictions for other LPT proteins. In addition, five highly conserved residues in the C2 and C3 domains of SMS1, SMS2 and other LPT proteins are identified at comparable positions in the ROD1 protein (FIG. 2C, and FIG. 5). Plants do not contain sphingomyelin, but the structure of ceramide is similar to that of DG so Applicants considered the possibility that ROD1 catalyzes transfer of phosphocholine from PC to DG in a reaction analogous to that mediated by SMS in animals. Following biochemical convention, Applicants designate this putative enzyme as phosphatidylcholine:diacylglycerol cholinephosphotransferase (PDCT) in the IUPAC subclass EC 2.7.8.

Testing ROD1 for PDCT Activity.

CDP-choline:DAG cholinephosphotransferase is responsible for the initial synthesis of PC and the observation that this reaction is readily reversible in vitro has been invoked to explain the rapid equilibration between the PC and DAG pools that occurs in developing oilseeds. Experimentally (in labeling studies or assays using membrane preparations), however, it is difficult to distinguish between the double action of CDP-choline:DAG cholinephosphotransferase (reaction scheme 1 below) and the single-step reaction catalyzed by PC:DAG cholinephosphotransferase (reaction scheme 2 below). Reaction scheme 2 is simple and analogous to the reaction of PC with ceramide, but to Applicants' knowledge, has not previously been described in any organism—perhaps largely due to the difficulty of distinguishing it from reaction scheme 1. Nonetheless, analogous transfer reactions are known.

Reaction 1:

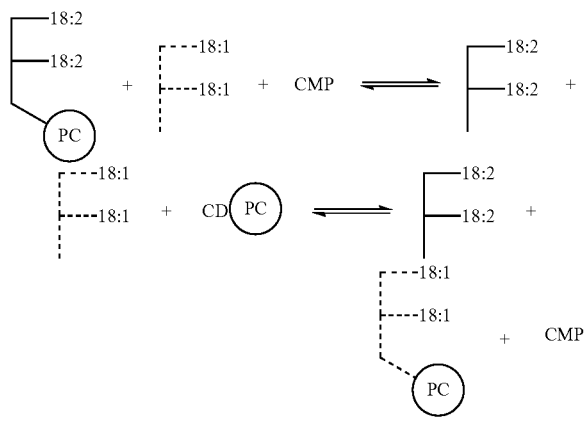

Reaction 2:

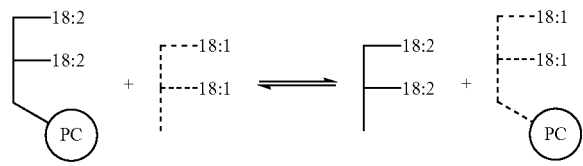

Therefore, Applicants reasoned that the most straightforward way to test ROD1 for PC:DAG cholinephosphotransferase activity would be to express the recombinant protein in a double-mutant yeast strain (e.g., HJ091) lacking all CDP-choline:DAG cholinephosphotransferase activity. In this strain, PC is only synthesized by a reaction sequence involving decarboxylation of phosphatidylserine (PS) to phosphatidylethanolaine (PE) followed by three cycles of methylation to produce PC. Microsomal preparations from this yeast strain will not support incorporation of [$^3$H]-labeled DAG or [$^{14}$C]-labeled choline (supplied as CDP-choline) into PC. Applicants, therefore reasoned that if expression of ROD1 results in conversion of $^3$H-DAG to PC, it will indicate that ROD1 acts as a PC:DAG cholinephosphotransferase.

Figures 3A, 3B, 3C:
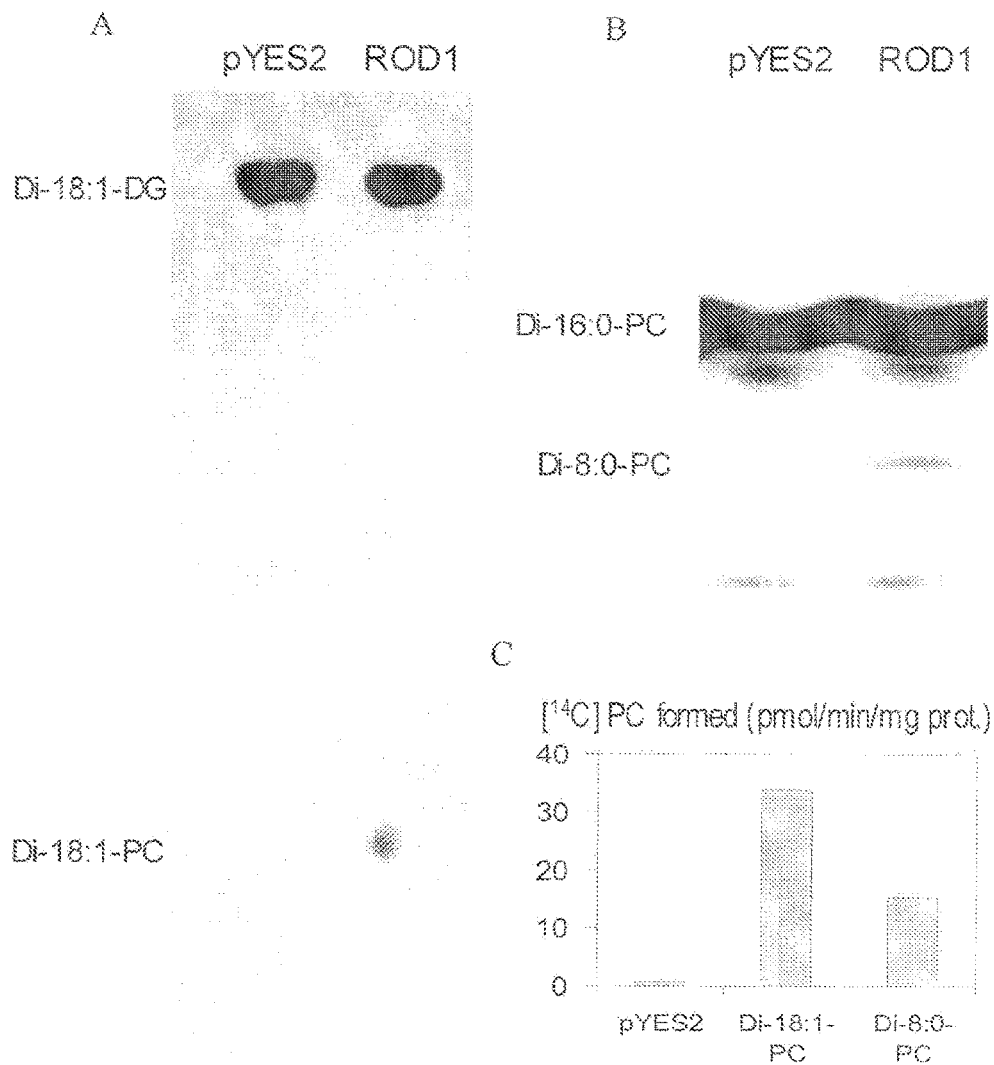
FIGS. 3A-3C show that the ROD1 functions as a phosphatidylcholine:diacylglycerol cholinephosphotransferase.

Therefore, to test ROD1 for PDCT activity, the cDNA of At3g15820 was expressed under control of the inducible GAL1 promoter in a Δcpt Δept double-mutant yeast strain HJ091 (17) lacking all CDP-choline:diacylglycerol cholinephosphotransferase activities. In this strain, PC is only synthesized by a reaction sequence involving decarboxylation of PS to PE, followed by three cycles of methylation reactions (17). Microsomal preparations from this yeast strain do not support incorporation of diacylglycerol and CDP-choline into PC. As expected, the ROD1-transformed yeast microsomes are not able to synthesize radioactive PC when incubated with diolein and [14C]-labeled CDP-Choline (not shown), or [$^{14}$C-glycerol]-diolein and CDP-choline (FIG. 3A). However, [$^{14}$C]-labeled PC was clearly detected when [$^{14}$C]-diolein and PC were provided as substrates. Since the [$^{14}$C]-radiolabel was on the glycerol backbone of diolein, the radioactive PC was apparently resulted from the phosphocholine head group transfer into diolein.

To further confirm this PDCT activity, the ROD1-transformed yeast microsomes were incubated with [$^{14}$C-Choline]-PC and di-8:0-DAG. As shown in FIG. 3B, radiolabeled di-8:0-PC was detected in this assay, indicating the transfer of the phosphocholine headgroup to the di-8:0-DAG. These results indicate that ROD1 does not possess PA phosphatase activity, and substantially confirms that ROD1 rather confers a PDCT activity, which is consistent with the fact that the rod1 mutant is defective in PC synthesis in developing seeds.

FIGS. 3A-3C show that ROD1 functions as a phosphatidylcholine:diacylglycerol cholinephosphotransferase. Microsomes from yeast strain HJ091 transformed with ROD1 convert [14C]glycerol-labeled dioleoylglycerol into 1,2-dioleoyl-sn-glycero-3-phosphocholine (A), or yields 1,2-dioctanoyl-sn-glycero-3-phosphocholine when incubated with [$^{14}$C]Choline-labeled dipalmitoyl phosphocholine and 1,2-dioctanoyl-sn-3-glycerol (B). No new radiolabeled PC products were detected in reactions using HJ091 transformed with the empty vector pYES2 (A, B, C).

Figures 9A, 9B, 9C:
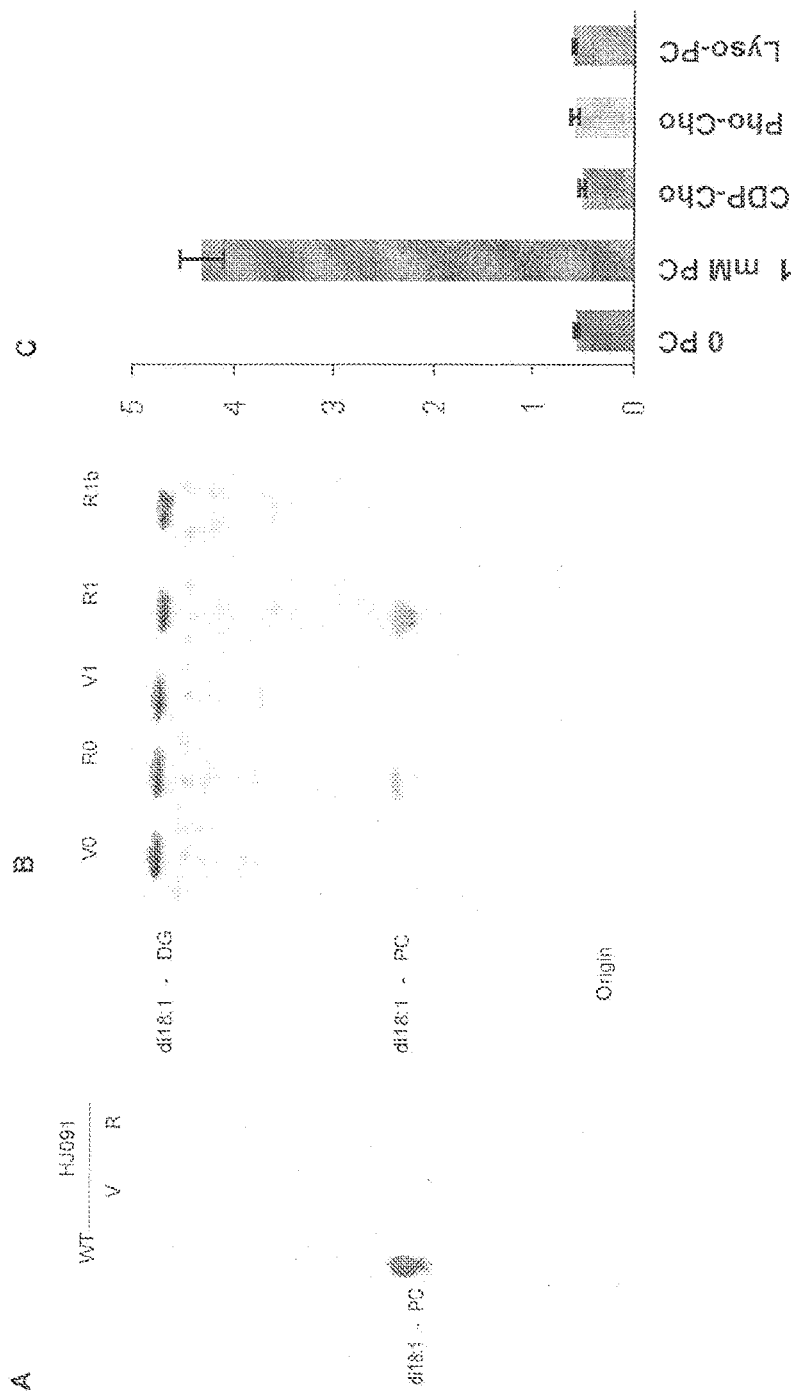
FIGS. 9A-9H show, according to particular exemplary aspects, that ROD1 possesses the activity of a phosphatidylcholine diacylglycerol cholinephosphotransferase (PDCT). (A) TLC image of CPT assays. (B) TLC image of PDCT assays. Microsomes of DBY746 (WT) and HJ091 *S. cerevisiae* cells transformed with p424GPD (V) or p424ROD1 (R) were used, and the TLC solvent system in all experiments is: chloroform/methanol/water=65/25/4 in vol. The substrates are CDP-[14C]Choline and diolein for CPT, and [14C-glycerol]di18:1-DG and PC (0 or 1 mM) for PDCT, respectively. b=boiled microsomal proteins. (C) PDCT activities of ROD1-transformed yeast microsomes in reactions of [14C-glycerol]di18:1-DG with PC (0 or 1 mM), CDP-choline, phosphocholine and lyso-PC, respectively. (D) Microsomes of HJ091 cells transformed with vector p424GPD (V) or p424ROD1 (R) were incubated with di14:0-PC [14C-Choline] and di18:1-DG for the PDCT assays. (E) The effect of pH on PDCT activity. (F-H) The linearity of the PDCT activity as a function of incubation time, added microsomal protein and PC, respectively. Data represent means and standard deviations of three independent reactions.

More specifically, Microsomal preparations from JH091 cells expressing ROD1 and from empty-vector controls were first tested for the ability to synthesize PC from DG and CDP-[$^{14}$C]choline (20). No activity was detected in either control microsomes or those from cells expressing ROD1 (FIG. 9A). However, $^{14}$C-labeled PC was produced when ROD1 microsomes were incubated with dioleoyl-[$^{14}$C]glycerol and this activity was enhanced in the presence of added PC (FIG. 9B). Control microsomes did not have activity in this assay and ROD1 microsomes that had been boiled prior to assay were also inactive. Because the [$^{14}$C] radiolabel was in the glycerol moiety of the [$^{14}$C]-DG substrate, these assays indicate that ROD1 synthesizes [$^{14}$C]-PC PC by transfer of the phosphocholine headgroup from PC to [$^{14}$C]-DG. The activity observed in assays without added PC presumably relied on endogenous PC of the yeast microsomes.

Figures 9D, 9E, 9F, 9G, 9H:
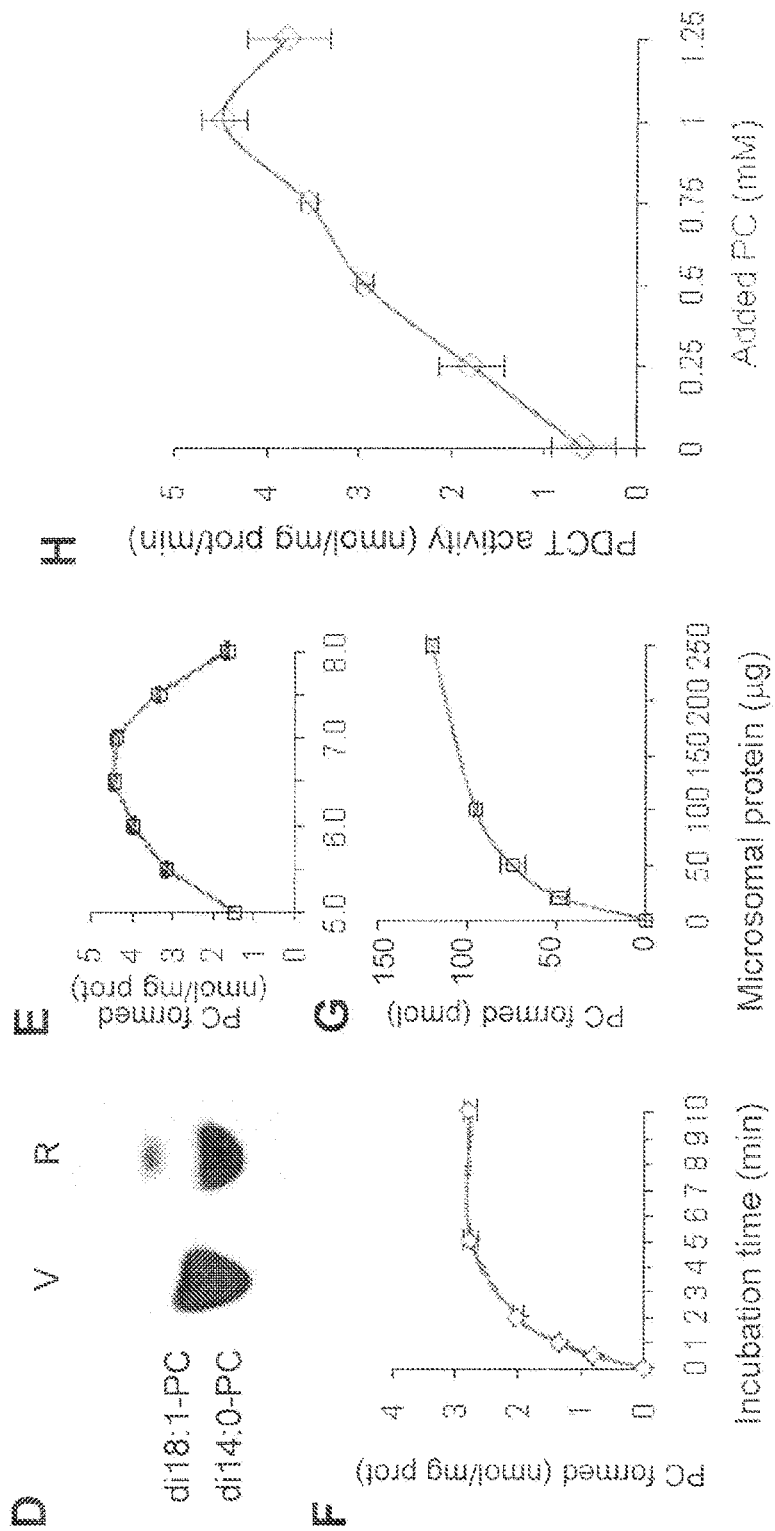

Assays with other possible phosphocholine donors indicated that only the phosphocholine headgroup of PC was accessible to the ROD1 enzyme. Addition of 1 mM CDP-choline, phosphocholine or lyso-PC did not support [$^{14}$C]-PC synthesis at rates higher than ROD1 microsomes without added PC (FIG. 9C). To specifically test for transfer of the PC headgroup, we incubated microsomes with [$^{14}$C]choline-labeled dimyristoyl-PC and unlabeled dioleoyl-DG. In this assay, ROD1 microsomes, but not the control, synthesized dioleoyl-[$^{14}$C]-PC, which separates from the dimyristoyl-[$^{14}$C]PC substrate on thin layer chromatography (FIG. 9D). Additional assays indicated that the PDCT activity was highest at pH 6.5-7 (FIG. 9E). Under the assay conditions used, [$^{14}$C]-PC synthesis increased linearly with incubation time up to 3 min, and with protein concentration up to 50 μg of microsomal protein (FIG. 9F, G). Under optimized assay conditions, PDCT activity was 0.6 nmol/min/mg microsomal protein in the absence of added PC, increasing to 4.5 nmol/min/mg with 1 mM added PC (FIG. 9H).

In summary, Applicants' analyses of the rod1 mutant in *Arabidopsis* and biochemical functional assays using heterologous yeast expression surprisingly establishes that ROD1 (At3g15820) functions as a phosphatidylcholine diacylglycerol cholinephosphotransferase. Specifically, it is responsible for the flux from DAG into PC in developing seeds of seed oil plants, including but not limited to, e.g., *Arabidopsis*).

A minimum estimate of the flux through PDCT can be made from the data in Table 1. In WT seeds, 49.1% of fatty acids are 18:2+18:3, the two products of FAD2 desaturation on PC. In the rod1 mutant, these fatty acids are only 29.4% of the total, indicating that 40%

$$\frac{49.1 - 29.4}{49.1} \times \frac{100}{1}$$

of the 18:1 converted to 18:2+18:3 enters PC via the PDCT enzyme. Sequences homologous to *Arabidopsis* ROD1 are identifiable in many higher plants, including oil crops such as canola (*Brassica napus*), sunflower (*Helianthus annua*) and castor bean (*Ricinus communis*) and it is thus likely that PDCT is an important enzyme of TG synthesis in many plants.

Our discovery of PDCT in *Arabidopsis* has important implication for understanding TG synthesis and for using biotechnology to modify the fatty acid composition of plant oils. For example, because PDCT contributes to the control of PUFA synthesis in seeds, regulation of ROD1 expression could reduce the need for hydrogenation of oils, and the attendant production of unhealthy trans fats (3, 4), as well as providing for the production of biofuels with increased oxidative stability (22). Because PC is also the substrate for enzymes that produce hydroxy-, epoxy-, acetylenic and other modified fatty acids (23-25), our discovery of PDCT provides many opportunities to better understand TG synthesis in different oilseed species and to improve the fatty-acid profiles of vegetable oils for both human health and industrial applications.

Example 5

ROD1 (At3g15820) Orthologs were Identified that have Significant Sequence Homology/Identity According to further aspects of the present invention, many major fatty acid modifications in nature are accomplished by acting on fatty acyl chains esterified on PC, and orthologs of ROD1 genes were herein identified in many other plant species including oil crops such as rapeseed and castor (*Ricinus communis*), etc.

According to particular aspects, expression of the cDNAs in yeast strain HJ091 provides for activity assays of the encoded protein as we did for ROD1. Once the canola ROD1orthologue(s) have been identified, they can be targeted for down-regulation and the resulting plants evaluated for their value in breeding programs to produce lines with increased 18:1 in the seed oil.

Tables 2 and 3 show nucleotide similarity (% identity) and protein sequence similarity (% identity), respectively, for exemplary ROD1 orthologs from *Brassica* (SEQ ID NO:6; SEQ ID NO:7), Moss (SEQ ID NO:16; SEQ ID NO:17), Spruce (SEQ ID NO:14; SEQ ID NO:15), Grape (SEQ ID NO:12; SEQ ID NO:13), Rice (SEQ ID NO:10; SEQ ID NO:11) and Castor (SEQ ID NO:8; SEQ ID NO:9), showing a range of nucleic acid identity from about 46 to 80%, and range of protein sequence identity from about 42 to 85%. According to additional aspects, cloned cDNAs encoding for these orthologs transgenically complement the *Arabidopsis* rod1 mutant.

TABLE 2

ROD1 nucleotide similarity (% identical)

| | Brassica | Moss | Spruce | Grape | Rice | Castor (SEQ ID NO: 8) |
|---|---|---|---|---|---|---|
| Arabidopsis (SEQ ID NO: 18) | 80 | 55 | 54 | 66 | 55 | 62 |
| Brassica (SEQ ID NO: 6) | | 52 | 52 | 64 | 53 | 60 |
| Moss (SEQ ID NO: 16) | | | 59 | 51 | 46 | 52 |
| Sitka spruce (SEQ ID NO: 14) | | | | 61 | 47 | 56 |
| Wine Grape (SEQ ID NO: 12) | | | | | 64 | 71 |
| Rice (SEQ ID NO: 10) | | | | | | 54 |

TABLE 3

ROD1 protein sequence similarity (% identical)

| | Brassica | Moss | Rice | Spruce | Castor | Grape (SEQ ID NO: 13) |
|---|---|---|---|---|---|---|
| Arabidopsis (SEQ ID NO: 3) | 85 | 48 | 46 | 58 | 64 | 71 |
| Brassica (SEQ ID NO: 7) | | 46 | 48 | 59 | 64 | 72 |
| Moss (SEQ ID NO: 17) | | | 42 | 48 | 45 | 47 |
| Rice (SEQ ID NO: 11) | | | | 46 | 51 | 56 |
| Sitka spruce (SEQ ID NO: 15) | | | | | 58 | 65 |
| Castor (SEQ ID NO: 9) | | | | | | 72 |

Therefore, according to preferred embodiments, manipulation of PDCT in oilseeds provides a novel approach (e.g., genetic approach) to modify fatty acid profiles of plant oils to customize and/or optimize plant oils in view of particular end-use requirements. Regardless of the enzymatic identity of ROD1, the effects of the rod1 mutation on the fatty acid compositions of TAG, DAG and PC indicate that down-regulation of ROD1 homologues in crop plants has substantial utility to modulate or reduce levels of 18:2 and 18:3 in the oil while maintaining unsaturation of membrane lipids.

Example 6

*Brassica napus*, *Brassica rapa* (2038 and 370) and *Brassica oleracea* Sequences According to further aspects of the present invention, the *Brassica napus* unigene Bna.6194 is identified as the true *Arabidopsis* ROD1 (At3g15820) homologue. Applicants named Bna.6194 as BnROD1. Quantitative RT-PCR showed that BnROD1 is highly expressed in canola developing seeds. *Brassica napus* is an amphidipoid including *Brassica rapa* and *Brassica oleracea* two subgenomes.

The sequence alignment also suggested that BnROD1 might be the true homologue of *Brassica rapa* unigene Bra. 2038 and *Brassica oleracea* ES948687. Although another *Brassica rapa* unigene Bra.370 also shares highly identity with BnROD1, it cannot be amplified by RT-PCR from developing seed cDNA.

Unigene Bna.6194 (or TC71619 in TIGR)

(SEQ ID NO: 27)

GAGATGAGAAAATAGCAAAGACTTGCGTAAACGTCGCTCTCAAACCTCATCTCATACTCATCGTTTTCGTATGAGTTTTT
GTAGCCCAAACAATCTTCCTTTCTACAGTTTATAATATAAGAAACAATACTTCCTTCGTAATCTCCGCCTCGTATCTCTT
ATATAACTCATCTCTCTAAACCTAAAAAATGTTCCTCTCCGTTAAATCTAACGGTC<u>ATGTCAACTAATACCGTCGTCCCT</u>
CTCCGTCGCAGATCTAACGGATATCACACTAACGGCGTGGCCTTTAACGGAATGGATAATATTGTCAAGAAACCGACGA
CTGCTACACCAACGGCAACGGCAACGGAGGAGTAGAGAGAAGCAAAGCCTCGTTTCTGACATGGACCATGCGTGACGCTG
TCTACGTAGCGAGATACCATTGGATACCGTGTTTCTTTGCGGTCGGAGTTCTGTTCTTTATGGGGGTTGAGTACACGCTC
CAGATGGTTCCGGCGAAGTCTGAGCCGTTCGATATTGGGTTTGTGGCCACGCGCTCTCTAAACCGCGTCTTGGCGAGTTC
ACCGGATCTTAACACCCTTTTAGCGGCTCTAAACACGGTATTCGTAGCGATGCAAACGACGTATATTGTATGGACATGGT
TGATGGAAGGAAGACCACGAGCCACTATCTCGGCTTGCTTCATGTTTACTTGTCGCGGCATTCTTGGTTACTCTACTCAG
CTCCCTCTACCACAGGATTTTTTAGGATCAGGAGTTGATTTTCCGGTGGGAAACGTCTCATTCTTCCTCTTCTATTCTGG
CCACGTAGCCGGTTCAATGATCGCATCCTTGGACATGAGGAGAATGCAGAGGTTGAGACTAGCGATGCTTTTTGACATCC
TCAACATATTACAATCGATCAGACTGCTCGGGACGAGAGGACACTACACGATCGATCTTGCGGTCGGAGTTGGCGCTGGG
ATTCTCTTTGACTCATTGGCCGGGAAGTACGAAGAGATGATGAGCAAGAGACACAATTTAGCCAATGGTTTTAGTTTGAT
TTC<u>TAAAGACTCGCTAGTCAATTAA</u>TCTTTTGTTTTCATTTTAAATGATTAGTTGAACTTGAACATATTTGATTTAGTTA
AAGTCCAATGAATTACA underlined areas are the primers used for amplification of BnROD1 ORF.
Bold-face areas the primers used for real-time PCR.

BnROD1 coding region sequence (from Bna6194)

(SEQ ID NO: 19)

```
  1    ATGTCAACTA ATACCGTCGT CCCTCTCCGT CGCAGATCTA ACGGATATCA CACTAACGGC
 61    GTGGCCTTTA ACGGAATGGA TAATATTGTC AAGAAACCG ACGACTGCTA CACCAACGGC
121    AACGGCAACG GAGGAGTAGA GAGAAGCAAA GCCTCGTTTC TGACATGGAC CATGCGTGAC
181    GCTGTCTACG TAGCGAGATA CCATTGGATA CCGTGTTTCT TTGCGGTCGG AGTTCTGTTC
241    TTTATGGGGG TTGAGTACAC GCTCCAGATG GTTCCGGCGA AGTCTGAGCC GTTCGATATT
301    GGGTTTGTGG CCACGCGCTC TCTAAACCGC GTCTTGGCGA GTTCACCGGA TCTTAACACC
361    CTTTTAGCGG CTCTAAACAC GGTATTCGTA GCGATGCAAA CGACGTATAT TGTATGGACA
421    TGGTTGATGG AAGGAAGACC ACGAGCCACT ATCTCGGCTT GCTTCATGTT TACTTGTCGC
481    GGCATTCTTG GTTACTCTAC TCAGCTCCCT CTACCACAGG ATTTTTTAGG ATCAGGAGTT
541    GATTTTCCGG TGGGAAACGT CTCATTCTTC CTCTTCTATT CTGGCCACGT AGCCGGTTCA
601    ATGATCGCAT CCTTGGACAT GAGGAGAATG CAGAGGTTGA GACTAGCGAT GCTTTTTGAC
661    ATCCTCAACA TATTACAATC GATCAGACTG CTCGGGACGA GAGGACACTA CACGATCGAT
721    CTTGCGGTCG GAGTTGGCGC TGGGATTCTC TTTGACTCAT TGGCCGGGAA GTACGAAGAG
781    ATGATGAGCA AGAGACACAA TTTAGCCAAT GGTTTTAGTT TGATTTCTAA AGACTCGCTA
841    GTCAATTAA
```

BnROD1 translated ORF sequence )

(SEQ ID NO: 20)

MSTNTVVPLRRRSNGYHTNGVAFNGMDNIVKKTDDCYTNGNGNGGVERSKASFLTWTMRDAVYV
ARYHWIPCFFAVGVLFFMGVEYTLQMVPAKSEPFDIGFVATRSLNRVLASSPDLNTLLAALNTV
FVAMQTTYIVWTWLMEGRPRATISACFMFTCRGILGYSTQLPLPQDFLGSGVDFPVGNVSFFLF
YSGHVAGSMIASLDMRRMQRLRLAMLFDILNILQSIRLLGTRGHYTIDLAVGVGAGILFDSLAG
KYEEMMSKRHNLANGFSLISKDSLVN

Unigene Bra. 2038 (*Brassica rapa*) )

(SEQ ID NO: 28)

```
GATGGTAAGGAAACTCTCGTACTCTTCTCTATCTTTTTGTGTGTGTTTCTCGTGTAAAATATTA
TACACTTAAGACGTATAAAAAGAACAACAAGTAAAGCCCAACAAAGACAGATGAGAAAATAGCA
AAGACTTGCGTAAACGTCGCTCTCAAACCTCATCTCATACTCATCGTTTTCGTATGAGTTTTTG
TAGCCCAAACAATCTTCCTTTCTACAGTTTATAATATAAGAAACAATACTTCCTTCGTAATCTC
CGCCTCGTATCTCTTATATAACTCATCTCTCTAAACCTAAAAAATGTTCCTCTCCGTTAAATCT
AACGGTCATGTCAACTAATACCGTCGTCCCTCTCCGTCGCAGATCTAACGGATATCACACTAAC
GGCGTGGCCTTTAACGGAATGGAGAACATTGTCAAGAAAACCGACGACTGCTACACCAACGGCA
ACGGCAACGGAGGAGTAGAGAGAAGCAAAGCCTCGTTTCTGACATGGACCATGCGTGACGCTGT
CTACGTAGCGAGATACCATTGGATACCGTGTTTCTTTGCGGTCGGAGTTCTGTTCTTTATGGGG
GTTGAGTACACGCTCCAGATGGTTCCGGCGAAGTCTGAGCCGTTCGATATTGGGTTTGTGGCCA
CGCGCTCTCTGAACCGCGTCTTGGCGAGTTCACCGGATCTTAACACCCTTTTAGCGGCTCTAAA
CACGGTATTCGTAGCGATGCAGACGACGTATATTGTATGGACATGGTTGATGGAAGGAAGACCA
CGAGCCACTATCTCGGCTTGCTTCATGTTTACTTGTCGCGGCATTCTTGGTTACTCTACTCAGC
TCCCTCTACCACAGGATTTTTTAGGATCAGGAGTTGATTTTCCGGTGGGAAACGTCTCATTCTT
CCTCTTCTATTCTGGCCACGTAGCCGGTTCAATGATCGCATCCTTGGACATGAGGAGAATGCAG
AGGTTGAGACTAGCGATGCTTTTTGACATCCTCAACATATTACAATCGATCAGACTGCTCGGGA
CGAGAGGACACTACACGATCGATCTTGCGGTCGGAGTTGGCGCTGGGATTCTCTTTGACTCATT
GGCCGGGAAGTACGAAGAGATGATGAGCAAGAGACACAATTTAGCCAATGGTTTTAGTTTGATT
TCTAAAGACTCGCTAGTCAATTAATCTTTTGTTTTTATTTTAAATGATTAGTTGAACTTGAACA
TATTTGATTTAGTTAAAGTCCAATGAATTACATTTTTTCTTTCAACTTTAATTGAATAGGGTT
TCATTAGTTTACTTGAACCTAATTAAATGTGTACGTTATTGTGAAATAAAGAAGTTTGTTGTGG
CCTTCCTACAACTATTTCATCAAAAAAAAAAAAAA
```

BrROD1 Coding sequence: )

(SEQ ID NO: 21)

```
ATGTCAACTAATACCGTCGTCCCTCTCCGTCGCAGATCTAACGGATATCACACTAACGGCGTGG
CCTTTAACGGAATGGAGAACATTGTCAAGAAAACCGACGACTGCTACACCAACGGCAACGGCAA
CGGAGGAGTAGAGAGAAGCAAAGCCTCGTTTCTGACATGGACCATGCGTGACGCTGTCTACGTA
GCGAGATACCATTGGATACCGTGTTTCTTTGCGGTCGGAGTTCTGTTCTTTATGGGGGTTGAGT
ACACGCTCCAGATGGTTCCGGCGAAGTCTGAGCCGTTCGATATTGGGTTTGTGGCCACGCGCTC
TCTGAACCGCGTCTTGGCGAGTTCACCGGATCTTAACACCCTTTTAGCGGCTCTAAACACGGTA
TTCGTAGCGATGCAGACGACGTATATTGTATGGACATGGTTGATGGAAGGAAGACCACGAGCCA
CTATCTCGGCTTGCTTCATGTTTACTTGTCGCGGCATTCTTGGTTACTCTACTCAGCTCCCTCT
ACCACAGGATTTTTTAGGATCAGGAGTTGATTTTCCGGTGGGAAACGTCTCATTCTTCCTCTTC
TATTCTGGCCACGTAGCCGGTTCAATGATCGCATCCTTGGACATGAGGAGAATGCAGAGGTTGA
GACTAGCGATGCTTTTTGACATCCTCAACATATTACAATCGATCAGACTGCTCGGGACGAGAGG
ACACTACACGATCGATCTTGCGGTCGGAGTTGGCGCTGGGATTCTCTTTGACTCATTGGCCGGG
AAGTACGAAGAGATGATGAGCAAGAGACACAATTTAGCCAATGGTTTTAGTTTGATTTCTAAAG
ACTCGCTAGTCAATTAA
```

Unigene Bra. 2038 translated ORF sequence (SEQ ID NO: 22)

MSTNTVVPLRRRSNGYHTNGVAFNGMENIVKKTDDCYTNGNGNGGVERSKASFLTWTMRDAVYV
ARYHWIPCFFAVGVLFFMGVEYTLQMVPAKSEPFDIGFVATRSLNRVLASSPDLNTLLAALNTV
FVAMQTTYIVWTWLMEGRPRATISACFMFTCRGILGYSTQLPLPQDFLGSGVDFPVGNVSFFLF
YSGHVAGSMIASLDMRRMQRLRLAMLFDILNILQSIRLLGTRGHYTIDLAVGVGAGILFDSLAG
KYEEMMSKRHNLANGFSLISKDSLVN

ES948687 (*Brassica oleracea*) )

(SEQ ID NO: 29)

GAGATGAGAAAATAGCAAAGACTTGCGTAAACGTCGCTCTCAAATCTCATCTCATACTCATCGT
TTTCGTATGAGTTTTTGTAGCCCAAACAATCTTCCTTTCTACGGTTTATAATATAAGAAACAAT
ACTTCCTTCGTAATCTCCGCCTTGTATCTCTTATATAACTCATCTCTCTAAACCTAAAAAATGT
TCCTCTCCGTTAAATCTAACGGTCATGTCAACTAATACCGTCGTCCCTCTCCGTCGCAGATCTA
ACGGATATCACACTAACGGCGTGGCCTTCAACGGAATGGAGAACATTGTCAAGAAAACCGACGA
CTGCTACACCAATGGCAACGGAGTAGGAGGGAAGAGCAAGGCGTCATTTCTGACATGGACCATG
CGTGACGCTGTCTTCGTAGCGAGATACCATTGGATACCATGTTTCTTTGCTGTCGGAGTTCTGT
TCTTTATGGGGGTTGAGTACACGCTCCAGATGGTTCCGGCGAAGTCTGAGCCGTTCGATATTGG
GTTTGTGGCCACGCGCTCTCTGAACCGCGTCTTGGCGAGTTCACCGGATCTTAACACCCTTTTA
GCGGCTCTAAACACGGTATTCGTAGCGATGCAAACGACGTATATTG ...

ES948687 Partial coding sequence:

(SEQ ID NO: 23)

ATGTCAACTAATACCGTCGTCCCTCTCCGTCGCAGATCTAACGGATATCACACTAACGGCGTGG
CCTTCAACGGAATGGAGAACATTGTCAAGAAAACCGACGACTGCTACACCAATGGCAACGGAGT
AGGAGGGAAGAGCAAGGCGTCATTTCTGACATGGACCATGCGTGACGCTGTCTTCGTAGCGAGA
TACCATTGGATACCATGTTTCTTTGCTGTCGGAGTTCTGTTCTTTATGGGGGTTGAGTACACGC
TCCAGATGGTTCCGGCGAAGTCTGAGCCGTTCGATATTGGGTTTGTGGCCACGCGCTCTCTGAA
CCGCGTCTTGGCGAGTTCACCGGATCTTAACACCCTTTTAGCGGCTCTAAACACGGTATTCGTA
GCGATGCAAACGACGTATATTG ...

ES948687 translated amino acid sequence )

(SEQ ID NO: 24)

MSTNTVVPLRRRSNGYHTNGVAFNGMENIVKKTDDCYTNGNGVGGKSKASFLTWTMRDAVFVAR
YHWIPCFFAVGVLFFMGVEYTLQMVPAKSEPFDIGFVATRSLNRVLASSPDLNTLLAALNTVFV
AMQTTYI ...

Unigene Bra. 370 (*Brassica rapa*) )

(SEQ ID NO: 30)

GCTCTCAAATCTCATATTCATCGTTTTCGTATGAACTTTTGTAGCCCAAACAACCTTCCTTTCC
TTCCACAAGTTTCATATAATATCTCTTATATAACCCATCTCTCTAAGCCTCTCAAAACGTTCTT
CTCCGTTAAATCTAACGGCCATGTCAACTACAACAATCGTCCCTCTCCGTCGCACTTCTAACTC
TCTCAATGAATACCACACTAACGCAGTCGCCTTTGACGGAATCGTCGGGTCAGCAAGTACTAGC
CAAATGGAGGAGATTGTTACGCAAACCGACGACTGCTACGCCAACCCCAACGGAGATGGAGGGA
GAAGCAAGACGTCGTTAATGACGTGGAGGATGTGCAATCCTGTCCACGTGGTGAGAGTCCATTG
GATACCGTGTTTGTTTGCGGTAGGAGTTCTGTTCTTCACGTGCGTAGAGGAGTACATGCTCCAG
ATGATTCCGGCGAGTTCTGAGCCGTTCGATATTGGTTTTGTGGCGACGGGCTCTCTGTATCGCC
TCTTGGCTTCTTCACCGGATCTTAATACCGTTTTAGCTGCTCTCAACACGGTGTTTGTAGGGAT
GCAAACGACGTATATTTTATGGACATGGTTGGTGGAAGGACGACCACGAGCGACCATCTCGGCT

```
-continued
TGCTTCATGTTTACTTGCCGTGGCATTCTGGGTTACTCTACTCAGCTCCCTCTTCCTCAGGATT

TTCTAGGATCAGGGGTAGATTTTCCGGTAGGAAACGTCTCGTTCTT
```

Partial coding sequence:

(SEQ ID NO: 25)

```
ATGTCAACTACAACAATCGTCCCTCTCCGTCGCACTTCTAACTCTCTCAATGAATACCACACTA

ACGCAGTCGCCTTTGACGGAATCGTCGGGTCAGCAAGTACTAGCCAAATGGAGGAGATTGTTAC

GCAAACCGACGACTGCTACGCCAACCCCAACGGAGATGGAGGGAGAAGCAAGACGTCGTTAATG

ACGTGGAGGATGTGCAATCCTGTCCACGTGGTGAGAGTCCATTGGATACCGTGTTTGTTTGCGG

TAGGAGTTCTGTTCTTCACGTGCGTAGAGGAGTACATGCTCCAGATGATTCCGGCGAGTTCTGA

GCCGTTCGATATTGGTTTTGTGGCGACGGGCTCTCTGTATCGCCTCTTGGCTTCTTCACCGGAT

CTTAATACCGTTTTAGCTGCTCTCAACACGGTGTTTGTAGGGATGCAAACGACGTATATTTTAT

GGACATGGTTGGTGGAAGGACGACCACGAGCGACCATCTCGGCTTGCTTCATGTTTACTTGCCG

TGGCATTCTGGGTTACTCTACTCAGCTCCCTCTTCCTCAGGATTTTCTAGGATCAGGGGTAGAT

TTTCCGGTAGGAAACGTCTCGTTCTT ...
```

Unigene Bra. 370 translated amino acid sequence)

(SEQ ID NO: 26)

```
MSTTTIVPLRRTSNSLNEYHTNAVAFDGIVGSASTSQMEEIVTQTDDCYANPNGDGGRSKTSLM

TWRMCNPVHVVRVHWIPCLFAVGVLFFTCVEEYMLQMIPASSEPFDIGFVATGSLYRLLASSPD

LNTVLAALNTVFVGMQTTYILWTWLVEGRPRATISACFMFTCRGILGYSTQLPLPQDFLGSGVD

FPVGNVSF ...
```

TABLE 4

Protein identities of ROD1 and other putative homologues in
B. napus, B.rapa and B. oleracea.

| | BnROD1 | Bna6194 | Bra2038_2 | BoES948687 | ROD1 | ROD2 | Bra370 |
|---|---|---|---|---|---|---|---|
| BnROD1 | 100 | 100 | 100 | 96 | 85 | 76 | 79 |
| Bna6194 | | | 100 | 96 | 85 | 76 | 79 |
| Bra2038_2 | | | | 96 | 85 | 77 | 80 |
| BoES948687 | | | | | 74 | 66 | 74 |
| ROD1 | | | | | | 76 | 71 |
| ROD2 | | | | | | | 68 |
| Bra370 | | | | | | | |

Example 7

Biological Materials, as Provided for Herein, that Contain Relatively High Concentrations of Long Chain Fats with Modest Unsaturation Provide Improved Feedstocks for the Production of Biodiesel and Related Products According to further aspects of the present invention, the quality of a biodiesel derives from the chemical characteristics of the constituent fats within the source biological material. While chemical and physical processing can be employed to alter the fat profile during biodiesel synthesis and processing, these add cost to the end product. Thus methods which alter the fat composition of the biological material during growth and maturation are particularly valuable.

Specific variables of relevance to the quality of a biodiesel derive from an interplay between the cloud point, oxidative stability and energy density. For example; optimal cloud points derive from high melting point oils, which typically are comprised of highly unsaturated and/or short chain fats, however mixtures of this composition are often oxidatively unstable and have low energy densities. Similarly, optimal oxidative stability and energy density derives from oils with long chain fats with low/little unsaturation, however such mixtures typically have undesirable low temperature cloud points.

Accordingly, biological materials, as provided for herein, that contain relatively high concentrations of long chain fats with modest unsaturation provide improved feedstocks for the production of biodiesel and related products.

ADDITIONAL REFERENCES CITED IN RELATION TO EXAMPLES 3-8 (AND INCORPORATED BY REFERENCE HEREIN, FOR THERE REFERRED TO TEACHINGS

1. F. D. Gunstone, Prog. Lipid Res. 37, 277-305 (1998).
2. P. Broun, S. Gettner, C. Somerville, Annu Rev Nutr 19, 197-216 (1999).
3. J. Jaworski, E. B. Cahoon, Curr. Opin. Plant Biol. 6, 178-184 (2003).

4. J. Browse, C. Somerville, *Annu. Rev. Plant Physiol. Plant Mol. Biol.* 42, 467-506 (1991).
5. M. Miguel, J. Browse, *J. Biol. Chem.* 267, 1502-1509 (1992).
6. J. Okuley et al., *Plant Cell* 6, 147-158 (1994).
7. B. Lemieux, M. Miguel, C. Somerville, J. Browse, *Theor. Appl. Genet.* 80, 234-240 (1990).
8. C. R. Slack, L. C. Campbell, J. A. Browse, P. G. Roughan, *Biochem. J.* 263, 217-228 (1983).
9. S. Stymne, A. K. Stobart, *Biochem. J.* 223, 305-314 (1984).
10. J. H. Goode, R. E. Dewey, *Plant Physiol. Biochem.* 37, 445-457 (1999).
11. C. Lu, M. Fulda, J. G. Wallis, J. Browse, *Plant J.* 45, 847-56 (2006).
12. P. Zimmermann, M. Hirsch-Hoffmann, L. Hennig, W. Gruissem, *Plant Physiol.* 136, 2621-32 (2004).
13. T. Katagiri et al., *Plant J.* 43, 107-17 (2005).
14. O. Pierrugues et al., *J. Biol. Chem.* 276, 20300-8 (2001).
15. K. Huitema, J. van den Dikkenberg, J. F. Brouwers, J. C. Holthuis, *Embo J* 23, 33-44 (2004).
16. G. E. Tusnady, I. Simon, *J Mol Biol* 283, 489-506 (1998).
17. S. C. Morash, C. R. McMaster, R. H. Hjelmstad, R. M. Bell, *J. Biol. Chem.* 269, 28769-76 (1994).
18. C. D. Funk, *Science* 294, 1871 (2001).
19. J. G. Wallis, J. L. Watts, J. Browse, *Trends Biochem. Sci.* 27, 467 (2002).
20. H. Steinhart, R. Rickert, K. Winkler, *Eur. J. Med. Res.* 8, 358 (2003).
21. D. M. Muoio, C. B. Newgard, *Annu. Rev. Biochem.* 75, 367 (2006).
22. G. Vogel, J. Browse, *Plant Physiol.* 110, 923 (1996).
23. A. Voelker, A. J. Kinney, *Annu. Rev. Plant Physiol. Plant Mol. Biol.* 52, 335 (2001).
24. R. Zimmermann et al., *Science* 306, 1383 (2004).
25. Y. Guo et al., *Nature* 453, 657 (2008).
26. A. Dahlqvist et al., *Proc. Natl. Acad. Sci. U.S.A.* 97, 6487 (2000).
27. S. Cases et al., *J. Biol. Chem.* 276, 38870 (2001).
28. B. Lemieux, M. Miguel, C. Somerville, J. Browse, *Theor. Appl. Genetics* 80, 234 (1990).
29. M. Miguel, J. Browse, *J. Biol. Chem.* 267, 1502 (1992).
30. S. Stymne, A. K. Stobart, *Biochem. J.* 223, 305 (1984).
31. U. Stahl, K. Stalberg, S. Stymne, H. Ronne, *FEBS Lett.* 582, 305 (2008).
32. J. H. Goode, R. E. Dewey, *Plant Physiol. Biochem.* 37, 445 (1999).
33. C. Lu, M. Fulda, J. G. Wallis, J. Browse, *Plant J.* 45, 847 (2006).
34. O. Pierrugues et al., *J. Biol. Chem.* 276, 20300 (2001).
35. K. Huitema, J. van den Dikkenberg, J. F. Brouwers, J. C. Holthuis, *EMBO J.* 23, 33 (2004).
36. Y. J. Sigal, M. I. McDermott, A. J. Morris, *Biochem. J.* 387, 281 (2005).
37. S. C. Morash, C. R. McMaster, R. H. Hjelmstad, R. M. Bell, *J. Biol. Chem.* 269, 28769 (1994).
38. M. Schmid et al., *Nat. Genet.* 37, 501 (2005).
39. A. J. Kinney, T. E. Clemente, *Fuel Process. Technol.* 86, 1137 (2005).
40. M. Lee et al., *Science* 280, 915 (1998).
41. P. Broun, J. Shanklin, E. Whittle, C. Somerville, *Science* 282, 1315 (1998).
42. E. B. Cahoon et al., *Proc. Natl. Acad. Sci. U.S.A.* 96, 12935 (1999).

The invention claimed is:

1. An oil seed-bearing plant or a part thereof, wherein the plant or part thereof is other than *Arabidopsis*, comprising a mutation of at least one phosphatidylcholine:diacylglycerol cholinephosphotransferase (PDCT) sequence that modifies the expression or activity thereof in one or more seeds or developing seeds of the plant, wherein the level, amount, or distribution of fatty acid unsaturation in the seed oil is modified relative to the seed oil of plants with normal seed expression of the PDCT, and wherein the fatty acid unsaturation in seed oil is differentially reduced relative to fatty acid unsaturation in one or more membrane lipids.

2. The oil seed-bearing plant or a part thereof of claim 1, wherein modifying the expression or activity of the at least one phosphatidylcholine:diacylglycerol cholinephosphotransferase (PDCT) comprises down-regulating at least one of the expression and activity, wherein the level, amount, or distribution of fatty acid unsaturation in the seed oil is reduced.

3. The oil seed-bearing plant or a part thereof of claim 1, comprising two or more different mutations that modify the level, amount, or distribution of fatty acid unsaturation in the seed oil, wherein at least one of the two or more different mutations is a mutation of at least one phosphatidylcholine: diacylglycerol cholinephosphotransferase (PDCT) in one or more seeds or developing seeds of the plant.

4. The oil seed-bearing plant or a part thereof of claim 3, wherein at least one of the two or more different mutations is a FAD2 desaturase mutation that reduces or eliminates FAD2 activity or amount in the seed or developing seed.

5. The oil seed-bearing plant or a part thereof of claim 1, wherein the at least one phosphatidylcholine:diacylglycerol cholinephosphotransferase (PDCT) comprises at least one sequence selected from the group consisting of SEQ ID NO:3, a sequence having at least 46, at least 48%, at least 58%, at least 64%, at least 71% or at least 85% amino acid sequence identity therewith, and PDCT-active portions thereof.

6. The oil seed-bearing plant or a part thereof of claim 5, wherein the at least one phosphatidylcholine:diacylglycerol cholinephosphotransferase (PDCT) comprises at least one sequence selected from the group consisting of SEQ ID NOS:7, 9, 11, 13, 15, 17, 20, 22, 24, 26, and PDCT-active portions thereof.

7. A seed or true-breeding seed derived from the oil seed-bearing plant or a part thereof of claim 1, wherein the seed comprises the mutation of at least one phosphatidylcholine:diacylglycerol cholinephosphotransferase (PDCT) sequence that modifies the expression or activity thereof.

* * * * *